(12) United States Patent
De Haard et al.

(10) Patent No.: US 9,926,364 B2
(45) Date of Patent: Mar. 27, 2018

(54) CHIMERIC HUMAN-LLAMA ANTIGENS AND METHODS OF USE

(71) Applicant: arGEN-X N.V., Breda (NL)

(72) Inventors: Johannes Joseph Wilhelmus De Haard, Breda (NL); Natalie De Jonge, Breda (NL); Anna Hultberg, Breda (NL); Christophe Blanchetot, Destelbergen (BE); Karen Silence, Breda (NL); Peter Ulrichts, Breda (NL); Torsten Dreier, Breda (NL)

(73) Assignee: ARGEN-X N.V., Breda (NL)

( * ) Notice: Subject to any disclaimer, the term of this patent is extended or adjusted under 35 U.S.C. 154(b) by 306 days.

(21) Appl. No.: 14/354,715

(22) PCT Filed: Nov. 5, 2012

(86) PCT No.: PCT/EP2012/071865
§ 371 (c)(1),
(2) Date: Apr. 28, 2014

(87) PCT Pub. No.: WO2013/064700
PCT Pub. Date: May 10, 2013

(65) Prior Publication Data
US 2014/0286976 A1    Sep. 25, 2014

Related U.S. Application Data

(60) Provisional application No. 61/555,417, filed on Nov. 3, 2011.

(51) Int. Cl.
| | |
|---|---|
| C07K 16/00 | (2006.01) |
| C07K 16/18 | (2006.01) |
| A61K 39/00 | (2006.01) |
| C07K 16/28 | (2006.01) |
| G01N 33/68 | (2006.01) |
| C07K 14/705 | (2006.01) |
| C07K 14/715 | (2006.01) |
| C07K 19/00 | (2006.01) |
| C07K 14/435 | (2006.01) |

(52) U.S. Cl.
CPC ............. *C07K 16/18* (2013.01); *A61K 39/00* (2013.01); *C07K 14/435* (2013.01); *C07K 14/70575* (2013.01); *C07K 14/715* (2013.01); *C07K 16/00* (2013.01); *C07K 16/2863* (2013.01); *C07K 16/2875* (2013.01); *C07K 19/00* (2013.01); *G01N 33/6854* (2013.01); *C07K 2317/14* (2013.01); *C07K 2317/22* (2013.01); *C07K 2317/34* (2013.01); *C07K 2319/40* (2013.01)

(58) Field of Classification Search
None
See application file for complete search history.

(56) References Cited

U.S. PATENT DOCUMENTS

| | | | |
|---|---|---|---|
| 5,648,273 A | 7/1997 | Bottaro et al. | |
| 5,686,292 A | 11/1997 | Schwall et al. | |
| 6,099,841 A | 8/2000 | Hillan et al. | |
| 6,207,152 B1 | 3/2001 | Schwall et al. | |
| 6,214,344 B1 | 4/2001 | Schwall et al. | |
| 6,468,529 B1 | 10/2002 | Schwall et al. | |
| 7,476,724 B2 | 1/2009 | Dennis et al. | |
| 7,498,420 B2 | 3/2009 | Michaud et al. | |
| 7,556,804 B2 | 7/2009 | Prat | |
| 7,892,550 B2 | 2/2011 | Dennis et al. | |
| 7,892,770 B2 | 2/2011 | Cao et al. | |
| 8,637,027 B2 | 1/2014 | Hultberg et al. | |
| 2004/0203084 A1* | 10/2004 | Levinson ............... | C07K 16/00 435/7.92 |
| 2005/0272917 A1* | 12/2005 | Jiao ..................... | B01D 15/3804 530/388.1 |
| 2007/0098707 A1 | 5/2007 | Kong-Beltran et al. | |
| 2009/0068179 A1 | 3/2009 | Nayeri et al. | |
| 2009/0175860 A1* | 7/2009 | Stover ................. | C07K 16/2863 424/133.1 |
| 2009/0285807 A1 | 11/2009 | Comoglio et al. | |
| 2009/0298079 A1 | 12/2009 | Basilico et al. | |
| 2010/0016241 A1 | 1/2010 | Kong-Beltran et al. | |
| 2010/0040629 A1 | 2/2010 | Michaud et al. | |
| 2010/0115639 A1 | 5/2010 | Goetsch | |
| 2010/0129369 A1 | 5/2010 | Davies et al. | |

(Continued)

FOREIGN PATENT DOCUMENTS

| | | |
|---|---|---|
| EP | 567585 B1 | 8/1999 |
| EP | 1692178 A1 | 8/2006 |

(Continued)

OTHER PUBLICATIONS

Geld et al (ARD, 66:1679-1682, 2007).*
Eales, Lesley-Jane (Immunology for Life Scientists, pp. 29-30, 2003).*
Van Der Horst, E.H., et al. "Discovery of Fully Human Anti-MET Monoclonal Antibodies with Antitumor Activity against Colon Cancer Tumor Models In Vivo." Neoplasia 11.4 (2009): 355-364.
Toschi Luca, et al. "Single-agent and combination therapeutic strategies to inhibit hepatocyte growth factor/MET signaling in cancer." Clinical Cancer Research 14.19 (2008): 5941-5946.
Basilico, C. et al. "A high affinity hepatocyte growth factor-binding site in the immunoglobulin-like region of Met." Journal of Biological Chemistry 283.30 (2008): 21267-21277.
Christensen, J.G. et al "c-Met as a target for human cancer and characterization of inhibitors for therapeutic intervention." Cancer letters 225.1 (2005): 1-26.

(Continued)

*Primary Examiner* — Brad Duffy
(74) *Attorney, Agent, or Firm* — Lathrop Gage LLP; James H. Velema, Esq.

(57) ABSTRACT

Provided are chimeric, camelid-human (e.g., llama-human) polypeptides comprising a first antigenic polypeptide portion and a second antigenic polypeptide portion wherein the first antigenic portion is a derived from a first portion of a camelid (e.g., llama) and the second antigenic portion is a human polypeptide homolog of a second portion of the camedid antigen. The chimeric polypeptides are useful inter (Continued)

alia for epitope mapping and generation of antibodies that bind to a desired region of human antigen.

18 Claims, 13 Drawing Sheets

(56) References Cited

U.S. PATENT DOCUMENTS

| | | | |
|---|---|---|---|
| 2010/0146650 | A1 | 6/2010 | Goetsch et al. |
| 2010/0285504 | A1 | 11/2010 | Cao et al. |
| 2011/0097262 | A1 | 4/2011 | Goetsch et al. |
| 2011/0142840 | A1 | 6/2011 | Van Der Horst et al. |
| 2011/0239316 | A1 | 9/2011 | Goetsch et al. |
| 2011/0280870 | A1 | 11/2011 | Schwall et al. |
| 2012/0148607 | A1* | 6/2012 | Hultberg ............ C07K 16/2863 424/174.1 |
| 2012/0156206 | A1 | 6/2012 | Hultberg et al. |
| 2014/0205606 | A1 | 7/2014 | Hultberg et al. |

FOREIGN PATENT DOCUMENTS

| | | | |
|---|---|---|---|
| EP | 305203 | B1 | 8/2007 |
| EP | 1957102 | A1 | 8/2008 |
| EP | 2004693 | A2 | 12/2008 |
| EP | 2081592 | A1 | 7/2009 |
| EP | 922102 | B1 | 4/2010 |
| EP | 1641828 | B1 | 4/2010 |
| EP | 1773885 | B1 | 4/2010 |
| EP | 2188312 | A2 | 5/2010 |
| EP | 2195345 | A2 | 6/2010 |
| EP | 1981981 | B1 | 6/2011 |
| EP | 2119448 | B1 | 6/2011 |
| EP | 2336178 | A1 | 6/2011 |
| EP | 2358755 | A1 | 8/2011 |
| WO | 9406909 | A2 | 3/1994 |
| WO | 2005016382 | A1 | 2/2005 |
| WO | 2006015371 | A2 | 2/2006 |
| WO | 20070126799 | A2 | 11/2007 |
| WO | 2008046724 | A1 | 4/2008 |
| WO | 2009007427 | A2 | 1/2009 |
| WO | 2009142738 | A2 | 11/2009 |
| WO | 2010001251 | A2 | 1/2010 |
| WO | 2010059654 | A1 | 5/2010 |
| WO | 2012059561 | A1 | 5/2012 |
| WO | 2012059562 | A1 | 11/2012 |
| WO | 2013064700 | A2 | 5/2013 |

OTHER PUBLICATIONS

Harmsen, M.M. and De Haard, H.J. "Properties, production, and applications of camelid single-domain antibody fragments." Applied microbiology and biotechnology 77.1 (2007): 13-22.
International Search Report for International Application No. PCT/EP2011/069369, dated Jan. 20, 2012, 6 pages.
International Search Report for International Application No. PCT/EP2011/069372, dated Jan. 24, 2012, 7 pages.
Shinkawa, T. et al., The absence of fucose but not the presence of galactose or bisecting N-acetylglucosamine of human IgG1 complex-type oligosaccharides shows the critical role of enhancing antibody-dependent cellular cytotoxicity, J Biol Chem. Jan. 31, 2003; 278(5):3466-73.
Selga et al. 'Epitope mapping of anti-PR3 antibodies using chimeric human/mouse PR3 recombinant proteins'. Clinical and Experimental Immunology. 2004, vol. 135, pp. 164-172.
Wang. 'Epitope Mapping Using Homolog-Scanning Mutagenesis'. Epitope Mapping Protocols. Humana Press. 2009. pp. 289-303.
"ArGEN-X Licenses BioWa's Potelligent Platform to Generate More Potent Antibodies". GEN: Genetic Engineering & Biotechnology News. Jul. 26, 2011 (Jul. 26, 2011). XP055052490. Retrieved from the Internet: URL: http://www.genengnews.com/gen-news-highlights/argen-x-licenses-biowa-s-potelligent-platform-to-generate-more-potent-antibodies/81245465/ [retrieved on Jul. 31, 2014], 2 pages.
Metheringham et al. 'Antibodies designed as effective cancer vaccines'. MAbs. 2009, vol. 1, pp. 71-85.
Written Opinion of the International Searching Authority for PCT/EP2012/071865, dated May 3, 2014. 14 pages.
International Search Report for International Application No. PCT/EP2012/071865, dated Oct. 11, 2013. 8 pages.
Guisti et al. 'Somatic diversification of S107 from an antiphosphocholine to an anti-DNA autoantibody is due to a single base change in its heavy chain variable region.' Proceedings of the National Academy of Sciences, USA. 1987, vol. 84, pp. 2926.
Gussow et al. '[5] Humanization of monoclonal antibodies.' Methods in Enzymology. 1991, vol. 203, pp. 99-121.
Lippincott-Schwartz, Jennifer. 'Antibodies as Cell Biological Tools.' Current Protocols in Cell Biology. 2002 Ch. 16, 2 pages.
Mariuzza et al. 'The structural basis of antigen-antibody recognition.' Annual Review of Biophysics and Biophysical Chemistry. 1987, vol. 16, No. 1, pp. 139-159.
Rudikoff et al. 'Single amino acid substitution altering antigen-binding specificity.' Proceedings of the National Academy of Sciences. 1982, vol. 79, No. 6, pp. 1979-1983.
Winkler et al. 'Changing the antigen binding specificity by single point mutations of an anti-p24 (HIV-1) antibody.' The Journal of Immunology. 2000, vol. 165, No. 8, pp. 4505-4514.

* cited by examiner

Figure 1

```
X54559           1  ECKEALAKSEMNVNMKYQLPNFTAETPIQNVILHEHHIFLGATNYIYVLNEEDLQKVASYKTGPVLEHPD
Lama glama C-Met 1  ECKEALVKSRMNVNMQYQLPNFTAETRIQNVVLHKHHIYLGAVNYIYVLNDKDLQKVAEYKTGPVLEHPH X54559           211 CFPCQDCSSKANLSGGVWKDNINMALVVDTYYDDQLISCGSVNRGTCQRHVFPHNHIADTQSEVHCIFSP
Lama glama C-Met 211 CFPCEDCSHKANLSDGVWKDNINMALLVDTYYDDQLISCGSVHRGTCQRHVLPPDNTADTQSEVYCMYSP X54559           421 QI-EEPSQCPDCVVSALGAKVLSSVKDRFINFFVGNTINSSYFPDHPLHSISVRRLKFTKDGFMFLTDQS
Lama glama C-Met 421 QTDEEPGQCPDCVVSALGIKVLLSEKDRFINFFVGNTIKSSYLPDHSLHSISVRRLKETQDGFKFLTDQS X54559           628 YIDVLPEFRDSYPIKYVHAFESNNFIYFLTVQRETLDAQTFHTRIIRFCSINSGLHSYMEMPLECILTEK
Lama glama C-Met 631 YIDVLPEFQDTYPIKYVHAFESNHFTYPLTVQRETLDAQTFHTRIIRFCSVDSGLHSYMEMPLECILTEK X54559           838 RKKRSTKKEVFNILQAAYVSKPGAQLARQIGASINDDILHGVFAQSKFDSAEPMDRSAMCAFPIKYVNDF
Lama glama C-Met 841 RRRRSIKEEVFNILQAAYVSKPGSQLAKQISANLNDDILYGVFAQSKFDSASPMNRGAVCAFPVKYVNEF X54559           1048 FNKIVNKNNVRCLQHFYGPNHEHCFNRTLLRNSGGCEARDEYRTEFCTALQRVDLFMGQFSEVLLTSIS
Lama glama C-Met 1051 FNKIVNKNNVRCLQHFYGPNHEHCFNRTLLRNSSGCEVRNDEYRTEFCTALQRVDLFTGQFNQVLLTSIS X54559           1258 TFIKGDLCIANLGISEGRFYQVVVSRSGFSTPHVNFLLDSHPVSPEVIVEHTLNQNGYTLVITGKKITKI
Lama glama C-Met 1261 TFIKGDLTIANLGTSESGRFYQVVVSRSGLSTPHVNFLLDSHPVSPEAIVEHPLNQNGYTLVVTGKKITKI X54559           1468 PLNGLGCCRHFQSCSQCLSAPPFVQCGWCHDKCVRSEECLSGTWTQQICLPAIYKVFPNSAPLEGGTRLTI
Lama glama C-Met 1471 PLNGLGCEHFQSCSQCLSAPSFVQCGWCHDKCVQLEECSGGIWTQEICLPIIYKVLPISAPLEGGTILTI X54559           1678 CGWDFGFRRMNKFDLKKTRVLLGNESCTLTLCESTMNTLKCTVGPAMNKHFNMSIITSNGHGTTQYSTFS
Lama glama C-Met 1681 CGWDFGFRRMNYKSDLKKTRVFLGNESCTLTLCESTTNTLKCTVGPAMNEHFNVSIIISNNRGTAQYSTFS X54559           1888 YVDPVITSISPKYGPMAGGLLLTLTGNYLNSGNSRHISIGGKICTLKDVSNCLLECYTPAQTISIEFAVK
Lama glama C-Met 1891 YVDPIITSISPSYGPKTGGLLLTLTSKHLNSGNSRHISIGGKICTLKSVSDSLLECYTPAQTTPISFPVK X54559           2098 LKIDLANREISIFSYREDPIVYELEPIKSFISGGSTITGVGKNLNSVSVPRMVINVHEAGRNFTVACQHR
Lama glama C-Met 2101 LKIDLANREINSFSYREDPVVYETEPIKSFISGGSTITGVGKYLNSVSVLRMVINVHEAGRNFTVACQHR X54559           2308 SNSEIICCTTPSLQCLNLQLPLRKTKAFFMLDGTLSKYFDLIYVHNEVFKPFEKPVMISMGNENVLETRGN
Lama glama C-Met 2311 SNSEIICCTTPSLQCLNLQLPVKTKAFFMLDGIHSKHFDLIYVHNPVFKPFEKPVMISIGNEKVLETKGN X54559           2518 DIDPEAVKGEVLKVGNKGCENIHLHSFAVLCTVPNDLLKLNSELNIEWKQAISSTVLGKVIVQPDQNFT
Lama glama C-Met 2521 DIDPEAVKGEVLKVGNKGCENHSHSFAVLCTVPNDLLKLNSELNIEWKQAVSSTVLGKVIVQPDQNFT
```

X54559 = SEQ ID NO: 1

Lama glama c-Met = SEQ ID NO: 2

Figure 3A.

|  | SEMA | PSI | IPT 1-4 |
|---|---|---|---|
| SP | Human | | |
| SP | LS1 | | |
| SP | LS2 | | |
| SP | LS3 | | |
| SP | LS4 | | |
| SP | LS5 | | |

Figure 3B.

|  | SEMA | PSI | IPT 1 | IPT 2-4 |
|---|---|---|---|---|
| SP | LP6 | | | |
| SP | LP7 | | | |
| SP | LI8 | | | |
| SP | LI9 | | | |
| SP | LI10 | | | |
| SP | LI11 | | | |

Figure 7

```
Human CD70    1  wdvaelqlnhtgpqqdpriywqgqpalgrsflhqpeldkgqlrihrdgiy
Llama CD70    1  wdlaelqlnhtgsrqdprlwqgqpalgrsfvhqpeldnglrvqrsgiy Human CD70   51  mvhiqvtlaicsstasrhhpttlavgicspasrsisllrlsfhqgctia
Llama CD70   51  rlhiqltlncsstagp--hgatltvgicspaahsislrlrflfdrscsva Human CD70  101  sqrltplargdtlctnltgtllpsrntdetffgvqwvrp    SEQ ID NO: 45
Llama CD70   99  sqrltpl-------------------------------    SEQ ID NO: 17
```

Figure 9

```
HUMAN CD70ECD    SLGWDVAELQLNHTGPQQDPRLYWQGGGPALGRSFLHGPELDKGQLRIHRDGIYMVHIQVTLAI
CHIMERA1         SLGWDLAELQLNHTGSRQDPRLRWQGGGPALGRSFLHGPELDKGQLRIHRDGIYMVHIQVTLAI
CHIMERA2         SLGWDLAELQLNHTGSRQDPRLRWQGGGPALGRSFVHGPELDNGQLRVQRSGIYRLHIQLTLTN
CHIMERA3         SLGWDLAELQLNHTGSRQDPRLRWQGGGPALGRSFVHGPELDNGQLRVQRSGIYRLHIQLTLTN
LLAMA(PARTIAL)   ---WDLAELQLNHTGSRQDPRLRWQGGGPALGRSFVHGPELDNGQLRVQRSGIYRLHIQLTLTN

HUMAN            CSSTTASRHHPTTLAVGICSPASRSISLLRLSFHQGCTIASQRLTPLARGDTLCTNLTGTLLP
CHIMERA1         CSSTTASRHHPTTLAVGICSPASRSISLLRLSFHQGCTIASQRLTPLARGDTLCTNLTGTLLP
CHIMERA2         CSSTTASRHHPTTLAVGICSPASRSISLLRLSFHQGCTIASQRLTPLARGDTLCTNLTGTLLP
CHIMERA3         CSSTAGP--HGATLTVGICSPASRSISLLRLSFHQGCTIASQRLTPLARGDTLCTNLTGTLLP
PARTIAL          CSSTAGP--HGATLTVGICSPAAHSISLLRLRFDRSCSVASQRLTPL-------------

HUMAN            SRNTDETFFGVQWVRP    (SEQ ID NO:16)
CHIMERA1         SRNTDETFFGVQWVRP    (SEQ ID NO:18)
CHIMERA          SRNTDETFFGVQWVRP    (SEQ ID NO:19)
CHIMERA3         SRNTDETFFGVQWVRP    (SEQ ID NO:20)
PARTIAL          ----------------    (SEQ ID NO:17)
```

Figure 11

```
HUMANCXCR4     1   MEGISSIPLPLLQIYTSDNYTEE-MGSGDYDSMKEPCFREENANFNKIFLPTIYSIIFLTGIVGNLVILVMGYQKKLRSMTDKYRLHLS
ALPACACXCR4    1   ----SIPLPLFQIFSSDNYIEDDIGSGGDYDYDSIKEPCRQENAHENRVLPIVYSIIFLIGIVGNLVILVMGYQKKLRSMIDKYRLHLS

HUMANCXCR4    90   VADLLFVITLPFWAVDAVANWYFGNFLCKAVHVIYTVNLYSSVLILAFISLDRYLAIVHATNSQRPRKLLAEKVVYVGVWIPALLLTIPD
ALPACACXCR4  256   VADLIFVITLPFWAVDAVANWYFGKFLCKAVHVIYTVNLYSSVLILAFISLDRYLAIVHATNSQRPRKLLAEKVVYVGVWIPALLLTIPD

HUMANCXCR4   180   FIFANVSEADDRYICDRFYPNDLWVVVFQFQHIMVGLILPGIVILSCYCIIISKLSHSKGHQKRKALKTTVILILAFFACWLPYYIGISI
ALPACACXCR4  526   FIFANVTEAEGRYICDRLYPSNLWMVFHFQHIMVGLILPGIVILSCYCIIISKLSHSKGYQKRKALKTTVILILAFFACWLPYYIGISI

HUMANCXCR4   270   DSFILLEIIKQGCEFENTVHKWISITEALAFFHCCLNPILYAFLGAKFKTSAQHALTSVSRGSSLKILSKGKRGGHSSVSTESESSSFHS
ALPACACXCR4  796   DCFILLEIIQQGCEFESIVHKWISITEALAFFHCCLNPILYAFLGAKFKTSAQHALISVSRGSSIKILSKGKRGHSSVSTESESSSFHS

HUMANCXCR4   360   S-   (SEQ ID NO:22)
ALPACACXCR4 1066   S*   (SEQ ID NO:21)
```

Figure 12

```
HUIL1BETA    1   MAEVPELASEMMAYYSGNEDDLFFEADGPKQMKCSFQDLDLCPL-DGGIQLRISDHHYSKGFRQAASVVV
LAMAIL1BETA  1   MATVPEPTSEMMAYYSDNDNDLFFEADGPKQRKCCVQPPDLGSIGDEGIQLQISHQLYNKSFRQVVSLTV

HUIL1BETA    70  AMDKLRKMLVPCPQTFQENDLSTFFPFIFEEEPIFFDTWDNEAYVHDAPVRSINCTLRDSQQKSLVMSGP
LAMAIL1BETA  71  AMEKLSKCTY--SQYFQDDLRNIESLIFEEEPVTFETCADD-FVCDAVVQSLYCKLQDKEQKSMVLASP

HUIL1BETA    140 YELKALHLQGQDMEQQVVFSMSFVQGEESNDKIPVALGLIKEKNLYLSCVLKDDKPTLQLESVDPKNYPKK
LAMAIL1BETA  138 YVLQALHLLAQDMSREVVFCMSFVQGDENNSKTPVVLGLIKEKNLYLSCVMKGDKPTLQLEALDPKSYPRK

HUIL1BETA    210 KMEKRFVFNKIEINNKLEFESAQFPNWYISTSQAENMPVFLGGTKGGQDITDFTMQFVSS        (SEQ ID NO:46)
LAMAIL1BETA  208 NMEKRFVFYKTEIKDRVEFESALYPNWYISTSTAEQRPVFLGQSRGGQDITDFTMETLSP        (SEQ ID NO:47)
```

US 9,926,364 B2

CHIMERIC HUMAN-LLAMA ANTIGENS AND METHODS OF USE

RELATED APPLICATIONS

This application is a 35 U.S.C. § 371 filing of International Application No. PCT/EP2012/071865, filed Nov. 5, 2012, which claims priority to U.S. Provisional Application No. 61/555,417 filed Nov. 3, 2011, which is incorporated herein by reference in its entirety.

TECHNICAL FIELD

The present invention relates to chimeric, camelid/non-camelid polypeptides, in particular chimeric, camelid/non-camelid antigens. In certain aspects, the invention relates to chimeric, camelid-human (e.g., llama-human) polypeptides comprising a first antigenic polypeptide portion and a second antigenic polypeptide portion wherein the first antigenic portion is a derived from a first portion of a camelid (e.g., llama) and the second antigenic portion is a human polypeptide homolog of a second portion of the camelid antigen. The chimeric polypeptides are useful inter alia for epitope mapping and generation of antibodies that bind to a desired region of human antigen.

BACKGROUND

It has recently been discovered that immunization of camelids (e.g., llamas) with non-camelid antigens (e.g., human antigens) results in production of conventional heterotetrameric antibodies with highly desirable properties. These conventional camelid antibodies have a strikingly high amino acid sequence and structural homology to human antibodies, and they bind to the non-camelid target antigen with high affinity. These antibodies also cover a wide diversity of epitopes on the non-camelid target antigen. Taken together, the properties of conventional camelid antibodies make them particularly attractive as therapeutics for the treatment of human disease.

It is often desirable to generate antibodies against precisely defined epitopes. Prior art techniques for raising antibodies against defined epitopes have generally involved the use of short peptides. These peptides can be used as immunogens to generate antibodies against only the target epitope or as selection tools to identify antibodies that bind the target epitope. This approach works well for linear epitopes but is often unsuccessful at generating or identifying antibodies that bind to epitopes that only exist in the native, 3-dimensional form of an antigen (i.e., conformational epitopes).

Accordingly, there is a need in the art for improved methods and compositions for the generation and selection of conventional camelid antibodies.

SUMMARY OF THE INVENTION

The invention generally provides chimeric polypeptides comprising a first portion derived from a camelid polypeptide (e.g., a llama polypeptide) and a second portion derived from non-camelid polypeptide homologue of the camelid polypeptide (e.g., a human homologue), and methods for using the same. The invention is based in part on the surprising discovery that camelid antibodies are not produced by camelids in response to immunization with "self" proteins (i.e., camelid polypeptides).

The chimeric polypeptides disclosed herein are particularly useful for producing and characterizing antibodies against non-camelid polypeptides (e.g. therapeutically important human polypeptides). The chimeric polypeptides are particularly advantageous in that they allow for the production and selection of antibodies to a desired region of a non-camelid protein in its native conformation. For example, the chimeric polypeptides of the invention (e.g., llama/human chimeras) can be used for the following applications: immunizations to identify antibodies recognizing a specific epitope or domain on a non-camelid protein or an antibody for generation of anti-idiotypic antibodies; selection and screening of antibodies from immune libraries specific for a particular epitope or domain; epitope mapping of antibodies; mapping of functional domains of antigens (e.g., receptor-ligand interaction sites); purification of domain-specific antibodies, and quantification/identification of individual antibodies present in an antibody mixture (e.g., a Human c-Met SEMA/Llama c-Met IPT for quantification of a SEMA binder and a Llama/Human IPT for quantification of an IPT binder).

Accordingly, in one aspect the invention provides a chimeric polypeptide comprising a first portion derived from a camelid polypeptide and a second portion derived from non-camelid polypeptide homologue of the camelid polypeptide, wherein the chimeric polypeptide does not comprise a camelid VHH, VH or VL domain polypeptide.

In certain embodiments, the first portion and the second portion are derived from non-corresponding regions of the camelid polypeptide and the non-camelid polypeptide homologue.

In certain embodiments, the camelid polypeptide is a llama polypeptide.

In certain embodiments, the non-camelid polypeptide homologue is a human polypeptide homologue of the camelid polypeptide.

In certain embodiments, the camelid polypeptide and the non-camelid polypeptide homologue are directly linked (e.g., genetically and/or chemically). In other embodiments, the camelid polypeptide and the non-camelid polypeptide homologue are linked (e.g., genetically and/or chemically) though an intervening linker moiety.

In certain embodiments, the chimeric polypeptide has a similar structural conformation to the llama or human polypeptide.

In certain embodiments, the chimeric polypeptide shares at least one functional property with the llama or human polypeptide.

In certain embodiments, the chimeric polypeptide is a cell surface receptor, receptor ligand, or fragment thereof. Suitable ligands include without limitation, cytokines, chemokines, hormones, growth factors, or fragments thereof. In a particular embodiment, the chimeric polypeptide is a chimeric c-Met, CD70, CXCR4, IL-1beta polypeptide, or fragment thereof. In a preferred embodiment, the chimeric polypeptide comprises the amino acid sequence set forth in any one of SEQ ID No. 3-13, and 16-56.

In other aspects, the invention provides nucleic acid molecules encoding the chimeric polypeptide disclosed herein, expression containing these nucleic acid molecules, and host cells containing the nucleic acid molecules and/or expression vectors In another aspect, the invention provides a method for mapping the binding site of an antibody that specifically binds to a non-camelid antigen, the method generally comprising: contacting the antibody with a plurality of chimeric polypeptides of the invention wherein each polypeptide comprises a different portion of the non-camelid antigen; and identifying a chimeric polypeptide bound by the antibody, thereby mapping the binding site of the antibody.

In certain embodiments, the non-camelid antigen is a human antigen.

In another aspect, the invention provides a method for generating an immune response against a portion of a non-camelid antigen, the method generally comprising immunizing a camelid with a chimeric polypeptide of the invention wherein the polypeptide comprises the portion of the non-camelid antigen.

In certain embodiments, the camelid portion of the chimeric polypeptide is from the same species of camelid as the camelid being immunized.

In certain embodiments, the camelid portion of the chimeric polypeptide is not immunogenic in the immunized camelid.

In certain embodiments, the camelid is a llama.

In another aspect, the invention provides a method for purifying an antibody that specifically binds to a portion of a non-camelid antigen, the method generally comprising: contacting a plurality of camelid antibodies with a chimeric polypeptide of the invention, wherein the polypeptide comprises the portion of the non-camelid antigen; and separating from the plurality of antibodies an antibody that binds to the chimeric polypeptide, thereby purifying an antibody that specifically binds to the non-camelid antigen.

In certain embodiments, the non-camelid antigen is a human antigen.

In certain embodiments, the plurality of camelid antibodies is isolated from the serum of a camelid.

In certain embodiments, the plurality of camelid antibodies is present in an expression library. In one embodiment, the expression library is derived from the antibody repertoire of a camelid immunized with the non-camelid antigen. In one embodiment, the expression library is a phage display library.

BRIEF DESCRIPTION OF THE DRAWINGS

The invention will be further understood with reference to the following experimental examples and the accompanying Figures:

FIG. 1. Alignment of human and *Llama glama* c-Met amino acid sequences.

FIG. 3. Schematic illustration of the structure of chimeric llama-human c-Met constructs prepared for: (A) peptide mapping of mAb (e.g. 36C4) binding to the SEMA domain of c-Met. Light grey shading indicates llama c-Met sequence (LS); dark grey shading indicates human c-Met sequence (hS). The relative positions of the signal sequence, SEMA domain, PSI domain and IPT domains 1, 2, 3 and 4 are indicated; (B) peptide mapping of mAb (e.g. 48A2) binding to the PSI-IPT1 domain of c-Met. Light grey shading indicates llama c-Met sequence; dark grey shading indicates human c-Met sequence. The relative positions of the signal sequence, SEMA domain, PSI domain and IPT domains 1, 2, 3 and 4 are indicated.

FIG. 7. Alignment of the amino acid sequence of the human and llama CD 70 ECD.

FIG. 9. Alignment of the amino acid sequence of the human, llama CD70 ECD and chimeras thereof.

FIG. 11. Alignment of the amino acid sequence of the human and alpaca CXCR4.

FIG. 12. Alignment of the amino acid sequence of the human and llama IL-1-beta

DETAILED DESCRIPTION OF THE INVENTION

A. Definitions

Figure 2A:
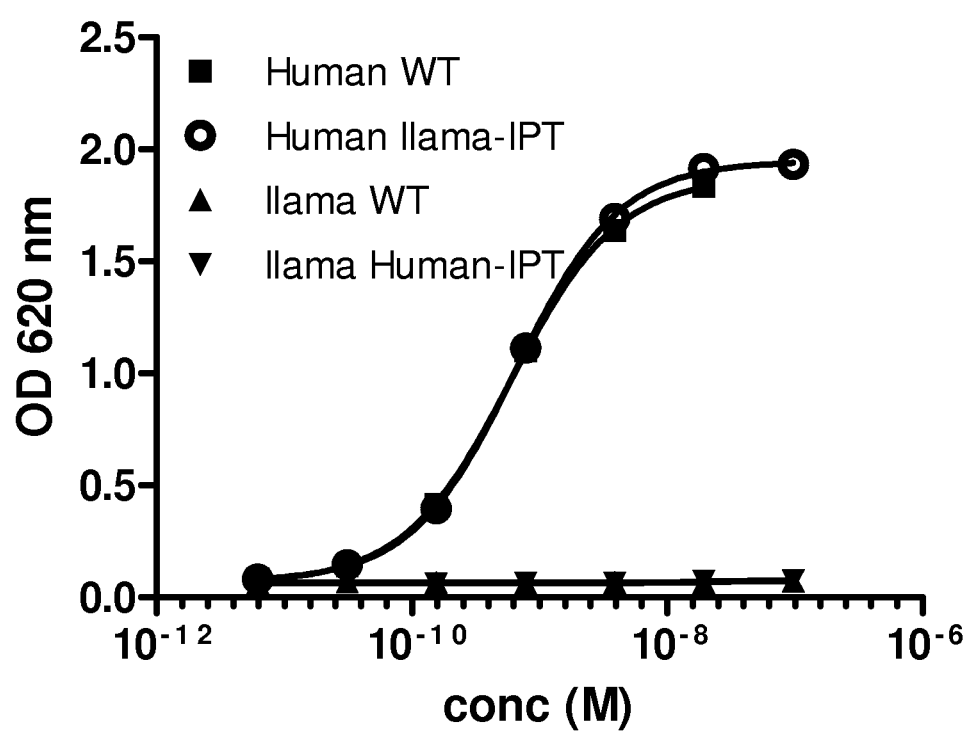
FIG. 2A-B. Domain mapping of mAbs using chimeric c-Met ECD. 36C4 binding to the human c-Met (WT) and the human/llama IPT1-4 indicating binding to the SEMA-PSI region (A). Binding of mAb 13E6 to the human c-Met and to the llama/human IPT1-4 (B).

As used herein the term "chimeric" polypeptide refers to a polypeptide comprising a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric polypeptide may be created, for example, by chemical synthesis, or by creating and translating a polynucleotide in which the peptide regions are encoded in the desired relationship. The chimeric polypeptides of the invention exclude fusion proteins comprising camelid VHH, VH and/or VL domains, or humanised variants thereof, fused to the constant domains of a human antibody, e.g. human IgG1, IgG2, IgG3 or IgG4.

Designation of the portion of the chimera that is derived from a camelid polypeptide as the "first" portion and the portion of the chimera being derived from the non-camelid homologue of the camelid polypeptide as the "second" portion is not intended to imply any particular structural arrangement of the "first" and "second" portions within the chimera. By way of non-limiting example, in certain embodiments the "chimeric" polypeptide may comprise an N-terminal portion derived from the camelid species and a C-terminal portion derived from the non-camelid species, or it may comprise an N-terminal portion derived from the non-camelid species and a C-terminal portion derived from the camelid species comprise. In other embodiments, the chimeric polypeptide may comprise an internal portion derived from the camelid species flanked N-terminally and C-terminally by portions derived from the non-camelid species, or it may comprise an internal portion derived from the non-camelid species flanked N-terminally and C-terminally by portions derived from the camelid species. The chimeric polypeptide may comprise more than one portion derived from the camelid species, the non-camelid species or both species.

As used herein the term "derived from" a designated protein (e.g. a camelid polypeptide or a non-camelid polypeptide homologue) refers to the origin of the polypeptide sequence.

As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. a human antigen). As explained elsewhere herein, "specificity" for a particular human antigen does not exclude cross-reaction with species homologues that antigen. Antibodies and immunoglobulins comprise light and heavy chains, with or without an interchain covalent linkage between them. Basic immunoglobulin structures in vertebrate systems are relatively well understood.

As used herein, the generic term "immunoglobulin" comprises five distinct classes of antibody that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa or lambda (κ,λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (λ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains.

As used herein, the term "VHH" refers to variable domain of a heavy-chain antibody (see e.g., Hamers-Casterman, et al. Nature. 1993; 363; 446-8, which is hereby incorporated by reference in its entirety).

As used herein, the terms "VH" and "VL" refer to the variable heavy and variable light chains of conventional antibodies, respectively.

As used herein, the terms "c-Met protein" or "c-Met receptor" or "c-Met" are used interchangeably and refer to the receptor tyrosine kinase that, in its wild-type form, binds Hepatocyte Growth Factor (HGF). The terms "human c-Met protein" or "human c-Met receptor" or "human c-Met" are used interchangeably to refer to human c-Met, including the native human c-Met protein naturally expressed in the human host and/or on the surface of human cultured cell lines, as well as recombinant forms and fragments thereof and also naturally occurring mutant forms. Specific examples of human c-Met include, e.g., the human polypeptide encoded by the nucleotide sequence provided in GenBank accno. NM000245, or the human protein encoded by the polypeptide sequence provided in GenBank accno. NP000236, or the extracellular domain (ECD) thereof. The single chain precursor c-Met protein is post-translationally cleaved to produce the alpha and beta subunits, which are disulfide linked to form the mature receptor.

As used herein, the terms "CD70 protein" or "CD70 antigen" or "CD70" are used interchangeably and refer to a member of the TNF ligand family which is a ligand for TNFRSF27/CD27. The terms "human CD70 protein" or "human CD70 antigen" or "human CD70" are used interchangeably to refer specifically to the human homolog, including the native human CD70 protein naturally expressed in the human body and/or on the surface of cultured human cell lines, as well as recombinant forms and fragments thereof. Specific examples of human CD70 include the polypeptide having the amino acid sequence shown under NCBI Reference Sequence Accession No. NP001243, or the extracellular domain thereof.

As used herein, the term "IL-1 beta" refers to interleukin-1beta. IL-1 beta nucleotide and polypeptide sequences are well known in the art. An exemplary human IL-1 beta amino sequence is set forth in GenBank deposit GI:157835147.

As used herein, the term "CXCR4" refers to C-X-C chemokine receptor type 4. CXCR4 nucleotide and polypeptide sequences are well known in the art. An exemplary human CXCR4 amino sequence is set forth in GenBank deposit GI: 56790927.

B. Chimeric Polypeptides

In one aspect, the invention provides a chimeric polypeptide comprising a first portion derived from a camelid polypeptide and a second portion derived from non-camelid polypeptide homologue of the camelid polypeptide, wherein the chimeric polypeptide does not comprise a camelid VHH, VH or VL domain polypeptide.

Chimeric polypeptides of the invention can be generated from any homologous pairs of camelid and non-camelid polypeptide, with the exception of camelid VHH, VH or VL domain polypeptides. Suitable classes of polypeptide for chimerization include, without limitation, cell surface receptors, hormones and growth factors. Exemplary chimeric polypeptides are exemplified herein.

Camelid polypeptides for use in the chimeric polypeptides of the invention can be from any camelid. In certain embodiments the camelid species may be selected from the group consisting of camel, llama, dromedary, vicuna, guanaco and alpaca. In certain embodiments, the camelid species is a llama (*Lama glama*).

Non-camelid polypeptide homologues for use in the chimeric polypeptides of the invention can be from any animal or plant. In certain embodiments, the non-camelid species is a mammal (e.g., a human).

Chimeric polypeptides can be prepared using any art recognised means. In certain embodiments, the chimeric polypeptides are prepared using recombinant DNA techniques. In other embodiments, the chimeric polypeptides are prepared by chemical synthesis.

In certain embodiments, the camelid polypeptide and the non-camelid polypeptide homologue are directly linked. In one embodiment, the camelid polypeptide and the non-camelid polypeptide homologue are genetically linked. In such cases, a chimeric nucleic acid molecule is prepared by recombinant DNA techniques. In general, a nucleic acid molecule is prepared that encodes the desired portions of the camelid polypeptide and non-camelid polypeptide homologue, and the resultant chimeric polypeptide is expressed from the nucleic acid using a suitable expression system (e.g., a cellular or cell-free expression system).

In other embodiments, the camelid polypeptide and the non-camelid polypeptide homologue are chemically linked. Any art recognized chemistry can be employed for such chemical linkage. In one embodiment, the camelid polypeptide and the non-camelid polypeptide homologue are linked though an intervening linker moiety.

In general, it is desirable that the chimeric polypeptide has a similar structure and/or functionality to the parent camelid and non-camelid polypeptides. This is especially desirable when the chimeric polypeptide is used as an immunogen, for epitope mapping studies, and/or for the selection of antibodies that bind specifically to the non-camelid portion of the chimeric polypeptide. Accordingly, in certain embodiments, the chimeric polypeptide has a similar structural conformation to the parental camelid or non-camelid polypeptide. In other embodiments, the chimeric polypeptide shares at least one functional property with the camelid or non-camelid polypeptide.

C. Uses of Chimeric Polypeptides

I. Immunogens

The chimeric polypeptides disclosed herein are especially useful as immunogens. As disclosed herein, camelid antibodies are generally not produced by camelids in response to immunization with "self" proteins (i.e., camelid polypeptides). Accordingly, immunization of a camelid with a chimeric polypeptide of the invention results in the production of antibodies preferentially against the non-camelid portion of the chimera. This allows for the production of antibodies to a desired region of a non-camelid protein whilst keeping that region in its native conformation.

Accordingly, in one aspect the invention provides, a method for generating an immune response against a portion of a non-camelid antigen, the method comprising immunizing a camelid with a chimeric polypeptide disclosed herein, wherein the chimeric polypeptide comprises the portion of the non-camelid antigen.

Any camelid can be immunized in the methods of the invention. In certain embodiments, the camelid is a llama. It not essential that camelid portion of the chimeric polypeptide immunogen be derived from the same camelid species, so long as the immunized camelid recognises the camelid portion as a self antigen, and does not produce antibodies to the camelid portion of the immunogen. In certain embodiments, the camelid portion of the chimeric polypeptide immunogen is derived from the same species of camelid as that being immunized.

Any chimeric polypeptide comprising a first portion derived from a camelid polypeptide and a second portion derived from non-camelid polypeptide homologue can be used as the immunogen in the methods of the invention. In a preferred embodiment, the chimeric polypeptide comprises a portion from a llama polypeptide and a portion from a human polypeptide homologue of the llama polypeptide (i.e., a llama-human chimera).

Immunization of camelids can be performed using any art recognized methods (see, e.g., De Haard H, et al., J Bacteriol. 187: 4531-41, 2005, which is hereby incorporated by reference in its entirety).

II. Selection of Antibodies

The chimeric polypeptides disclosed herein are also useful for the selection and purification of antibodies that bind to a desired portion of a non-camelid antigen. Such selection and purification methods generally involve: contacting a plurality of camelid antibodies with a chimeric polypeptide disclosed herein, where the chimeric polypeptide comprises the desired portion of the non-camelid human antigen; and separating from the plurality of antibodies an antibody that binds to the chimeric polypeptide, thereby purifying an antibody that specifically binds to the non-camelid antigen.

The plurality of camelid antibodies employed in the methods of the invention can be from any source. In certain embodiments, the plurality of camelid antibodies is obtained from the plasma of a camelid. The plasma can be from a naive (non-immunized) camelid or a camelid that has been immunized with the non-camelid antigen of interest. In one particular embodiment, the camelid has been immunized with a same chimeric polypeptide that is used for the selection or purification of the antibody. In other embodiments, the plurality of camelid antibodies are from a cell culture supernatant (e.g., a bacterial, yeast, or mammalian cell culture).

The plurality of camelid antibodies can be in any form or format that allows selection using the methods the methods. For example, the plurality of camelid antibodies can be part of an expression library, including without limitation, a phage display, nucleic acid display library, or yeast display library. Suitable libraries and methods for screening these libraries are well known in the art. See, for example, Antibody Engineering: Methods and Protocols. Methods in Molecular Biology Volume 248, (B.K.C. Lo, Ed) Humana Press, 2004 (ISBN: 1-58829-092-1), which is hereby incorporated by reference in its entirety.

Any chimeric polypeptide comprising a first portion derived from a camelid polypeptide and a second portion derived from non-camelid polypeptide homologue can be used to select antibodies in the methods of the invention. In a preferred embodiment, the chimeric polypeptide comprises a portion from a llama polypeptide and a portion from a human polypeptide homologue of the llama polypeptide (i.e., a llama-human chimera).

III. Epitope Mapping

The chimeric polypeptides disclosed herein are useful for epitope mapping of the binding site of a camelid antibody on a non-camelid antigen. As discussed above, camelid antibodies will not generally recognize the camelid portion of a camelid/non-camelid chimeric polypeptides of the invention. Thus if an antibody binds to a camelid/non-camelid chimeric polypeptide, it identifies the non-camelid portion of the region of the chimera as an epitope of that antibody.

Accordingly, in one aspect the invention provides a method for mapping the binding site of an antibody that specifically bids to a non-camelid antigen, the method generally involved: contacting the antibody with a plurality of chimeric polypeptides disclosed, wherein each polypeptide comprises a different portion of the human antigen; and identifying a chimeric polypeptide bound by the antibody, thereby mapping the binding site of the antibody.

Any chimeric polypeptide comprising a first portion derived from a camelid polypeptide and a second portion derived from non-camelid polypeptide homologue can be used to in the epitope mapping methods of the invention. In a preferred embodiment, the chimeric polypeptide comprises a portion from a llama polypeptide and a portion from a human polypeptide homologue of the llama polypeptide (i.e., a llama-human chimera).

Any art recognized assay for determining the binding of an antibody to an antigen can be used in the methods disclosed herein. Suitable methods include, without limitation ELISA and label free binding assays, such as Surface Plasmon Resonance (SPR).

D. Polynucleotides Encoding Chimeric Polypeptides

The invention also provides polynucleotide molecules encoding the polypeptides of the invention, expression vectors containing these nucleotide sequences operably linked to regulatory sequences which permit expression of the polypeptide in a host cell or cell-free expression system, and host cells or cell-free expression systems containing this expression vector.

Polynucleotide molecules encoding the polypeptides of the invention include, for example, recombinant DNA molecules. The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of a polypeptide according to the invention, recombinant polynucleotide encoding the various polypeptides may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/- DHFR (CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line (prokaryote or eukaryote). Whole human beings into which an expression vector encoding a polypeptide according to the invention has been introduced are explicitly excluded from the definition of a "host cell".

Incorporation by Reference

Various publications are cited in the foregoing description and throughout the following examples, each of which is incorporated by reference herein in its entirety.

EXAMPLES

The invention will be further understood with reference to the following non-limiting experimental examples.

Example 1

Human-llama Chimeric c-Met Fusion Proteins

Human-llama chimeric c-Met extracellular domain (ECD) fusion proteins were constructed by exchanging the IPT domain of human and llama c-Met in order to map the domain recognition of the mAbs. The construction was done using standard recombinant DNA and PCR methodologies. The llama and human c-Met were amplified from RNA converted to cDNA from peripheral blood lymphocytes (PBLs) from two donors of each species. The llama and human c-Met ECD (aa 25-932) were cloned into an eukaryote expression vector with a His tag for expression as soluble proteins by HEK293 cells. The IPT1-4 (aa 568-932) from llama was exchanged with the human IPT1-4 in the human c-Met and conversely the human IPT1-4 was exchanged with the llama IPT1-4 in the llama c-Met standard recombinant DNA and notably PCR methodologies. All four constructs, llama c-Met, llama/human-IPT, human c-Met, human/llama-IPT were expressed in HEK293 cells and purified using IMAC columns. FIG. 1 shows the alignment (88% identity) of human c-Met (Genbank X54559) with the *Llama glama* c-Met amplified from PBLs from two donors.

Example 2

Domain Mapping of mAbs Using Chimeric c-Met ECD

The binding sites of anti-c-Met antibodies 36C4, 13E6 and 48A2 were mapped using the chimeric c-Met proteins disclosed in Example 1. The 36C4 and 48A2 antibodies are fully disclosed elsewhere (see e.g., US 2012/0148607A1, which is hereby incorporated by reference in its entirety). Specifically, 200 ng of the different chimeric recombinant cMet proteins were immobilized on maxisorb plates overnight at 4° C. After washing with PBS, the plates were blocked with 1% casein for 2 h at RT, before the mAbs were added and allowed to bind to the c-Met for 1 h at RT. After washing, HRP-conjugated goat anti-human antibody (diluted 1/5000, Jackson Labs) was added and incubated for 1 h at RT before additional washing and addition of TMB. The optical density at 620 nm was read and the values were represented in a graph against the concentration of mAbs.

Figure 2B:
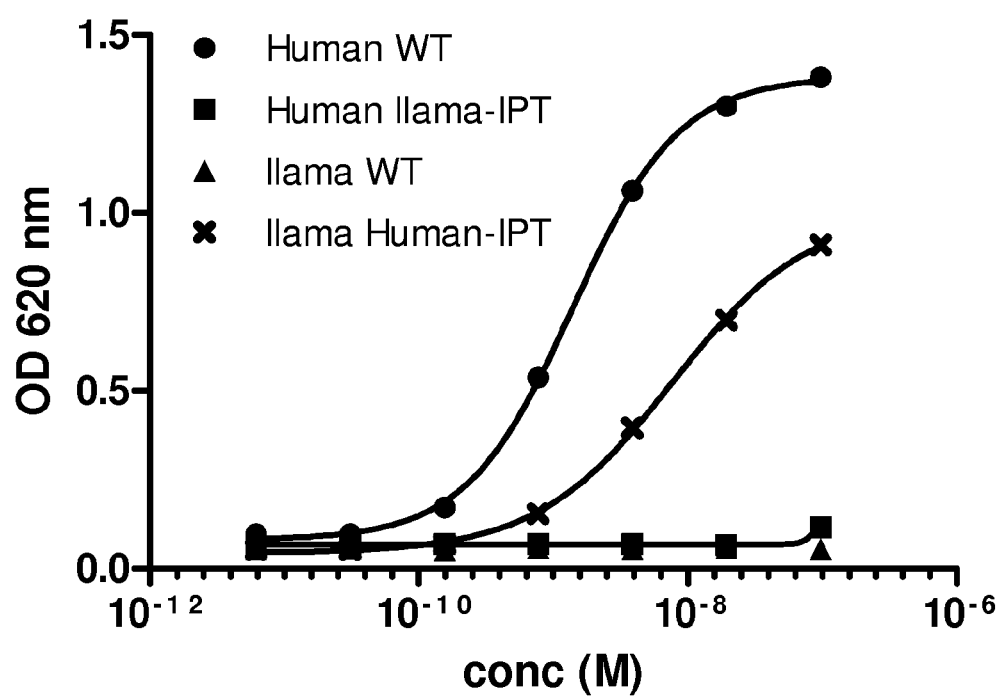

FIG. 2A shows binding of the 36C4 to the human c-Met (WT) and the human/llama IPT1-4 thus indicating binding to the SEMA-PSI region. FIG. 2B shows binding of mAb 13E6 to the human c-Met and to the llama/human IPT1-4. No binding was observed to the llama c-Met for any of the mAbs. 48A2 was also tested but mainly showed binding to the construct with the human SEMA-PSI and some binding to the construct with the human IPT, indicating that there was binding to an overlapping region in the PSI-IPT domains.

Example 3

Determination of c-Met Peptide Binding Sites of mAbs 36C4 and 48A2 Using Human-llama Chimeric c-Met To further define the amino acid (aa) stretches of c-Met to which the mAbs 36C4 and 48A2 bind, chimeric c-Met constructs containing approximately 20-300 aa exchanges from human to llama c-Met were prepared using PCR amplifications and ligations into the human c-Met containing vector with a Flag and a strep tag. FIG. 3A shows the chimeric c-Met constructs used for peptide mapping of 36C4 binding to the SEMA domain, whereas FIG. 3B shows the chimeric c-Met constructs for the peptide mapping of 48A2 binding to the PSI-IPT1 domain. The amino acid sequence of human and llama c-Met and the c-Met chimeras used in this study are set forth in Table 1, herein.

TABLE 1

Sequences of Llama-Human chimeric cMet

| Sequence name | Amino Acid Sequence | SEQ ID NO |
|---|---|---|
| Human c-MetECD | ECKEALAKSEMNVNMKYQLPNFTAETPIQNVILHEHHIFLGATNYIYVLNEE DLQKVAEYKTGPVLEHPDCFPCQDCSSKANLSGGVWKDNINMALVVDTYYDD QLISCGSVNRGTCQRHVFPHNHTADIQSEVHCIFSPQIEEPSQCPDCVVSAL GAKVLSSVKDRFINFFVGNTINSSYFPDHPLHSISVRRLKETKDGFMFLTDQ SYIDVLPEFRDSYPIKYVHAFESNNFIYFLTVQRETLDAQTFHTRIIRFCSI NSGLHSYMEMPLECILTEKRKKRSTKKEVFNILQAAYVSKPGAQLARQIGAS LNDDILFGVFAQSKPDSAEPMDRSAMCAFPIKYVNDFFNKIVNKNNVRCLQH FYGPNHEHCFNRTLLRNSSGCEARRDEYRTEFTTALQRVDLFMGQFSEVLLT SISTFIKGDLTIANLGTSEGREMQVVVSRSGPSTPHVNELLDSHPVSPEVIV EHTLNQNGYTLVITGKKITKIPLNGLGCRHFQSCSQCLSAPPFVQCGWCHDK CVRSEECLSGTWTQQICLPAIYKVFPNSAPLEGGTRLTICGWDEGFRRNNKF DLKKTRVLLGNESCTLTLSESTMNTLKCTVGPAMNKHFNMSIIISNGHGTTQ YSTFSYVDPVITSISPKYGPMAGGTLLTLTGNYLNSGNSRHISIGGKTCTLK SVSNSILECYTPAQTISTEFAVKLKIDLANRETSIFSYREDPIVYEIHPTKS FISGGSTITGVGKNLNSVSVPRMVINVHEAGRNFTVACQHRSNSEIICCTTP SLQQLNLQLPLKTKAFFMLDGILSKYFDLIYVHNPVFKPFEKPVMISMGNEN VLEIKGNDIDPEAVKGEVLKVGNKSCENIHLHSEAVLCTVPNDLLKLNSELN IEWKQAISSTVLGKVIVQPDQNFT | 1 |
| Llama glama c-MetECD | ECKEALVKSRMNVNMQYQLPNFTAETRIQNVVLHKHHIYLGAVNYIYVLNDKDLQKVA EYKTGPVLEHPHCFPCEDCSHKANLSDGVWKDNINMALLVDTYYDDQLISCGSVHRGT CQRHVLPPDNTADIQSEVYCMYSPQTDEEPGQCPDCVVSALGTKVLLSEKDRFINFFV GNTINSSYLPDHSLHSISVRRLKETQDGFKFLTDQSYIDVLPEFQDTYPIKYVHAFES NHFIYFLTVQRETLDAQTFHTRIIRFCSVDSGLHSYMEMPLECILTEKRRRSTKEEV FNILQAAYVSKPGSQLAKQIGANLNDDILYGVFAQSKPDSAEPMNRSAVCAFPVKYVN EFFNKIVNKNNVRCLQHFYGPNHEHCFNRTLLRNSSGCEVRNDEYRTEFTTALQRVDL FTGQFNQVLLTSISTFIKGDLTIANLGTSEGRFMQVVVSRSGLSTPHVNFLLDSHPVS PEAIVEHPLNQNGYTLVVTGKKITKIPLNGLGCEHFQSCSQCLSAPSFVQCGWCHDKC VQLEECSGGIWTQEICLPTIYKVLPTSAPLEGGTTLTICGWDFGFRRNNKSDLKKTKV FLGNESCTLTLSESTTNTLKCTVGPAMNEHFNVSIIISNNRGTAQYSTFSYVDPIITS ISPSYGPKTGGTLLTLTGKHLNSGNSRHISIGGKTCTLKSVSDSILECYTPAQTTPTE FPVKLKIDLANREINSFSYREDPVVYEIHPTKSFISGGSTITGVGKYLNSVSVLRMVI NVHEAGRNFTVACQHRSNSEIICCTTPSLQQLNLQLPVKTKAFFMLDGIHSKHFDLIY VHNPVFKPFEKPVMISIGNENVLEIKGNDIDPEAVKGEVLKVGNKSCENIHSHSEAVL CTVPNDLLKLNSELNIEWKQAVSSTVLGKVIVQPDQNFT | 2 |
| LS1 | ECKEALVKSRMNVNMQYQLPNFTAETRIQNVVLHKHHIYLGAVNYIYVLNDK DLQKVAEYKTGPVLEHPCFPCEDCSHKANLSDGVWKDNINMALLVDTYYDD QLISCGSVNRGTCQRHVFPHNHTADIQSEVHCIFSPQIEEPSQCPDCVVSAL GAKVLSSVKDRFINFFVGNTINSSYFPDHPLHSISVRRLKETKDGFMFLTDQ SYIDVLPEFRDSYPIKYVHAFESNNFIYFLTVQRETLDAQTFHTRIIRFCSI NSGLHSYMEMPLECILTEKRKKRSTKKEVFNILQAAYVSKPGAQLARQIGAS LNDDILFGVFAQSKPDSAEPMDRSAMCAFPIKYVNDFFNKIVNKNNVRCLQH FYGPNHEHCFNRTLLRNSSGCEARRDEYRTEFTTALQRVDLFMGQFSEVLLT SISTFIKGDLTIANLGTSEGRFMQVVVSRSGPSTPHVNFLLDSHPVSPEVIV EHTLNQNGYTLVITGKKITKIPLNGLGCRHFQSCSQCLSAPPFVQCGWCHDK CVRSEECLSGTWTQQICLPAIYKVFPNSAPLEGGTRLTICGWDFGFRRNNKF DLKKTRVLLGNESCTLTLSESTMNTLKCTVGPAMNKHFNMSIIISNGHGTTQ YSTFSYVDPVITSISPKYGPMAGGTLLTLTGNYLNSGNSRHISIGGKTCTLK SVSNSILECYTPAQTISTEFAVKLKIDLANRETSIFSYREDPIVYEIHPTKS | 3 |

TABLE 1-continued

Sequences of Llama-Human chimeric cMet

| Sequence name | Amino Acid Sequence | SEQ ID NO |
|---|---|---|
| | FISGGSTITGVGKNLNSVSVPRMVINVHEAGRNFTVACQHRSNSEIICCTTP SLQQLNLQLPLKTKAFFMLDGILSKYFDLIYVHNPVFKPFEKPVMISMGNEN VLEIKGNDIDPEAVKGEVLKVGNKSCENIHLHSEAVLCTVPNDLLKLNSELN IEWKQAISSTVLGKVIVQPDQNFT | |
| LS2 | ECKEALVKSRMNVNMQYQLPNFTAETRIQNVVLHKHHIYLGAVNYIYVLNDK DLQKVAEYKTGPVLEHPHCFPCEDCSHKANLSDGVWKDNINMALLVDTYYDD QLISCGSVHRGTCQRHVLPPDNTADIQSEVYCMYSPQTDEEPGQCPDCVVSA LGTKVLLSEKDRFINFFVGNTINSSYLPDHSLHSISVRRLKETQDGFMFLTD QSYIDVLPEFRDSYPIKYVHAFESNNFIYFLTVQRETLDAQTFHTRIIRFCS INSGLHSYMEMPLECILTEKRKKRSTKKEVFNILQAAYVSKPGAQLARQIGA SLNDDILFGVFAQSKPDSAEPMDRSAMCAFPIKYVNDFFNKIVNKNNVRCLQ HFYGPNEHCFNRTLLRNSSGCEARRDEYRTEFTTALQRVDLFMGQFSEVLL TSISTFIKGDLTIANLGTSEGRFMQVVVSRSGPSTPHVNFLLDSHPVSPEVI VEHTLNQNGYTLVITGKKITKIPLNGLGCRHFQSCSQCLSAPPFVQCGWCHD KCVRSEECLSGTWTQQICLPAIYKVFPNSAPLEGGTRLTICGWDFGFRRNNK FDLKKTRVLLGNESCTLTLSESTMNTLKCTVGPAMNKHFNMSIIISNGHGTT QYSTFSYVDPVITSISPKYGPMAGGTLLTLTGNYLNSGNSRHISIGGKTCTL KSVSNSILECYTPAQTISTEFAVKLKIDLANRETSIFSYREDPIVYEIHPTK SFISGGSTITGVGKNLNSVSVPRMVINVHEAGRNFTVACQHRSNSEIICCTT PSLQQLNLQLPLKTKAFFMLDGILSKYFDLIYVHNPVFKPFEKPVMISMGNE NVLEIKGNDIDPEAVKGEVLKVGNKSCENIHLHSEAVLCTVPNDLLKLNSEL NIEWKQAISSTVLGKVIVQPDQNFT | 4 |
| LS3 | ECKEALVKSRMNVNMQYQLPNFTAETRIQNVVLHKHHIYLGAVNYIYVLNDK DLQKVAEYKTGPVLEHPHCFPCEDCSHKANLSDGVWKDNINMALLVDTYYDD QLISCGSVHRGTCQRHVLPPDNTADIQSEVYCMYSPQTDEEPGQCPDCVVSA LGTKVLLSEKDRFINFFVGNTINSSYLPDHSLHSISVRRLKETQDGFKFLTD QSYIDVLPEFQDTYPIKYVHAFESNHFIYFLTVQRETLDAQTFHTRIIRFCS VDSGLHSYMEMPLECILTEKRRRRSTKEEVFNILQAAYVSKPGAQLARQIGA SLNDDILFGVFAQSKPDSAEPMDRSAMCAFPIKYVNDFFNKIVNKNNVRCLQ HFYGPNEHCFNRTLLRNSSGCEARRDEYRTEFTTALQRVDLFMGQFSEVLL TSISTFIKGDLTIANLGTSEGRFMQVVVSRSGPSTPHVNFLLDSHPVSPEVI VEHTLNQNGYTLVITGKKITKIPLNGLGCRHFQSCSQCLSAPPFVQCGWCHD KCVRSEECLSGTWTQQICLPAIYKVFPNSAPLEGGTRLTICGWDFGFRRNNK FDLKKTRVLLGNESCTLTLSESTMNTLKCTVGPAMNKHFNMSIIISNGHGTT QYSTFSYVDPVITSISPKYGPMAGGTLLTLTGNYLNSGNSRHISIGGKTCTL KSVSNSILECYTPAQTISTEFAVKLKIDLANRETSIFSYREDPIVYEIHPTK SFISGGSTITGVGKNLNSVSVPRMVINVHEAGRNFTVACQHRSNSEIICCTT PSLQQLNLQLPLKTKAFFMLDGILSKYFDLIYVHNPVFKPFEKPVMISMGNE NVLEIKGNDIDPEAVKGEVLKVGNKSCENIHLHSEAVLCTVPNDLLKLNSEL NIEWKQAISSTVLGKVIVQPDQNFT | 5 |
| LS4 | ECKEALVKSRMNVNMQYQLPNFTAETRIQNVVLHKHHIYLGAVNYIYVLNDK DLQKVAEYKTGPVLEHPHCFPCEDCSHKANLSDGVWKDNINMALLVDTYYDD QLISCGSVHRGTCQRHVLPPDNTADIQSEVYCMYSPQTDEEPGQCPDCVVSA LGTKVLLSEKDRFINFFVGNTINSSYLPDHSLHSISVRRLKETQDGFKFLTD QSYIDVLPEFQDTYPIKYVHAFESNHFIYFLTVQRETLDAQTFHTRIIRFCS VDSGLHSYMEMPLECILTEKRRRRSTKEEVFNILQAAYVSKPGSQLAKQIGA NLNDDILYGVFAQSKPDSAEPMNRSAVCAFPVKYVNEFFNKIVNKNNVRCLQ HFYGPNEHCFNRTLLRNSSGCEARRDEYRTEFTTALQRVDLFMGQFSEVLL TSISTFIKGDLTIANLGTSEGRFMQVVVSRSGPSTPHVNFLLDSHPVSPEVI VEHTLNQNGYTLVITGKKITKIPLNGLGCRHFQSCSQCLSAPPFVQCGWCHD KCVRSEECLSGTWTQQICLPAIYKVFPNSAPLEGGTRLTICGWDFGFRRNNK FDLKKTRVLLGNESCTLTLSESTMNTLKCTVGPAMNKHFNMSIIISNGHGTT QYSTFSYVDPVITSISPKYGPMAGGTLLTLTGNYLNSGNSRHISIGGKTCTL KSVSNSILECYTPAQTISTEFAVKLKIDLANRETSIFSYREDPIVYEIHPTK SFISGGSTITGVGKNLNSVSVPRMVINVHEAGRNFTVACQHRSNSEIICCTT PSLQQLNLQLPLKTKAFFMLDGILSKYFDLIYVHNPVFKPFEKPVMISMGNE NVLEIKGNDIDPEAVKGEVLKVGNKSCENIHLHSEAVLCTVPNDLLKLNSEL NIEWKQAISSTVLGKVIVQPDQNFT | 6 |
| LS5 | ECKEALVKSRMNVNMQYQLPNFTAETRIQNVVLHKHHIYLGAVNYIYVLNDK DLQKVAEYKTGPVLEHPHCFPCEDCSHKANLSDGVWKDNINMALLVDTYYDD QLISCGSVHRGTCQRHVLPPDNTADIQSEVYCMYSPQTDEEPGQCPDCVVSA LGTKVLLSEKDRFINFFVGNTINSSYLPDHSLHSISVRRLKETQDGFKFLTD QSYIDVLPEFQDTYPIKYVHAFESNHFIYFLTVQRETLDAQTFHTRIIRFCS VDSGLHSYMEMPLECILTEKRRRRSTKEEVFNILQAAYVSKPGSQLAKQIGA NLNDDILYGVFAQSKPDSAEPMNRSAVCAFPVKYVNEFFNKIVNKNNVRCLQ HFYGPNEHCFNRTLLRNSSGCEVRNDEYRTEFTTALQRVDLFMGQFNQVLL TSISTFIKGDLTIANLGTSEGRFMQVVVSRSGLSTPHVNFLLDSHPVSPEVI VEHTLNQNGYTLVITGKKITKIPLNGLGCRHFQSCSQCLSAPPFVQCGWCHD KCVRSEECLSGTWTQQICLPAIYKVFPNSAPLEGGTRLTICGWDFGFRRNNK FDLKKTRVLLGNESCTLTLSESTMNTLKCTVGPAMNKHFNMSIIISNGHGTT QYSTFSYVDPVITSISPKYGPMAGGTLLTLTGNYLNSGNSRHISIGGKTCTL | 7 |

TABLE 1-continued

Sequences of Llama-Human chimeric cMet

| Sequence name | Amino Acid Sequence | SEQ ID NO |
|---|---|---|
| | KSVSNSILECYTPAQTISTEFAVKLKIDLANRETSIFSYREDPIVYEIHPTK SFISGGSTITGVGKNLNSVSVPRMVINVHEAGRNFTVACQHRSNSEIICCTT PSLQQLNLQLPLKTKAFFMLDGILSKYFDLIYVHNPVFKPFEKPVMISMGNE NVLEIKGNDIDPEAVKGEVLKVGNKSCENIHLHSEAVLCTVPNDLLKLNSEL NIEWKQAISSTVLGKVIVQPDQNFT | |
| LP6 | ECKEALAKSEMNVNMKYQLPNFTAETPIQNVILHEHHIFLGATNYIYVLNEE DLQKVAEYKTGPVLEHPDCFPCQDCSSKANLSGGVWKDNINMALVVDTYYDD QLISCGSVNRGTCQRHVFPHNHTADIQSEVHCIFSPQIEEPSQCPDCVVSAL GAKVLSSVKDRFINFFVGNTINSSYFPDHPLHSISVRRLKETKDGFMFLTDQ SYIDVLPEFRDSYPIKYVHAFESNNFIYFLTVQRETLDAQTFHTRIIRFCSI NSGLHSYMEMPLECILTEKRKKRSTKKEVFNILQAAYVSKPGAQLARQIGAS LNDDILFGVFAQSKPDSAEPMDRSAMCAFPIKYVNDFFNKIVNKNNVRCLQH FYGPNHEHCFNRTLLRNSSGCEARRDEYRTEFTTALQRVDLFMGQFSEVLLT SISTFIKGDLTIANLGTSEGRFMQVVVSRSGPSTPHVNFLLDSHPVSPEVIV EHTLNQNGYTLVITGKKITKIPLNGLGCEHFQSCSQCLSAPSFVQCGWCHDK CVQLEECSGGIWTQEICLPTIYKVLPTSAPLEGGTTLTICGWDFGFRRNNKS DLKKTKVFLGNESCTLTLSESTTNTLKCTVGPAMNEHFNVSIIISNNRGTAQ YSTFSYVDPIITSISPSYGPKTGGTLLTLTGKHLNSGNSRHISIGGKTCTLK SVSDSILECYTPAQTTPTEFPVKLKIDLANREINSFSYREDPVVYEIHPTKS FISGGSTITGVGKYLNSVSVLRMVINVHEAGRNFTVACQHRSNSEIICCTTP SLQQLNLQLPVKTKAFFMLDGIHSKHFDLIYVHNPVFKPFEKPVMISIGNEN VLEIKGNDIDPEAVKGEVLKVGNKSCENIHSHSEAVLCTVPNDLLKLNSELN IEWKQAVSSTVLGKVIVQPDQNFT | 8 |
| LP7 | ECKEALAKSEMNVNMKYQLPNFTAETPIQNVILHEHHIFLGATNYIYVLNEE DLQKVAEYKTGPVLEHPDCFPCQDCSSKANLSGGVWKDNINMALVVDTYYDD QLISCGSVNRGTCQRHVFPHNHTADIQSEVHCIFSPQIEEPSQCPDCVVSAL GAKVLSSVKDRFINFFVGNTINSSYFPDHPLHSISVRRLKETKDGFMFLTDQ SYIDVLPEFRDSYPIKYVHAFESNNFIYFLTVQRETLDAQTFHTRIIRFCSI NSGLHSYMEMPLECILTEKRKKRSTKKEVFNILQAAYVSKPGAQLARQIGAS LNDDILFGVFAQSKPDSAEPMDRSAMCAFPIKYVNDFFNKIVNKNNVRCLQH FYGPNHEHCFNRTLLRNSSGCEARRDEYRTEFTTALQRVDLFMGQFSEVLLT SISTFIKGDLTIANLGTSEGRFMQVVVSRSGPSTPHVNFLLDSHPVSPEVIV EHTLNQNGYTLVITGKKITKIPLNGLGCRHFQSCSQCLSAPPFVQCGWCHDK CVQLEECSGGIWTQEICLPTIYKVLPTSAPLEGGTTLTICGWDFGFRRNNKS DLKKTKVFLGNESCTLTLSESTTNTLKCTVGPAMNEHFNVSIIISNNRGTAQ YSTFSYVDPIITSISPSYGPKTGGTLLTLTGKHLNSGNSRHISIGGKTCTLK SVSDSILECYTPAQTTPTEFPVKLKIDLANREINSFSYREDPVVYEIHPTKS FISGGSTIiGVGKYLNSVSVLRMVINVHEAGRNFTVACQHRSNSEIICCTTP SLQQLNLQLPVKTKAFFMLDGIHSKHFDLIYVHNPVFKPFEKPVMISIGNEN VLEIKGNDIDPEAVKGEVLKVGNKSCENIHSHSEAVLCTVPNDLLKLNSELN IEWKQAVSSTVLGKVIVQPDQNFT | 9 |
| L18 | CKEALAKSEMNVNMKYQLPNFTAETPIQNVILHEHHIFLGATNYIYVLNEED LQKVAEYKTGPVLEHPDCFPCQDCSSKANLSGGVWKDNINMALVVDTYYDQ LISCGSVNRGTCQRHVFPHNHTADIQSEVHCIFSPQIEEPSQCPDCVVSALG AKVLSSVKDRFINFFVGNTINSSYFPDHPLHSISVRRLKETKDGFMFLTDQS YIDVLPEFRDSYPIKYVHAFESNNFIYFLTVQRETLDAQTFHTRIIRFCSIN SGLHSYMEMPLECILTEKRKKRSTKKEVFNILQAAYVSKPGAQLARQIGASL NDDILFGVFAQSKPDSAEPMDRSAMCAFPIKYVNDFFNKIVNKNNVRCLQHF YGPNHEHCFNRTLLRNSSGCEARRDEYRTEFTTALQRVDLFMGQFSEVLLTS ISTFIKGDLTIANLGTSEGRFMQVVVSRSGPSTPHVNFLLDSHPVSPEVIVE HTLNQNGYTLVITGKKITKIPLNGLGCRHFQSCSQCLSAPPFVQCGWCHDKC VRSEECLSGTWTQQICLPTIYKVLPTSAPLEGGTTLTICGWDFGFRRNNKSD LKKTKVFLGNESCTLTLSESTTNTLKCTVGPAMNEHFNVSIIISNNRGTAQY STFSYVDPIITSISPSYGPKTGGTLLTLTGKHLNSGNSRHISIGGKTCTLKS VSDSILECYTPAQTTPTEFPVKLKIDLANREINSFSYREDPVVYEIHPTKSF ISGGSTITGVGKYLNSVSVLRMVINVHEAGRNFTVACQHRSNSEIICCTTPS LQQLNLQLPVKTKAFFMLDGIHSKHFDLIYVHNPVFKPFEKPVMISIGNENV LEIKGNDIDPEAVKGEVLKVGNKSCENIHSHSEAVLCTVPNDLLKLNSELNI EWKQAVSSTVLGKVIVQPDQNFT | 10 |
| L19 | ECKEALAKSEMNVNMKYQLPNFTAETPIQNVILHEHHIFLGATNYIYVLNEE DLQKVAEYKTGPVLEHPDCFPCQDCSSKANLSGGVWKDNINMALVVDTYYDD QLISCGSVNRGTCQRHVFPHNHTADIQSEVHCIFSPQIEEPSQCPDCVVSAL GAKVLSSVKDRFINFFVGNTINSSYFPDHPLHSISVRRLKETKDGFMFLTDQ SYIDVLPEFRDSYPIKYVHAFESNNFIYFLTVQRETLDAQTFHTRIIRFCSI NSGLHSYMEMPLECILTEKRKKRSTKKEVFNILQAAYVSKPGAQLARQIGAS LNDDILFGVFAQSKPDSAEPMDRSAMCAFPIKYVNDFFNKIVNKNNVRCLQH FYGPNHEHCFNRTLLRNSSGCEARRDEYRTEFTTALQRVDLFMGQFSEVLLT SISTFIKGDLTIANLGTSEGRFMQVVVSRSGPSTPHVNFLLDSHPVSPEVIV EHTLNQNGYTLVITGKKITKIPLNGLGCRHFQSCSQCLSAPPFVQCGWCHDK CVRSEECLSGTWTQQICLPAIYKVFPNSAPLEGGTRLTICGWDFGFRRNNKS DLKKTKVFLGNESCTLTLSESTTNTLKCTVGPAMNEHFNVSIIISNNRGTAQ | 11 |

TABLE 1-continued

Sequences of Llama-Human chimeric cMet

| Sequence name | Amino Acid Sequence | SEQ ID NO |
|---|---|---|
| | YSTFSYVDPIITSISPSYGPKTGGTLLTLTGKHLNSGNSRHISIGGKTCTLK<br>SVSDSILECYTPAQTTPTEFPVKLKIDLANREINSFSYREDPVVYEIHPTKS<br>FISGGSTITGVGKYLNSVSVLRMVINVHEAGRNFTVACQHRSNSEIICCTTP<br>SLQQLNLQLPVKTKAFFMLDGIHSKHFDLIYVHNPVFKPFEKPVMISIGNEN<br>VLEIKGNDIDPEAVKGEVLKVGNKSCENIHSHSEAVLCTVPNDLLKLNSELN<br>IEWKQAVSSTVLGKVIVQPDQNFT | |
| LI10 | ECKEALAKSEMNVNMKYQLPNFTAETPIQNVILHEHHIFLGATNYIYVLNEE<br>DLQKVAEYKTGPVLEHPDCFPCQDCSSKANLSGGVWKDNINMALVVDTYYDD<br>QLISCGSVNRGTCQRHVFPHNHTADIQSEVHCIFSPQIEEPSQCPDCVVSAL<br>GAKVLSSVKDRFINFFVGNTINSSYFPDHPLHSISVRRLKETKDGFMFLTDQ<br>SYIDVLPEFRDSYPIKYVHAFESNNFIYFLTVQRETLDAQTFHTRIIRFCSI<br>NSGLHSYMEMPLECILTEKRKKRSTKKEVFNILQAAYVSKPGAQLARQIGAS<br>LNDDILFGVFAQSKPDSAEPMDRSAMCAFPIKYVNDFFNKIVNKNNVRCLQH<br>FYGPNHEHCFNRTLLRNSSGCEARRDEYRTEFTTALQRVDLFMGQFSEVLLT<br>SISTFIKGDLTIANLGTSEGRFMQVVVSRSGPSTPHVNFLLDSHPVSPEVIV<br>EHTLNQNGYTLVITGKKITKIPLNGLGCRHFQSCSQCLSAPPFVQCGWCHDK<br>CVRSEECLSGTWTQQICLPAIYKVFPNSAPLEGGTRLTICGWDFGFRRNNKF<br>DLKKTRVLLGNESCTLTLSESTMNTLKCTVGPAMNEHFNVSIIISNNRGTAQ<br>YSTFSYVDPIITSISPSYGPKTGGTLLTLTGKHLNSGNSRHISIGGKTCTLK<br>SVSDSILECYTPAQTTPTEFPVKLKIDLANREINSFSYREDPVVYEIHPTKS<br>FISGGSTITGVGKYLNSVSVLRMVINVHEAGRNFTVACQHRSNSEIICCTTP<br>SLQQLNLQLPVKTKAFFMLDGIHSKHFDLIYVHNPVFKPFEKPVMISIGNEN<br>VLEIKGNDIDPEAVKGEVLKVGNKSCENIHSHSEAVLCTVPNDLLKLNSELN<br>IEWKQAVSSTVLGKVIVQPDQNFT | 12 |
| Li11 | ECKEALAKSEMNVNMKYQLPNFTAETPIQNVILHEHHIFLGATNYIYVLNEE<br>DLQKVAEYKTGPVLEHPDCFPCQDCSSKANLSGGVWKDNINMALVVDTYYDD<br>QLISCGSVNRGTCQRHVFPHNHTADIQSEVHCIFSPQIEEPSQCPDCVVSAL<br>GAKVLSSVKDRFINFFVGNTINSSYFPDHPLHSISVRRLKETKDGFMFLTDQ<br>SYIDVLPEFRDSYPIKYVHAFESNNFIYFLTVQRETLDAQTFHTRIIRFCSI<br>NSGLHSYMEMPLECILTEKRKKRSTKKEVFNILQAAYVSKPGAQLARQIGAS<br>LNDDILFGVFAQSKPDSAEPMDRSAMCAFPIKYVNDFFNKIVNKNNVRCLQH<br>FYGPNHEHCFNRTLLRNSSGCEARRDEYRTEFTTALQRVDLFMGQFSEVLLT<br>SISTFIKGDLTIANLGTSEGRFMQVVVSRSGPSTPHVNFLLDSHPVSPEVIV<br>EHTLNQNGYTLVITGKKITKIPLNGLGCRHFQSCSQCLSAPPFVQCGWCHDK<br>CVRSEECLSGTWTQQICLPAIYKVFPNSAPLEGGTRLTICGWDFGFRRNNKF<br>DLKKTRVLLGNESCTLTLSESTMNTLKCTVGPAMNKHFNMSIIISNGHGTTQ<br>YSTFSYVDPIITSISPSYGPKTGGTLLTLTGKHLNSGNSRHISIGGKTCTLK<br>SVSDSILECYTPAQTTPTEFPVKLKIDLANREINSFSYREDPVVYEIHPTKS<br>FISGGSTITGVGKYLNSVSVLRMVINVHEAGRNFTVACQHRSNSEIICCTTP<br>SLQQLNLQLPVKTKAFFMLDGIHSKHFDLIYVHNPVFKPFEKPVMISIGNEN<br>VLEIKGNDIDPEAVKGEVLKVGNKSCENIHSHSEAVLCTVPNDLLKLNSELN<br>IEWKQAVSSTVLGKVIVQPDQNFT | 13 |

The llama-human c-Met chimeras were produced in HEK293E cells and purified using strep-tactin sepharose HP (2-3 h at 11° C.) before washing of unbound proteins. The bound proteins were eluted with 2.5 mM desthiobiotin pH 8.2 and fractions of 1.5 ml were collected. Protein concentration was determined by Nanodrop. Protein was quality controlled by SDS-PAGE.

An ELISA was run to investigate the binding of the mAbs to the different chimeras. 2 µg/ml 36C4 or 48A2 were immobilized and, after blocking, the c-Met chimeras were added and revealed with 1/10,000 streptavidin-HRP (ELISA in Table 2).

Surface Plasmon Resonance (SPR) was also used to investigate the binding of the mAbs to the different llama-human c-Met chimeras. 3000 RU of 36C4, 48A2 and HGF were coupled on a CM-5 chip in 10 mM NaAc (pH4.5). 60 µl of a 10 µg/ml solution of the different c-Met chimeras was run over the chip at a flow rate of 30 µl/min and the association for 2 min was evaluated. The chip was regenerated with 20 mM NaOH and 1 M NaCl.

Table 2 shows the chimeras with the human c-Met and the amino acids (starting with aa E in the mature protein of the human c-Met) that were exchanged with the llama c-Met peptides and the binding results using Plasmon resonance and ELISA. The results were consistent and showed that 36C4 binding stops at aa 199, indicating a recognition site within aa 98-199 of human c-Met. This is the part of the SEMA domain that contains the HGF β-chain binding site, as shown in the crystal structure published by Stamos et al, (EMBO J, 2004).

The 48A2 mAb bound to aa 523-633 of human c-Met, which covers both part of the PSI and the IPT1 domains indicating recognition of a conformational epitope in both domains.

Western Blot with c-Met run under reducing conditions was used to investigate if 36C4 and 48A2 bound linear or conformational epitopes. No binding was observed for 36C4 or 48A2 indicating recognition of a conformational epitope (data not shown), which was confirmed with the chimeric c-Met proteins.

TABLE 2

Llama-human c-Met chimeras and binding results of 36C4 and 48A2 measured by SPR and ELISA

| Chimera | SPR | | | ELISA (EC$_{50}$ ng/ml) | |
|---|---|---|---|---|---|
| | HGF | 36C4 | 48A2 | 36C4 | 48A2 |
| LS1 (aa1-98) | + | + | + | 68 | 31 |
| LS2 (aa1-199) | + | − | + | — | 34 |
| LS3 (aa1-287) | + | − | + | — | 50 |
| LS4 (aa1-348) | + | − | + | — | 70 |
| LS5 (aa1-448) | + | − | + | — | 50 |
| LP6 (aa497-909) | + | + | − | 50 | — |
| LP7* (aa523-909) | + | + | − | 55 | — |
| LI8 (aa540-909) | + | + | +/− | 47 | >40 |
| LI9 (aa572-909) | + | + | +/− | 47 | >40 |
| LI10 (aa608-909) | + | + | +/− | 47 | >40 |
| LI11 (aa634-909) | + | + | + | 45 | 42 |
| LMet | + | − | − | — | — |
| HMet | + | + | + | 60 | 45 |

*T737I

The sequence of the human c-Met peptide recognized by mAb 36C4 (aa98-199) is as follows: VDTYYDDQLISCGSVNRGTCQRHVFPHNHTADIQSEVHCIFSPQIEEPSQCPDCVVSALGAKVLSSVKDRFINFFVGNTINSSYFPDHPLHSISVRRLKETK (SEQ ID NO:14)

The sequence of the human c-Met peptide recognized by mAb 48A2 (aa523-633) is as follows: RSEECLSGTWTQQICLPAIYKVFPNSAPLEGGTRLTICGWDFGFRRNNKFDLKKTRVLLGNESCTLTLSESTMNTLKCTVGPAMNKHFNMSIIISNGHGTTQYSTFSYVD P (SEQ ID NO:15)

Example 4

Figure 4:
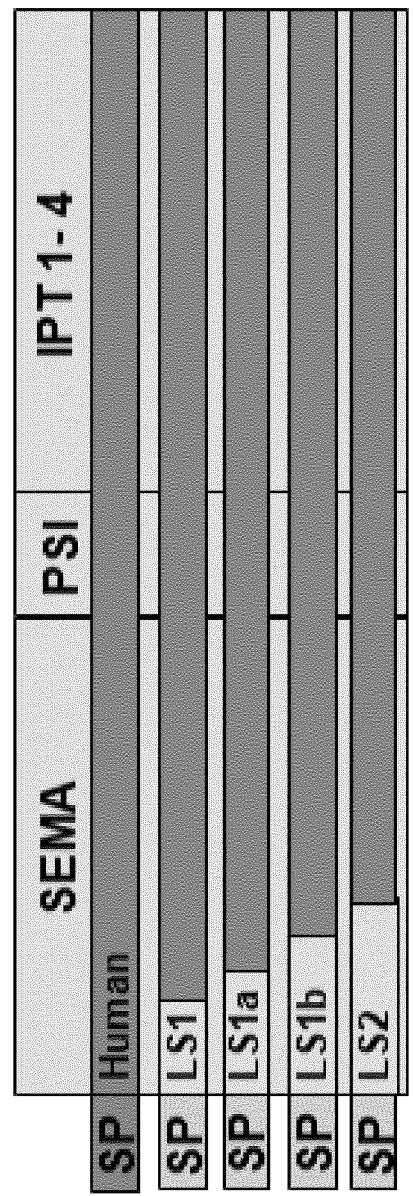
FIG. 4. Schematic illustration of the structure of chimeric llama-human c-Met constructs for fine mapping of antibody epitopes. Light grey shading indicates llama c-Met sequence (LS); dark grey shading indicates human c-Met sequence (hS). The relative positions of the signal sequence, SEMA domain, PSI domain and IPT domains are indicated.

Fine Mapping of Binding Sites of mAbs 36C4, 12A9, and 20F1 Using Human-llama Chimeric c-Met The binding site of anti-c-Met antibodies 36C4, 12A9 and 20F1 were mapped using additional chimeric c-Met proteins, using an ELISA-based method as set forth in Example 3, herein. The 36C4, 12A9 and 20F1 antibodies are fully described elsewhere (see e.g., US 2012/0148607A1, which is hereby incorporated by reference in its entirety). A schematic representation of the chimeric c-Met proteins used in this study is set forth in FIG. 4, herein. Specifically, based on the 36C4 epitope identified using the LS 1-5 SEMA chimeras (see FIG. 3A), new chimeric molecules were created that divide the human region between LS 1 and LS 2 into three parts, namely aa 99-132, aa 133-172 and aa 173-199. The results of ELISA binding experiments using anti-c-Met antibodies 36C4, 12A9 and 20F1 are set forth in Table 3, herein. These data show that the epitope of antibodies 20F1, 12A9 and 36C4 is between aa 133 and 172 of human c-Met.

TABLE 3

Binding of antibodies 36C4, 12A9 and 20F1 to c-Met chimeras as measured by ELISA

| | Human c-Met | llama c-Met | LS1 | LS1a | LS1b | LS2 |
|---|---|---|---|---|---|---|
| 36C4 | + | − | + | + | − | − |
| 12A9 | + | − | + | + | − | − |
| 20F1 | + | − | + | + | − | − |

+ indicate binding and − indicates no binding

Figure 5:
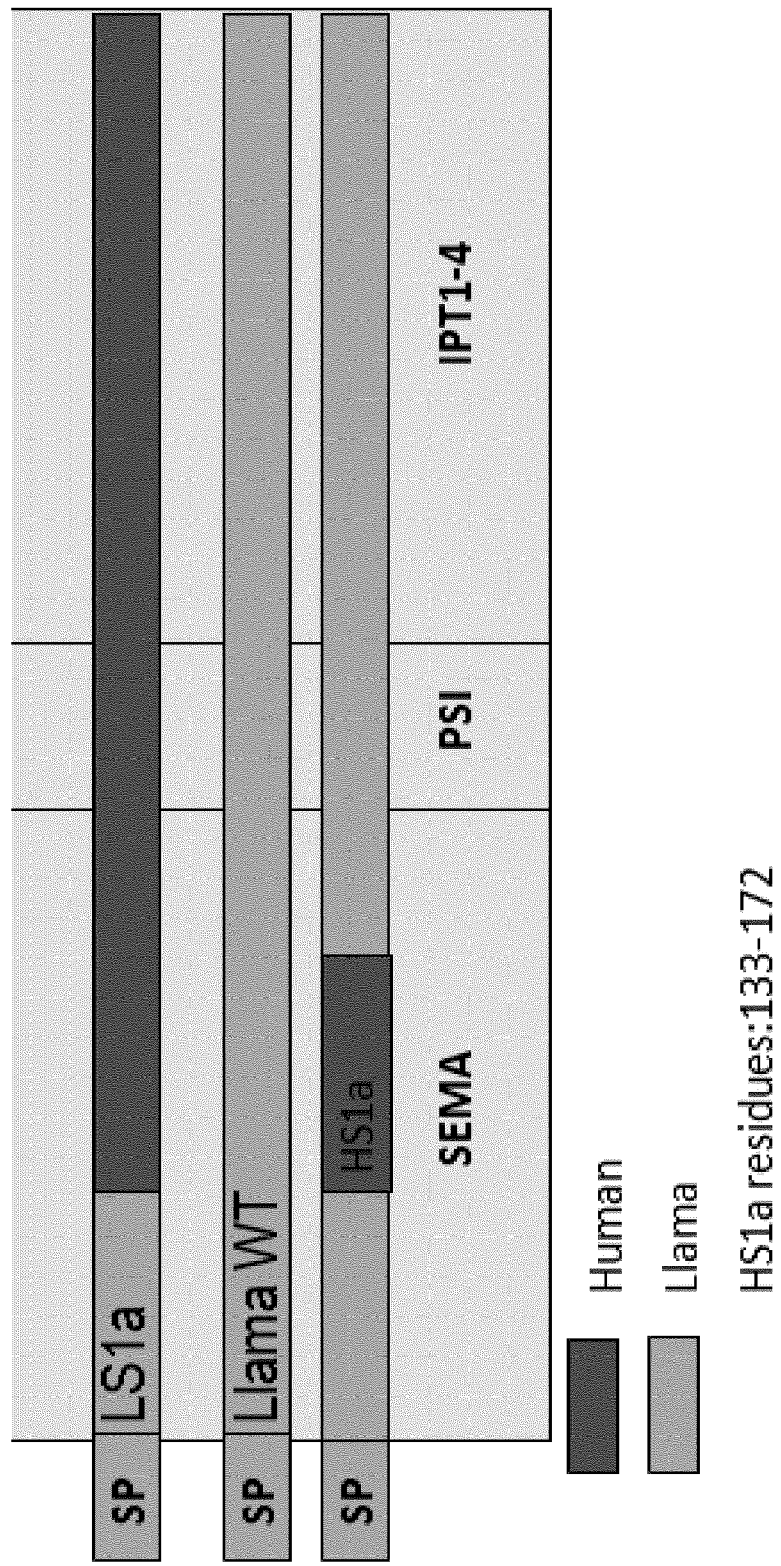
FIG. 5. Schematic illustration of the structure of chimeric llama-human c-Met constructs for fine mapping of antibody epitopes. Light grey shading indicates llama c-Met sequence (LS); dark grey shading indicates human c-Met sequence (hS). The relative positions of the signal sequence, SEMA domain, PSI domain and IPT domains are indicated.

To verify the epitope of antibodies 36C4, 12A9 and 20F1 determined above, a further c-Met chimera was produced in which residues 133-172 were human and all remaining residues were llama. A schematic representation of this chimeric c-Met protein (Hs1a) is set forth in FIG. 5, herein. The results of ELISA binding experiments measuring the binding of the Hs1a chimera to anti-c-Met antibodies 36C4, 12A9 and 20F1 are set forth in Table 4, herein. These data confirm that the epitope of antibodies 12A9 and 36C4 is between aa 133 and 172 of human c-Met. However, the epitope of 20F1 is not present in the Hs1a chimera.

TABLE 4

Binding of antibodies 36C4, 12A9 and 20F1 to c-Met chimeras as measured by ELISA

| mAb | Human c-Met | Llama c-Met | HS1a Chimera |
|---|---|---|---|
| 36C4 | + | − | + |
| 20F1 | + | − | − |
| 12A9 | + | − | + |

+ indicate binding and − indicates no binding

Figure 6:
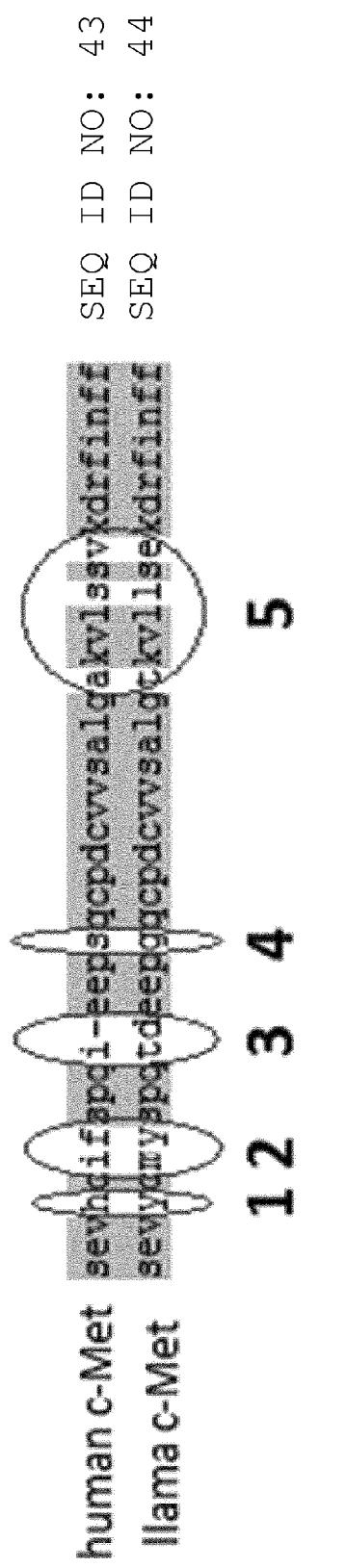
FIG. 6. Alignment of amino acids 132-172 of human and llama c-Met showing five regions of sequence divergence (circled).

The epitope of antibodies 36C4 and 12A9 was further mapped using point mutants of c-Met in which human residues were replaced by llama residues. From an alignment of aa 132-172 of human and llama c-Met, five regions of divergence were apparent (see FIG. 6). Four c-Met chimeras were generated (Mut 1, Mut 2, Mut 3, and Mut 4) in which the residues in each of the first four divergence regions of human c-Met (as indicated in FIG. 6) were independently mutated to the corresponding llama residue(s). The results of ELISA binding experiments measuring the binding of the c-Met chimeras Mut 1, Mut 2, Mut 3, and Mut 4 to anti-c-Met antibodies 36C4 and 12A9 are set forth in Table 5, herein. These data confirm that a major epitope of antibody 12A9 is between aa 141-149 and that a major epitope of antibody 36C4 is between aa 137-149.

TABLE 5

Binding of antibodies 36C4 and 12A9 to c-Met chimeras as measured by ELISA

| | 36C4 | 12A9 |
|---|---|---|
| Human Wt c-Met | + | + |
| Llama Wt | − | − |
| LS1a | + | + |
| Mut 1 | + | + |
| Mut 2 | − | + |
| Mut 3 | − | − |
| Mut 4 | − | − |
| LS 1b | − | − |

+ indicate binding and − indicates no binding

Example 5

Human-llama Chimeric CD70 Fusion Proteins

Figure 8:
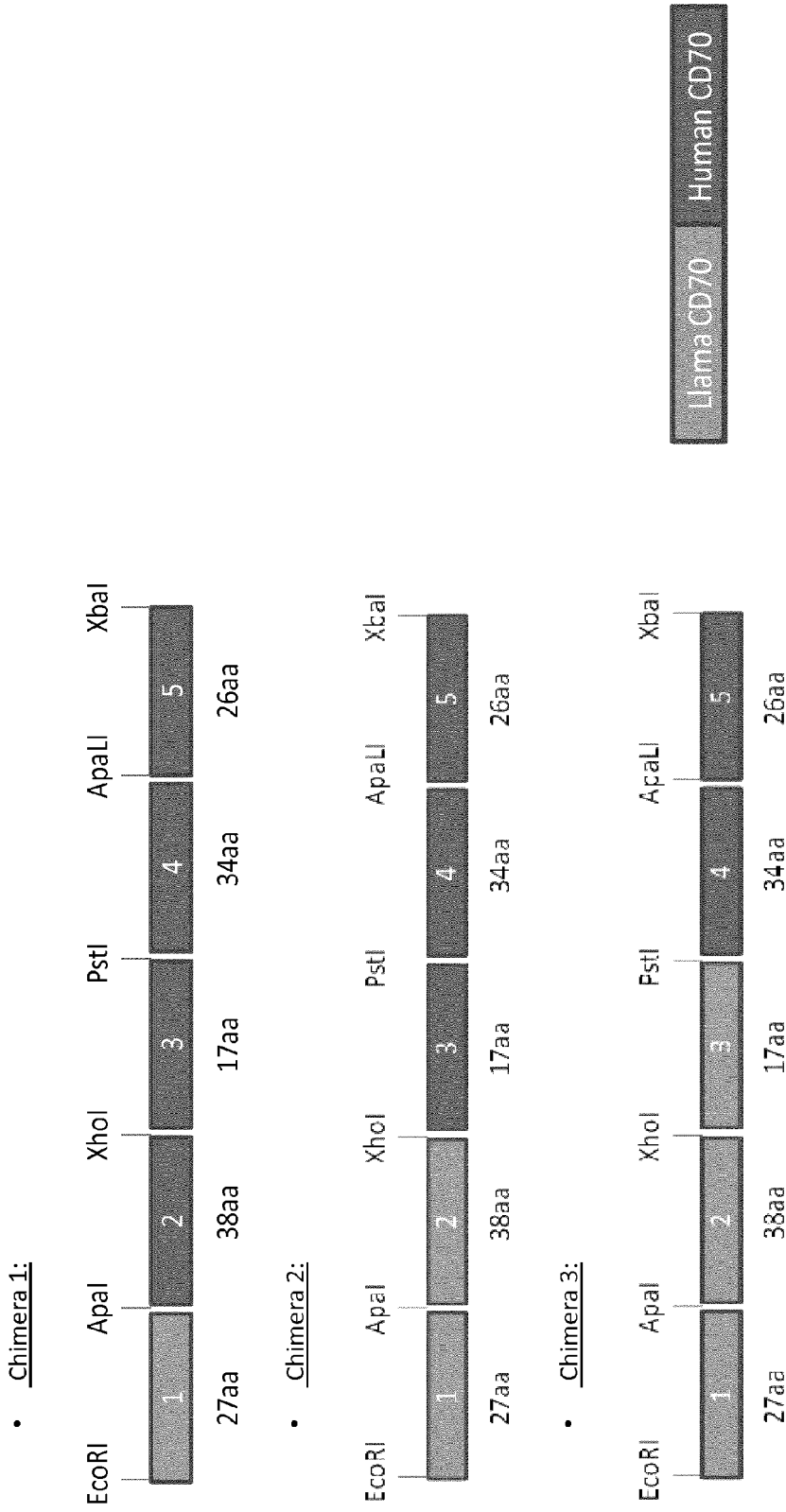
FIG. 8. Schematic illustration of the structure of exemplary llama-human CD70 chimeras.

Human-llama chimeric CD70 fusion proteins were constructed by exchanging the corresponding portions of human and llama CD70 extracellular domains. Chimera construction was done using standard recombinant DNA and PCR methodologies. The llama and human CD70 were amplified from RNA converted to cDNA from peripheral blood lymphocytes (PBLs) from donors of each species. The llama and human CD70 (aa 52-193) were cloned into a eukaryote expression vector with a flag and TNC tag for expression as soluble proteins by HEK293 cells. Corresponding regions of llama and human CD70 were exchanged using restriction site introduced in the cDNA. The restriction site were selected such that the amino acid sequence was not affected by the mutation in the cDNA. All chimeric constructs were expressed in HEK293 cells and purified (when required) using anti-flag antibody. FIG. 7 shows an alignment of the human CD70 ECD with the *Llama glama* CD70 ECD. Exemplary CD70 chimeras are set forth schematically in FIG. 8, herein. The amino acid sequences of the human-*Llama glama* CD70 chimeras depicted in FIG. 8 are set forth in Table 6, herein. An alignment of the CD70 chimeras is set forth in FIG. 9, herein.

combination of both immunizations and selections using chimeric GPCRs can be used. This approach can be used for any protein, soluble or membrane bound.

Example 7

Human-alpaca CXCR4 Chimeras

Human-alpaca chimeric CXCR4 fusion proteins are constructed by exchanging the corresponding portions of human and alpaca CXCR4. Both human CXCR4 isoform 1 and 2 were chimerized. Chimera construction is done using standard recombinant DNA and PCR methodologies. The alpaca and human CXCR4 are amplified from RNA converted to cDNA from peripheral blood lymphocytes (PBLs) from donors of each species. The alpaca and human CXCR4 are cloned into a eukaryote expression vector with or without an intracellular tag to monitor the expression and localization in mammalian cells (for example HEK293 or 3T3 cells). Corresponding regions of human and alpaca CXCR4 are exchanged using splicing and overlap extension PCR. All chimeric constructs are expressed in HEK293 cells. The cells can be used in their totality or partially (e.g. membrane fraction, solubilised membrane fraction, virosome etc. . . . ) or CXCR4 can be purified (after solubilisation and reconstitution) and purified. FIG. 11 shows the alignment of

TABLE 6

Amino acid sequences of human and llama CD70 ECD and exemplary human-llama CD70 ECD chimeras

| Sequence | Amino Acid Sequence | SEQ ID NO |
|---|---|---|
| Human CD70ECD | SLGWDVAELQLNHTGPQQDPRLYWQGGPALGRSFLHGPELDKGQLRIHRDGIYMVHIQ VTLAICSSTTASRHHPTTLAVGICSPASRSISLLRLSFHQGCTIASQRLTPLARGDTL CTNLTGTLLPSRNTDETFFGVQWVRP | 16 |
| Llama CD70ECD | WDLAELQLNHTGSRQDPRLRWQGGPALGRSFVHGPELDNGQLRVQRSGIYRLHIQLTL TNCSSTAGPHGATLTVGICSPAAHSISLLRLRFDRSCSVASQRLTPL | 17 |
| Chimera1 | SLGWDLAELQLNHTGSRQDPRLRWQGGPALGRSFLHGPELDKGQLRIHRDGIYMVHIQ VTLAICSSTTASRHHPTTLAVGICSPASRSISLLRLSFHQGCTIASQRLTPLARGDTL CTNLTGTLLPSRNTDETFFGVQWVRP | 18 |
| Chimera2 | SLGWDLAELQLNHTGSRQDPRLRWQGGPALGRSFVHGPELDNGQLRVQRSGIYRLHIQ LTLTNCSSTTASRHHPTTLAVGICSPASRSISLLRLSFHQGCTIASQRLTPLARGDTL CTNLTGTLLPSRNTDETFFGVQWVRP | 19 |
| Chimera3 | SLGWDLAELQLNHTGSRQDPRLRWQGGPALGRSFVHGPELDNGQLRVQRSGIYRLHIQ LTLTNCSSTAGPHGATLTVGICSPASRSISLLRLSFHQGCTIASQRLTPLARGDTLCT NLTGTLLPSRNTDETFFGVQWVRP | 20 |

Example 6

Human-llama G-protein Coupled Receptor (GPCR) Chimeras

Figure 10:
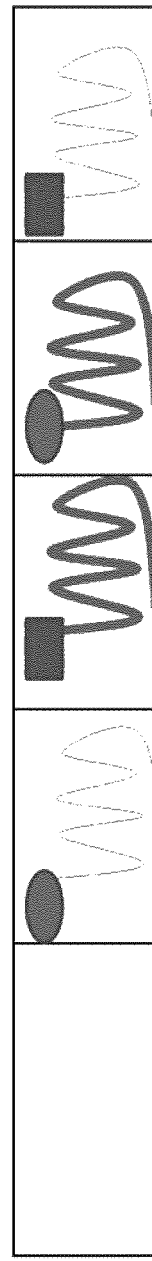
FIG. 10. Exemplary human llama G-protein coupled receptor (GPCR) chimeras

By making human/llama chimeric GPCRs, it is possible to favour the identification of antibodies binding to the human part of the receptor and this can be achieved in various ways (FIG. 10). For instance Llamas can be immunized with cells expressing a chimeric receptor (as an example llama N-terminal ECD fused to the human transmembrane/loop region), thereby skewing the immune response to the human part. Alternatively, if llamas are immunized with cells expressing the fully human GPCR, selections of Fabs can be performed with cell membranes derived from these cells, where the chimeric receptor will be skewing the selections to the human part. Of course, the human CXCR4 with the alpaca CXCR4. Exemplary CXCR4 human-alpaca chimeras are set forth in Table 7, herein. The amino acid sequences of exemplary CXCR4 human-alpaca chimeras are set forth in Table 8, herein.

TABLE 7

Exemplary human-alpaca CXCR4 chimeras

| Chimera | Residues from human CXCR4 | Residues from alpaca CXCR4 | Residues from human CXCR4 |
|---|---|---|---|
| hu1lla-CXCR4 | 1-47 | 44-356 | |
| hu2lla-CXCR4 | 1-43 | 44-356 | |
| llahu-CXCR4 | | 1-43 | 48-356 |

TABLE 8

Amino acid sequences of human and alpaca CXCR4 and exemplary human-alpaca CXCR4 chimeras

| Sequence | Amino Acid Sequence | SEQ ID NO |
|---|---|---|
| Alpaca CXCR4 | SIPLPLFQIFSSDNYTEDDLGSGDYDSIKEPCFQEENAHFNRVFLPTVYS IIFLTGIVGNGLVILVMGYQKKLRSMTDKYRLHLSVADLLFVLTLPFWAV DAVANWYFGKFLCKAVHVIYTVNLYSSVLILAFISLDRYLAIVHATNSQR PRKLLAEKVVYVGVWIPALLLTIPDFIFANVTEAEGRYICDRLYPSNLWM VVFHFQHIMVGLILPGIVILSCYCIIISKLSHSKGYQKRKALKTTVILIL AFFACWLPYYIGISIDCFILLEIIQQGCEFESIVHKWISITEALAFFHCC LNPILYAFLGAKFKTSAQHALTSVSRGSSLKILSKGKRGGHSSVSTESES SSFHSS | 21 |
| Human CXCR4 isoform1 | MEGISIYTSDNYTEEMGSGDYDSMKEPCFREENANFNKIFLPTIYSIIFL TGIVGNGLVILVMGYQKKLRSMTDKYRLHLSVADLLFVITLPFWAVDAVA NWYFGNFLCKAVHVIYTVNLYSSVLILAFISLDRYLAIVHATNSQRPRKL LAEKVVYVGVWIPALLLTIPDFIFANVSEADDRYICDRFYPNDLWVVVFQ FQHIMVGLILPGIVILSCYCIIISKLSHSKGHQKRKALKTTVILILAFFA CWLPYYIGISIDSFILLEIIKQGCEFENTVHKWISITEALAFFHCCLNPI LYAFLGAKFKTSAQHALTSVSRGSSLKILSKGKRGGHSSVSTESESSSFH SS | 22 |
| Human CXCR4 isoform2 | MSIPLPLLQIYTSDNYTEEMGSGDYDSMKEPCFREENANFNKIFLPTIYS IIFLTGIVGNGLVILVMGYQKKLRSMTDKYRLHLSVADLLFVITLPFWAV DAVANWYFGNFLCKAVHVIYTVNLYSSVLILAFISLDRYLAIVHATNSQR PRKLLAEKVVYVGVWIPALLLTIPDFIFANVSEADDRYICDRFYPNDLWV VVFQFQHIMVGLILPGIVILSCYCIIISKLSHSKGHQKRKALKTTVILIL AFFACWLPYYIGISIDSFILLEIIKQGCEFENTVHKWISITEALAFFHCC LNPILYAFLGAKFKTSAQHALTSVSRGSSLKILSKGKRGGHSSVSTESES SSFHSS | 23 |
| hu111a-cxcr4 | MEGISIYTSDNYTEEMGSGDYDSMKEPCFREENANFNKIFLPTVYSIIFL TGIVGNGLVILVMGYQKKLRSMTDKYRLHLSVADLLFVLTLPFWAVDAVA NWYFGKFLCKAVHVIYTVNLYSSVLILAFISLDRYLAIVHATNSQRPRKL LAEKVVYVGVWIPALLLTIPDFIFANVTEAEGRYICDRLYPSNLWMVVFH FQHIMVGLILPGIVILSCYCIIISKLSHSKGYQKRKALKTTVILILAFFA CWLPYYIGISIDCFILLEIIQQGCEFESIVHKWISITEALAFFHCCLNPI LYAFLGAKFKTSAQHALTSVSRGSSLKILSKGKRGGHSSVSTESESSSFH SS | 24 |
| hu211a-cxcr4 | MSIPLPLLQIYTSDNYTEEMGSGDYDSMKEPCFREENANFNKIFLPTVYS IIFLTGIVGNGLVILVMGYQKKLRSMTDKYRLHLSVADLLFVLTLPFWAV DAVANWYFGKFLCKAVHVIYTVNLYSSVLILAFISLDRYLAIVHATNSQR PRKLLAEKVVYVGVWIPALLLTIPDFIFANVTEAEGRYICDRLYPSNLWM VVFHFQHIMVGLILPGIVILSCYCIIISKLSHSKGYQKRKALKTTVILIL AFFACWLPYYIGISIDCFILLEIIQQGCEFESIVHKWISITEALAFFHCC LNPILYAFLGAKFKTSAQHALTSVSRGSSLKILSKGKRGGHSSVSTESES SSFHSS | 25 |
| 11ahu-cxcr4 | MSIPLPLFQIFSSDNYTEDDLGSGDYDSIKEPCFQEENAHFNRVFLPTIY SIIFLTGIVGNGLVILVMGYQKKLRSMTDKYRLHLSVADLLFVITLPFWA VDAVANWYFGNFLCKAVHVIYTVNLYSSVLILAFISLDRYLAIVHATNSQ RPRKLLAEKVVYVGVWIPALLLTIPDFIFANVSEADDRYICDRFYPNDLW VVVFQFQHIMVGLILPGIVILSCYCIIISKLSHSKGHQKRKALKTTVILI LAFFACWLPYYIGISIDSFILLEIIKQGCEFENTVHKWISITEALAFFHC CLNPILYAFLGAKFKTSAQHALTSVSRGSSLKILSKGKRGGHSSVSTESE SSSFHSS | 26 |

Example 8

Human-llama Chimeric IL-1Beta Fusion Proteins

Human-llama chimeric IL-1beta fusion proteins are constructed by exchanging the corresponding portions of human and llama IL-1beta. Chimera construction is done using standard recombinant DNA and PCR methodologies. The llama and human IL-1beta are amplified from RNA converted to cDNA from peripheral blood lymphocytes (PBLs) from donors of each species. The llama and human IL-1beta (aa 1-269) are cloned into a eukaryote expression vector with or without a tag (HIS tag for example) for expression as soluble proteins by eukaryotic cells (for example HEK293 cells) or prokaryotic cells (for example bacteria). Corresponding regions of llama and human IL-1beta are exchanged using splicing and overlap extension PCR. All chimeric constructs are expressed in HEK293 cells and purified (using IMAC columns in case the tag is a HIS tag). FIG. 12 shows the alignment of human IL-1beta with the llama IL-1beta. Exemplary IL-1beta chimeras are set forth in Table 9 and 10, herein. The amino acid sequences of the human-llama IL-1beta chimeras are set forth in Table 11, herein.

TABLE 9

Exemplary human-llama IL-1beta chimeras

| Chimera | Residues from human IL-1beta | Residues from llama IL-1beta |
|---|---|---|
| hulaIL1B-1 | 1-30 | 31-267 |
| hulaIL1B-2 | 1-59 | 61-267 |
| hulaIL1B-3 | 1-89 | 89-267 |
| hulaIL1B-4 | 1-119 | 118-267 |
| hulaIL1B-5 | 1-149 | 148-267 |
| hulaIL1B-6 | 1-179 | 178-267 |
| hulaIL1B-7 | 1-209 | 208-267 |
| hulaIL1B-8 | 1-239 | 238-267 |

TABLE 10

Exemplary human-llama IL-1beta chimeras

| Chimera | Residues from llama IL-1beta | Residues from human IL-1beta |
|---|---|---|
| LahuIL1B-11 | 1-30 | 31-269 |
| LahuIL1B-12 | 1-60 | 60-269 |
| LahuIL1B-13 | 1-88 | 90-269 |
| LahuIL1B-14 | 1-117 | 120-269 |
| L TABLE 11-continued Amino acid sequences of exemplary IL-1beta chimeras

| Chimera | Amino Acid Sequence | SEQ ID NO |
|---|---|---|
| hulaIL | MATVPEPTSEMMAYYSDNDNDLLFEADGPKQMKCSFQDLDLCPLDGGIQ LRISDHHYSKGFRQAASVVVAMDKLRKMLVPCPQTFQENDLSTFFPFIF EEEPIFFDTWDNEAYVHDAPVRSLNCTLRDSQQKSLVMSGPYELKALHL QGQDMEQQVVFSMSFVQGEESNDKIPVALGLKEKNLYLSCVLKDDKPTL QLESVDPKNYPKKKMEKRFVFNKIEINNKLEFESAQFPNWYISTSQAEN MPVFLGGTKGGQDITDFTMQFVSS | 35 |
| hulaIL1B-12 | MATVPEPTSEMMAYYSDNDNDLLFEADGPKQRKCCVQPPDLGSLGDEGI QLQISHQLYNKGFRQAASVVVAMDKLRKMLVPCPQTFQENDLSTFFPFI FEEEPIFFDTWDNEAYVHDAPVRSLNCTLRDSQQKSLVMSGPYELKALH LQGQDMEQQVVFSMSFVQGEESNDKIPVALGLKEKNLYLSCVLKDDKPT LQLESVDPKNYPKKKMEKRFVFNKIEINNKLEFESAQFPNWYISTSQAE NMPVFLGGTKGGQDITDFTMQFVSS | 36 |
| hulaIL1B-13 | MATVPEPTSEMMAYYSDNDNDLLFEADGPKQRKCCVQPPDLGSLGDEGI QLQISHQLYNKSFRQVVSLIVAMEKLSKCTYSQYFQDDDLSTFFPFIFE EEPIFFDTWDNEAYVHDAPVRSLNCTLRDSQQKSLVMSGPYELKALHLQ GQDMEQQVVFSMSFVQGEESNDKIPVALGLKEKNLYLSCVLKDDKPTLQ LESVDPKNYPKKKMEKRFVFNKIEINNKLEFESAQFPNWYISTSQAENM PVFLGGTKGGQDITDFTMQFVSS | 37 |
| hulaIL1B-14 | MATVPEPTSEMMAYYSDNDNDLLFEADGPKQRKCCVQPPDLGSLGDEGI QLQISHQLYNKSFRQVVSLIVAMEKLSKCTYSQYFQDDDLRNIFSLIFE EEPVTFETCADDFVCDAVVRSLNCTLRDSQQKSLVMSGPYELKALHLQG QDMEQQVVFSMSFVQGEESNDKIPVALGLKEKNLYLSCVLKDDKPTLQL ESVDPKNYPKKKMEKRFVFNKIEINNKLEFESAQFPNWYISTSQAENMP VFLGGTKGGQDITDFTMQFVSS | 38 |
| hulaIL1B-15 | MATVPEPTSEMMAYYSDNDNDLLFEADGPKQRKCCVQPPDLGSLGDEGI QLQISHQLYNKSFRQVVSLIVAMEKLSKCTYSQYFQDDDLRNIFSLIFE EEPVTFETCADDFVCDAVVQSLYCKLQDKEQKSMVLASPYVLQALHLLA QDMEQQVVFSMSFVQGEESNDKIPVALGLKEKNLYLSCVLKDDKPTLQL ESVDPKNYPKKKMEKRFVFNKIEINNKLEFESAQFPNWYISTSQAENMP VFLGGTKGGQDITDFTMQFVSS | 39 |
| hulaIL1B-16 | MATVPEPTSEMMAYYSDNDNDLLFEADGPKQRKCCVQPPDLGSLGDEGI QLQISHQLYNKSFRQVVSLIVAMEKLSKCTYSQYFQDDDLRNIFSLIFE EEPVTFETCADDFVCDAVVQSLYCKLQDKEQKSMVLASPYVLQALHLLA QDMSREVVFCMSFVQGDENNSKTPVVLGLKEKNLYLSCVLKDDKPTLQL ESVDPKNYPKKKMEKRFVFNKIEINNKLEFESAQFPNWYISTSQAENMP VFLGGTKGGQDITDFTMQFVSS | 40 |
| hulaIL1B-17 | MATVPEPTSEMMAYYSDNDNDLLFEADGPKQRKCCVQPPDLGSLGDEGI QLQISHQLYNKSFRQVVSLIVAMEKLSKCTYSQYFQDDDLRNIFSLIFE EEPVTFETCADDFVCDAVVQSLYCKLQDKEQKSMVLASPYVLQALHLLA QDMSREVVFCMSFVQGDENNSKTPVVLGLKEKNLYLSCVMKGDKPTLQL EALDPKSYPRKKMEKRFVFNKIEINNKLEFESAQFPNWYISTSQAENMP VFLGGTKGGQDITDFTMQFVSS | 41 |
| hulaIL1B-18 | MATVPEPTSEMMAYYSDNDNDLLFEADGPKQRKCCVQPPDLGSLGDEGI QLQISHQLYNKSFRQVVSLIVAMEKLSKCTYSQYFQDDDLRNIFSLIFE EEPVTFETCADDFVCDAVVQSLYCKLQDKEQKSMVLASPYVLQALHLLA QDMSREVVFCMSFVQGDENNSKTPVVLGLKEKNLYLSCVMKGDKPTLQL EALDPKSYPRKNMEKRFVFYKTEIKDRVEFESALYPNWYISTSTAEQRP VFLGQSRGGQDITDFTMETLSP | 42 |

Example 10

Selection of Antibodies from Phage Libraries Using Chimeric Human-llama c-Met Fusion Proteins To identify binders of the human IPT region of c-Met, phage libraries (produced from the immune repertoire of llamas immunized with human c-Met ECD) were screened using the LS2 c-Met chimera set forth in FIG. 3A. The phage libraries employed are fully described elsewhere (see e.g., US 2012/0148607A1, which is hereby incorporated by reference in its entirety). Briefly, eight llamas were immunized with the human gastric cell line MKN-45 over-expressing c-Met (DMSZ, ACC409)(c-Met over-expression was confirmed by Flow cytometry using PE conjugated anti-HGFR antibody (R&D systems, cat no FAB3582P)). Another two llamas were immunized with lung cancer cell line NCI-H441 cells. The llamas were immunized with intramuscular injections in the neck once per week for a period of six weeks. Approximately $10^7$ cells were injected into the neck muscles and Freund's incomplete adjuvant was injected in a second region located a few centimetres from the injection site of the cells. Immunization of llamas and harvesting of peripheral blood lymphocytes (PBLs), as well as the subsequent extraction of RNA and amplification of antibody fragments, were performed as described by De Haard and colleagues (De Haard et al., J Bacteriol. 187: 4531-41, 2005).

Blood samples of 10 ml were collected pre- and post-immunization to investigate the immune response. Three to four days after the last immunization, 400 ml blood was collected and total RNA extracted from PBLs prepared using a Ficoll-Paque gradient and the method described by Chomczynski P et al. (Anal. Biochem. 162: 156-159, 1987). The average RNA yield was 450 µg. The extracted RNA was then used for random cDNA synthesis and PCR amplification of the V-regions of the heavy and the light chains (VλX and Vκ) in order to construct the Fab-containing phagemid libraries as described by De Haard H, et al. (JBC. 18218-30, 1999).

Phage expressing Fabs were produced according to standard protocols and further selected on immobilized recombinant dimeric c-Met (R&D systems, 358-MT/CF) or recombinant extracellular domain of c-Met. Total elution of the c-Met binding phage with trypsin was performed according to standard phage display protocols.

Three rounds of selection were performed against the LS2 polypeptide to enrich for LS2-specific Fabs expressed by the phage. Individual colonies were isolated and periplasmic fractions were produced by IPTG induction from all the libraries according to standard protocols.

Screening of the c-Met-specific Fabs for competition with mature HGF for binding to immobilized c-Met was performed using an ELISA-based competition assay. 2 µg/ml of goat anti-human Fcγ antibody (Jackson) was immobilized on a maxisorb plate and, after blocking with 1% casein in PBS for 2 h, 100 ng/ml recombinant dimeric c-Met was added and incubated for 1 h at room temperature. After washing, 50 µl of the Fab containing peris was added and allowed to bind to the captured c-Met, before 25 ng/ml of N-terminally biotinylated mature HGF (R&D systems, 294-HGN/CF) was added. N-terminal biotinylation was performed according to protocol provided by Thermo Scientific with a 5-fold excess of NHS-LC biotin in a 50 mM phosphate buffer (pH 6.5) at 4° C. for 24 h. Biotinylated mature HGF was incubated at room temperature for 1 h before washing and addition of horseradish-conjugated streptavidin (strep-HRP) and incubated for an additional hour. TMB was added and the plate read at 620 nm. A non-relevant periplasmic extract and a 50-fold excess of cold (non-biotinylated) HGF was included as a positive control in all the plates.

The VH and the VL regions of HGF-competing clones were sequenced. The antibody clones identified in this screen were mostly antibody clones 20A11 and combinations of clones 13E6 and 2G2. These c-Met binding clones are all known to bind specifically to the IPT domain of human c-Met (see e.g., US 2012/0148607A1, which is hereby incorporated by reference in its entirety). Accordingly, these data clearly demonstrate that the llama-human chimeras of the invention can be used to select for antibodies that bind specifically to only the human portion of the chimera.

What is claimed is:

1. A method for generating a heterotetrameric camelid antibody against a conformational epitope of a non-camelid antigen, the method comprising
immunizing a camelid with a chimeric polypeptide comprising a first portion derived from a camelid polypeptide and a second portion derived from a non-camelid polypeptide homologue of the camelid polypeptide, wherein the chimeric polypeptide is a cell surface receptor, receptor ligand, or fragment thereof, and wherein the second portion of the chimeric polypeptide comprises the portion of the non-camelid antigen; and
isolating the heterotetrameric camelid antibody.

2. The method of claim 1, wherein the non-camelid antigen is a human antigen.

3. The method of claim 1, wherein the camelid being immunized is a llama.

4. The method of claim 1, wherein the camelid portion of the chimeric polypeptide is from the same species of camelid as the camelid being immunized.

5. The method of claim 1, wherein the camelid portion of the chimeric polypeptide is not immunogenic in the immunized camelid.

6. The method of claim 1, wherein the receptor ligand is a cytokine, chemokine, hormone, growth factor, or fragment thereof.

7. The method of claim 1, wherein the first portion and the second portion are derived from corresponding regions of the camelid polypeptide and the non-camelid polypeptide homologue.

8. The method of claim 1, wherein the first portion and the second portion are derived from non-corresponding regions of the camelid polypeptide and the non-camelid polypeptide homologue.

9. The method of claim 1, wherein the chimeric polypeptide is a chimeric c-Met, CD70, CXCR4, or IL-1beta polypeptide, or a fragment thereof.

10. The method of claim 1, wherein the chimeric polypeptide comprises the amino acid sequence selected from the group consisting of SEQ ID NOs 3-13.

11. The method of claim 1, wherein the camelid polypeptide is a llama polypeptide.

12. The method of claim 1, wherein the non-camelid polypeptide homologue is a human polypeptide homologue of the camelid polypeptide.

13. The method of claim 1, wherein the camelid polypeptide and the non-camelid polypeptide homologue are directly linked.

14. The method of claim 1, wherein the camelid polypeptide and the non-camelid polypeptide homologue are linked though an intervening linker moiety.

15. The method of claim 1, wherein the camelid polypeptide and the non-camelid polypeptide homologue are genetically linked.

16. The method of claim 1, wherein the camelid polypeptide and the non-camelid polypeptide homologue are chemically linked.

17. The method of claim 1, wherein the camelid polypeptide is a llama polypeptide, the non-camelid polypeptide homologue is a human polypeptide, and the chimeric polypeptide has a similar structural conformation to the llama or human polypeptide.

18. The method of claim 1, wherein the camelid polypeptide is a llama polypeptide, the non-camelid polypeptide homologue is a human polypeptide, and the chimeric polypeptide shares at least one functional property with the llama or human polypeptide.

* * * * *

```
                        SEQUENCE LISTING

<160> NUMBER OF SEQ ID NOS: 42

<210> SEQ ID NO 1
<211> LENGTH: 908
<212> TYPE: PRT
<213> ORGANISM: Artificial
<220> FEATURE:
<223> OTHER INFORMATION: Llama-Human chimeric cMET

<400> SEQUENCE: 1

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175
```

-continued

```
Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
        210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
            245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
            275                 280                 285

Val Phe Asn Ile Leu Gln Ala Ala Tyr Val Ser Lys Pro Gly Ala Gln
            290                 295                 300

Leu Ala Arg Gln Ile Gly Ala Ser Leu Asn Asp Ile Leu Phe Gly
305                 310                 315                 320

Val Phe Ala Gln Ser Lys Pro Asp Ser Ala Glu Pro Met Asp Arg Ser
            325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
            355                 360                 365

Asn His Glu His Cys Phe Asn Arg Thr Leu Leu Arg Asn Ser Ser Gly
            370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
            405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Val Ser Arg Ser Gly Pro
            435                 440                 445

Ser Thr Pro His Val Asn Phe Leu Leu Asp Ser His Pro Val Ser Pro
            450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
            485                 490                 495

Arg His Phe Gln Ser Cys Ser Gln Cys Leu Ser Ala Pro Pro Phe Val
            500                 505                 510

Gln Cys Gly Trp Cys His Asp Lys Cys Val Arg Ser Glu Glu Cys Leu
            515                 520                 525

Ser Gly Thr Trp Thr Gln Gln Ile Cys Leu Pro Ala Ile Tyr Lys Val
            530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
            565                 570                 575

Thr Arg Val Leu Leu Gly Asn Glu Ser Cys Thr Leu Thr Leu Ser Glu
            580                 585                 590

Ser Thr Met Asn Thr Leu Lys Cys Thr Val Gly Pro Ala Met Asn Lys
```

```
                    595                 600                 605
His Phe Asn Met Ser Ile Ile Ile Ser Asn Gly His Gly Thr Thr Gln
    610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
                645                 650                 655

Tyr Leu Asn Ser Gly Asn Ser Arg His Ile Ser Ile Gly Gly Lys Thr
            660                 665                 670

Cys Thr Leu Lys Ser Val Ser Asn Ser Ile Leu Glu Cys Tyr Thr Pro
        675                 680                 685

Ala Gln Thr Ile Ser Thr Glu Phe Ala Val Lys Leu Lys Ile Asp Leu
    690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
                725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
        755                 760                 765

Arg Ser Asn Ser Glu Ile Ile Cys Cys Thr Thr Pro Ser Leu Gln Gln
    770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
            820                 825                 830

Val Leu Glu Ile Lys Gly Asn Asp Ile Asp Pro Glu Ala Val Lys Gly
        835                 840                 845

Glu Val Leu Lys Val Gly Asn Lys Ser Cys Glu Asn Ile His Leu His
    850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr
            900                 905

<210> SEQ ID NO 2
<211> LENGTH: 909
<212> TYPE: PRT
<213> ORGANISM: Artificial
<220> FEATURE:
<223> OTHER INFORMATION: Llama-Human chimeric cMET

<400> SEQUENCE: 2

Glu Cys Lys Glu Ala Leu Val Lys Ser Arg Met Asn Val Asn Met Gln
1               5                   10                  15

Tyr Gln Leu Pro Asn Phe Thr Ala Glu Thr Arg Ile Gln Asn Val Val
            20                  25                  30

Leu His Lys His His Ile Tyr Leu Gly Ala Val Asn Tyr Ile Tyr Val
        35                  40                  45

Leu Asn Asp Lys Asp Leu Gln Lys Val Ala Glu Tyr Lys Thr Gly Pro
```

```
            50                  55                  60
Val Leu Glu His Pro His Cys Phe Pro Cys Glu Asp Cys Ser His Lys
 65                  70                  75                  80

Ala Asn Leu Ser Asp Gly Val Trp Lys Asp Asn Ile Asn Met Ala Leu
                     85                  90                  95

Leu Val Asp Thr Tyr Tyr Asp Asp Gln Leu Ile Ser Cys Gly Ser Val
                100                 105                 110

His Arg Gly Thr Cys Gln Arg His Val Leu Pro Pro Asp Asn Thr Ala
                115                 120                 125

Asp Ile Gln Ser Glu Val Tyr Cys Met Tyr Ser Pro Gln Thr Asp Glu
                130                 135                 140

Glu Pro Gly Gln Cys Pro Asp Cys Val Val Ser Ala Leu Gly Thr Lys
145                 150                 155                 160

Val Leu Leu Ser Glu Lys Asp Arg Phe Ile Asn Phe Val Gly Asn
                165                 170                 175

Thr Ile Asn Ser Ser Tyr Leu Pro Asp His Ser Leu His Ser Ile Ser
                180                 185                 190

Val Arg Arg Leu Lys Glu Thr Gln Asp Gly Phe Lys Phe Leu Thr Asp
                195                 200                 205

Gln Ser Tyr Ile Asp Val Leu Pro Glu Phe Gln Asp Thr Tyr Pro Ile
210                 215                 220

Lys Tyr Val His Ala Phe Glu Ser Asn His Phe Ile Tyr Phe Leu Thr
225                 230                 235                 240

Val Gln Arg Glu Thr Leu Asp Ala Gln Thr Phe His Thr Arg Ile Ile
                245                 250                 255

Arg Phe Cys Ser Val Asp Ser Gly Leu His Ser Tyr Met Glu Met Pro
                260                 265                 270

Leu Glu Cys Ile Leu Thr Glu Lys Arg Arg Arg Ser Thr Lys Glu
                275                 280                 285

Glu Val Phe Asn Ile Leu Gln Ala Ala Tyr Val Ser Lys Pro Gly Ser
                290                 295                 300

Gln Leu Ala Lys Gln Ile Gly Ala Asn Leu Asn Asp Asp Ile Leu Tyr
305                 310                 315                 320

Gly Val Phe Ala Gln Ser Lys Pro Asp Ser Ala Glu Pro Met Asn Arg
                325                 330                 335

Ser Ala Val Cys Ala Phe Pro Val Lys Tyr Val Asn Glu Phe Phe Asn
                340                 345                 350

Lys Ile Val Asn Lys Asn Asn Val Arg Cys Leu Gln His Phe Tyr Gly
                355                 360                 365

Pro Asn His Glu His Cys Phe Asn Arg Thr Leu Leu Arg Asn Ser Ser
370                 375                 380

Gly Cys Glu Val Arg Asn Asp Glu Tyr Arg Thr Glu Phe Thr Thr Ala
385                 390                 395                 400

Leu Gln Arg Val Asp Leu Phe Thr Gly Gln Phe Asn Gln Val Leu Leu
                405                 410                 415

Thr Ser Ile Ser Thr Phe Ile Lys Gly Asp Leu Thr Ile Ala Asn Leu
                420                 425                 430

Gly Thr Ser Glu Gly Arg Phe Met Gln Val Val Ser Arg Ser Gly
                435                 440                 445

Leu Ser Thr Pro His Val Asn Phe Leu Leu Asp Ser His Pro Val Ser
                450                 455                 460

Pro Glu Ala Ile Val Glu His Pro Leu Asn Gln Asn Gly Tyr Thr Leu
465                 470                 475                 480
```

```
Val Val Thr Gly Lys Lys Ile Thr Lys Ile Pro Leu Asn Gly Leu Gly
            485                 490                 495

Cys Glu His Phe Gln Ser Cys Ser Gln Cys Leu Ser Ala Pro Ser Phe
            500                 505                 510

Val Gln Cys Gly Trp Cys His Asp Lys Cys Val Gln Leu Glu Glu Cys
            515                 520                 525

Ser Gly Gly Ile Trp Thr Gln Glu Ile Cys Leu Pro Thr Ile Tyr Lys
            530                 535                 540

Val Leu Pro Thr Ser Ala Pro Leu Glu Gly Gly Thr Thr Leu Thr Ile
545                 550                 555                 560

Cys Gly Trp Asp Phe Gly Phe Arg Arg Asn Asn Lys Ser Asp Leu Lys
            565                 570                 575

Lys Thr Lys Val Phe Leu Gly Asn Glu Ser Cys Thr Leu Thr Leu Ser
            580                 585                 590

Glu Ser Thr Thr Asn Thr Leu Lys Cys Thr Val Gly Pro Ala Met Asn
            595                 600                 605

Glu His Phe Asn Val Ser Ile Ile Ile Ser Asn Asn Arg Gly Thr Ala
            610                 615                 620

Gln Tyr Ser Thr Phe Ser Tyr Val Asp Pro Ile Ile Thr Ser Ile Ser
625                 630                 635                 640

Pro Ser Tyr Gly Pro Lys Thr Gly Gly Thr Leu Leu Thr Leu Thr Gly
            645                 650                 655

Lys His Leu Asn Ser Gly Asn Ser Arg His Ile Ser Ile Gly Gly Lys
            660                 665                 670

Thr Cys Thr Leu Lys Ser Val Ser Asp Ser Ile Leu Glu Cys Tyr Thr
            675                 680                 685

Pro Ala Gln Thr Thr Pro Thr Glu Phe Pro Val Lys Leu Lys Ile Asp
            690                 695                 700

Leu Ala Asn Arg Glu Ile Asn Ser Phe Ser Tyr Arg Glu Asp Pro Val
705                 710                 715                 720

Val Tyr Glu Ile His Pro Thr Lys Ser Phe Ile Ser Gly Gly Ser Thr
            725                 730                 735

Ile Thr Gly Val Gly Lys Tyr Leu Asn Ser Val Ser Val Leu Arg Met
            740                 745                 750

Val Ile Asn Val His Glu Ala Gly Arg Asn Phe Thr Val Ala Cys Gln
            755                 760                 765

His Arg Ser Asn Ser Glu Ile Ile Cys Cys Thr Thr Pro Ser Leu Gln
            770                 775                 780

Gln Leu Asn Leu Gln Leu Pro Val Lys Thr Lys Ala Phe Phe Met Leu
785                 790                 795                 800

Asp Gly Ile His Ser Lys His Phe Asp Leu Ile Tyr Val His Asn Pro
            805                 810                 815

Val Phe Lys Pro Phe Glu Lys Pro Val Met Ile Ser Ile Gly Asn Glu
            820                 825                 830

Asn Val Leu Glu Ile Lys Gly Asn Asp Ile Asp Pro Glu Ala Val Lys
            835                 840                 845

Gly Glu Val Leu Lys Val Gly Asn Lys Ser Cys Glu Asn Ile His Ser
            850                 855                 860

His Ser Glu Ala Val Leu Cys Thr Val Pro Asn Asp Leu Leu Lys Leu
865                 870                 875                 880

Asn Ser Glu Leu Asn Ile Glu Trp Lys Gln Ala Val Ser Ser Thr Val
            885                 890                 895
```

-continued

Leu Gly Lys Val Ile Val Gln Pro Asp Gln Asn Phe Thr
                900                 905

<210> SEQ ID NO 3
<211> LENGTH: 908
<212> TYPE: PRT
<213> ORGANISM: Artificial
<220> FEATURE:
<223> OTHER INFORMATION: Llama-Human chimeric cMET

<400> SEQUENCE: 3

Glu Cys Lys Glu Ala Leu Val Lys Ser Arg Met Asn Val Asn Met Gln
1               5                   10                  15

Tyr Gln Leu Pro Asn Phe Thr Ala Glu Thr Arg Ile Gln Asn Val Val
            20                  25                  30

Leu His Lys His His Ile Tyr Leu Gly Ala Val Asn Tyr Ile Tyr Val
        35                  40                  45

Leu Asn Asp Lys Asp Leu Gln Lys Val Ala Glu Tyr Lys Thr Gly Pro
    50                  55                  60

Val Leu Glu His Pro His Cys Phe Pro Cys Glu Asp Cys Ser His Lys
65                  70                  75                  80

Ala Asn Leu Ser Asp Gly Val Trp Lys Asp Asn Ile Asn Met Ala Leu
                85                  90                  95

Leu Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
        275                 280                 285

Val Phe Asn Ile Leu Gln Ala Ala Tyr Val Ser Lys Pro Gly Ala Gln
    290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

-continued

Ile Val Asn Lys Asn Val Arg Cys Leu Gln His Phe Tyr Gly Pro
            355                 360                 365

Asn His Glu His Cys Phe Asn Arg Thr Leu Leu Arg Asn Ser Ser Gly
        370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Ser Arg Ser Gly Pro
        435                 440                 445

Ser Thr Pro His Val Asn Phe Leu Leu Asp Ser His Pro Val Ser Pro
        450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
            500                 505                 510

Gln Cys Gly Trp Cys His Asp Lys Cys Val Arg Ser Glu Glu Cys Leu
        515                 520                 525

Ser Gly Thr Trp Thr Gln Gln Ile Cys Leu Pro Ala Ile Tyr Lys Val
        530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
                565                 570                 575

Thr Arg Val Leu Leu Gly Asn Glu Ser Cys Thr Leu Thr Leu Ser Glu
            580                 585                 590

Ser Thr Met Asn Thr Leu Lys Cys Thr Val Gly Pro Ala Met Asn Lys
        595                 600                 605

His Phe Asn Met Ser Ile Ile Ile Ser Asn Gly His Gly Thr Thr Gln
        610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
                645                 650                 655

Tyr Leu Asn Ser Gly Asn Ser Arg His Ile Ser Ile Gly Gly Lys Thr
            660                 665                 670

Cys Thr Leu Lys Ser Val Ser Asn Ser Ile Leu Glu Cys Tyr Thr Pro
        675                 680                 685

Ala Gln Thr Ile Ser Thr Glu Phe Ala Val Lys Leu Lys Ile Asp Leu
        690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
                725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
        755                 760                 765

Arg Ser Asn Ser Glu Ile Ile Cys Cys Thr Thr Pro Ser Leu Gln Gln

```
                    770                 775                 780
Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
                820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Leu His
            850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr
                900                 905

<210> SEQ ID NO 4
<211> LENGTH: 909
<212> TYPE: PRT
<213> ORGANISM: Artificial
<220> FEATURE:
<223> OTHER INFORMATION: Llama-Human chimeric cMET

<400> SEQUENCE: 4

Glu Cys Lys Glu Ala Leu Val Lys Ser Arg Met Asn Val Asn Met Gln
1               5                   10                  15

Tyr Gln Leu Pro Asn Phe Thr Ala Glu Thr Arg Ile Gln Asn Val Val
                20                  25                  30

Leu His Lys His His Ile Tyr Leu Gly Ala Val Asn Tyr Ile Tyr Val
            35                  40                  45

Leu Asn Asp Lys Asp Leu Gln Lys Val Ala Glu Tyr Lys Thr Gly Pro
    50                  55                  60

Val Leu Glu His Pro His Cys Phe Pro Cys Glu Asp Cys Ser His Lys
65                  70                  75                  80

Ala Asn Leu Ser Asp Gly Val Trp Lys Asp Asn Ile Asn Met Ala Leu
                85                  90                  95

Leu Val Asp Thr Tyr Tyr Asp Asp Gln Leu Ile Ser Cys Gly Ser Val
                100                 105                 110

His Arg Gly Thr Cys Gln Arg His Val Leu Pro Pro Asp Asn Thr Ala
            115                 120                 125

Asp Ile Gln Ser Glu Val Tyr Cys Met Tyr Ser Pro Gln Thr Asp Glu
    130                 135                 140

Glu Pro Gly Gln Cys Pro Asp Cys Val Val Ser Ala Leu Gly Thr Lys
145                 150                 155                 160

Val Leu Leu Ser Glu Lys Asp Arg Phe Ile Asn Phe Phe Val Gly Asn
                165                 170                 175

Thr Ile Asn Ser Ser Tyr Leu Pro Asp His Ser Leu His Ser Ile Ser
                180                 185                 190

Val Arg Arg Leu Lys Glu Thr Gln Asp Gly Phe Met Phe Leu Thr Asp
            195                 200                 205

Gln Ser Tyr Ile Asp Val Leu Pro Glu Phe Arg Asp Ser Tyr Pro Ile
    210                 215                 220

Lys Tyr Val His Ala Phe Glu Ser Asn Asn Phe Ile Tyr Phe Leu Thr
```

```
            225                 230                 235                 240
Val Gln Arg Glu Thr Leu Asp Ala Gln Thr Phe His Thr Arg Ile Ile
                245                 250                 255
Arg Phe Cys Ser Ile Asn Ser Gly Leu His Ser Tyr Met Glu Met Pro
                260                 265                 270
Leu Glu Cys Ile Leu Thr Glu Lys Arg Lys Arg Ser Thr Lys Lys
                275                 280                 285
Glu Val Phe Asn Ile Leu Gln Ala Ala Tyr Val Ser Lys Pro Gly Ala
                290                 295                 300
Gln Leu Ala Arg Gln Ile Gly Ala Ser Leu Asn Asp Ile Leu Phe
305                 310                 315                 320
Gly Val Phe Ala Gln Ser Lys Pro Asp Ser Ala Glu Pro Met Asp Arg
                325                 330                 335
Ser Ala Met Cys Ala Phe Pro Ile Lys Tyr Val Asn Asp Phe Phe Asn
                340                 345                 350
Lys Ile Val Asn Lys Asn Asn Val Arg Cys Leu Gln His Phe Tyr Gly
                355                 360                 365
Pro Asn His Glu His Cys Phe Asn Arg Thr Leu Leu Arg Asn Ser Ser
                370                 375                 380
Gly Cys Glu Ala Arg Arg Asp Glu Tyr Arg Thr Glu Phe Thr Thr Ala
385                 390                 395                 400
Leu Gln Arg Val Asp Leu Phe Met Gly Gln Phe Ser Glu Val Leu Leu
                405                 410                 415
Thr Ser Ile Ser Thr Phe Ile Lys Gly Asp Leu Thr Ile Ala Asn Leu
                420                 425                 430
Gly Thr Ser Glu Gly Arg Phe Met Gln Val Val Ser Arg Ser Gly
                435                 440                 445
Pro Ser Thr Pro His Val Asn Phe Leu Leu Asp Ser His Pro Val Ser
                450                 455                 460
Pro Glu Val Ile Val Glu His Thr Leu Asn Gln Asn Gly Tyr Thr Leu
465                 470                 475                 480
Val Ile Thr Gly Lys Lys Ile Thr Lys Ile Pro Leu Asn Gly Leu Gly
                485                 490                 495
Cys Arg His Phe Gln Ser Cys Ser Gln Cys Leu Ser Ala Pro Pro Phe
                500                 505                 510
Val Gln Cys Gly Trp Cys His Asp Lys Cys Val Arg Ser Glu Glu Cys
                515                 520                 525
Leu Ser Gly Thr Trp Thr Gln Gln Ile Cys Leu Pro Ala Ile Tyr Lys
                530                 535                 540
Val Phe Pro Asn Ser Ala Pro Leu Glu Gly Gly Thr Arg Leu Thr Ile
545                 550                 555                 560
Cys Gly Trp Asp Phe Gly Phe Arg Arg Asn Asn Lys Phe Asp Leu Lys
                565                 570                 575
Lys Thr Arg Val Leu Leu Gly Asn Glu Ser Cys Thr Leu Thr Leu Ser
                580                 585                 590
Glu Ser Thr Met Asn Thr Leu Lys Cys Thr Val Gly Pro Ala Met Asn
                595                 600                 605
Lys His Phe Asn Met Ser Ile Ile Ile Ser Asn Gly His Gly Thr Thr
                610                 615                 620
Gln Tyr Ser Thr Phe Ser Tyr Val Asp Pro Val Ile Thr Ser Ile Ser
625                 630                 635                 640
Pro Lys Tyr Gly Pro Met Ala Gly Gly Thr Leu Leu Thr Leu Thr Gly
                645                 650                 655
```

```
Asn Tyr Leu Asn Ser Gly Asn Ser Arg His Ile Ser Ile Gly Gly Lys
            660                 665                 670

Thr Cys Thr Leu Lys Ser Val Ser Asn Ser Ile Leu Glu Cys Tyr Thr
        675                 680                 685

Pro Ala Gln Thr Ile Ser Thr Glu Phe Ala Val Lys Leu Lys Ile Asp
    690                 695                 700

Leu Ala Asn Arg Glu Thr Ser Ile Phe Ser Tyr Arg Glu Asp Pro Ile
705                 710                 715                 720

Val Tyr Glu Ile His Pro Thr Lys Ser Phe Ile Ser Gly Gly Ser Thr
                725                 730                 735

Ile Thr Gly Val Gly Lys Asn Leu Asn Ser Val Ser Val Pro Arg Met
            740                 745                 750

Val Ile Asn Val His Glu Ala Gly Arg Asn Phe Thr Val Ala Cys Gln
        755                 760                 765

His Arg Ser Asn Ser Glu Ile Ile Cys Cys Thr Thr Pro Ser Leu Gln
    770                 775                 780

Gln Leu Asn Leu Gln Leu Pro Leu Lys Thr Lys Ala Phe Phe Met Leu
785                 790                 795                 800

Asp Gly Ile Leu Ser Lys Tyr Phe Asp Leu Ile Tyr Val His Asn Pro
                805                 810                 815

Val Phe Lys Pro Phe Glu Lys Pro Val Met Ile Ser Met Gly Asn Glu
            820                 825                 830

Asn Val Leu Glu Ile Lys Gly Asn Asp Ile Asp Pro Glu Ala Val Lys
        835                 840                 845

Gly Glu Val Leu Lys Val Gly Asn Lys Ser Cys Glu Asn Ile His Leu
    850                 855                 860

His Ser Glu Ala Val Leu Cys Thr Val Pro Asn Asp Leu Leu Lys Leu
865                 870                 875                 880

Asn Ser Glu Leu Asn Ile Glu Trp Lys Gln Ala Ile Ser Ser Thr Val
                885                 890                 895

Leu Gly Lys Val Ile Val Gln Pro Asp Gln Asn Phe Thr
            900                 905

<210> SEQ ID NO 5
<211> LENGTH: 909
<212> TYPE: PRT
<213> ORGANISM: Artificial
<220> FEATURE:
<223> OTHER INFORMATION: Llama-Human chimeric cMET

<400> SEQUENCE: 5

Glu Cys Lys Glu Ala Leu Val Lys Ser Arg Met Asn Val Asn Met Gln
1               5                   10                  15

Tyr Gln Leu Pro Asn Phe Thr Ala Glu Thr Arg Ile Gln Asn Val Val
            20                  25                  30

Leu His Lys His His Ile Tyr Leu Gly Ala Val Asn Tyr Ile Tyr Val
        35                  40                  45

Leu Asn Asp Lys Asp Leu Gln Lys Val Ala Glu Tyr Lys Thr Gly Pro
    50                  55                  60

Val Leu Glu His Pro His Cys Phe Pro Cys Glu Asp Cys Ser His Lys
65                  70                  75                  80

Ala Asn Leu Ser Asp Gly Val Trp Lys Asp Asn Ile Asn Met Ala Leu
                85                  90                  95

Leu Val Asp Thr Tyr Tyr Asp Asp Gln Leu Ile Ser Cys Gly Ser Val
            100                 105                 110
```

```
His Arg Gly Thr Cys Gln Arg His Val Leu Pro Pro Asp Asn Thr Ala
        115                 120                 125

Asp Ile Gln Ser Glu Val Tyr Cys Met Tyr Ser Pro Gln Thr Asp Glu
        130                 135                 140

Glu Pro Gly Gln Cys Pro Asp Cys Val Val Ser Ala Leu Gly Thr Lys
145                 150                 155                 160

Val Leu Leu Ser Glu Lys Asp Arg Phe Ile Asn Phe Val Gly Asn
                165                 170                 175

Thr Ile Asn Ser Ser Tyr Leu Pro Asp His Ser Leu His Ser Ile Ser
                180                 185                 190

Val Arg Arg Leu Lys Glu Thr Gln Asp Gly Phe Lys Phe Leu Thr Asp
        195                 200                 205

Gln Ser Tyr Ile Asp Val Leu Pro Glu Phe Gln Asp Thr Tyr Pro Ile
        210                 215                 220

Lys Tyr Val His Ala Phe Glu Ser Asn His Phe Ile Tyr Phe Leu Thr
225                 230                 235                 240

Val Gln Arg Glu Thr Leu Asp Ala Gln Thr Phe His Thr Arg Ile Ile
                245                 250                 255

Arg Phe Cys Ser Val Asp Ser Gly Leu His Ser Tyr Met Glu Met Pro
        260                 265                 270

Leu Glu Cys Ile Leu Thr Glu Lys Arg Arg Arg Ser Thr Lys Glu
        275                 280                 285

Glu Val Phe Asn Ile Leu Gln Ala Ala Tyr Val Ser Lys Pro Gly Ala
        290                 295                 300

Gln Leu Ala Arg Gln Ile Gly Ala Ser Leu Asn Asp Ile Leu Phe
305                 310                 315                 320

Gly Val Phe Ala Gln Ser Lys Pro Asp Ser Ala Glu Pro Met Asp Arg
                325                 330                 335

Ser Ala Met Cys Ala Phe Pro Ile Lys Tyr Val Asn Asp Phe Phe Asn
                340                 345                 350

Lys Ile Val Asn Lys Asn Asn Val Arg Cys Leu Gln His Phe Tyr Gly
        355                 360                 365

Pro Asn His Glu His Cys Phe Asn Arg Thr Leu Leu Arg Asn Ser Ser
        370                 375                 380

Gly Cys Glu Ala Arg Arg Asp Glu Tyr Arg Thr Glu Phe Thr Thr Ala
385                 390                 395                 400

Leu Gln Arg Val Asp Leu Phe Met Gly Gln Phe Ser Glu Val Leu Leu
                405                 410                 415

Thr Ser Ile Ser Thr Phe Ile Lys Gly Asp Leu Thr Ile Ala Asn Leu
                420                 425                 430

Gly Thr Ser Glu Gly Arg Phe Met Gln Val Val Ser Arg Ser Gly
        435                 440                 445

Pro Ser Thr Pro His Val Asn Phe Leu Leu Asp Ser His Pro Val Ser
450                 455                 460

Pro Glu Val Ile Val Glu His Thr Leu Asn Gln Asn Gly Tyr Thr Leu
465                 470                 475                 480

Val Ile Thr Gly Lys Lys Ile Thr Lys Ile Pro Leu Asn Gly Leu Gly
                485                 490                 495

Cys Arg His Phe Gln Ser Cys Ser Gln Cys Leu Ser Ala Pro Pro Phe
                500                 505                 510

Val Gln Cys Gly Trp Cys His Asp Lys Cys Val Arg Ser Glu Glu Cys
        515                 520                 525
```

Leu Ser Gly Thr Trp Thr Gln Gln Ile Cys Leu Pro Ala Ile Tyr Lys
    530             535                 540

Val Phe Pro Asn Ser Ala Pro Leu Glu Gly Gly Thr Arg Leu Thr Ile
545                 550                 555                 560

Cys Gly Trp Asp Phe Gly Phe Arg Arg Asn Asn Lys Phe Asp Leu Lys
                565                 570                 575

Lys Thr Arg Val Leu Leu Gly Asn Glu Ser Cys Thr Leu Thr Leu Ser
            580                 585                 590

Glu Ser Thr Met Asn Thr Leu Lys Cys Thr Val Gly Pro Ala Met Asn
        595                 600                 605

Lys His Phe Asn Met Ser Ile Ile Ser Asn Gly His Gly Thr Thr
    610                 615                 620

Gln Tyr Ser Thr Phe Ser Tyr Val Asp Pro Val Ile Thr Ser Ile Ser
625                 630                 635                 640

Pro Lys Tyr Gly Pro Met Ala Gly Gly Thr Leu Leu Thr Leu Thr Gly
                645                 650                 655

Asn Tyr Leu Asn Ser Gly Asn Ser Arg His Ile Ser Ile Gly Gly Lys
            660                 665                 670

Thr Cys Thr Leu Lys Ser Val Ser Asn Ser Ile Leu Glu Cys Tyr Thr
        675                 680                 685

Pro Ala Gln Thr Ile Ser Thr Glu Phe Ala Val Lys Leu Lys Ile Asp
    690                 695                 700

Leu Ala Asn Arg Glu Thr Ser Ile Phe Ser Tyr Arg Glu Asp Pro Ile
705                 710                 715                 720

Val Tyr Glu Ile His Pro Thr Lys Ser Phe Ile Ser Gly Gly Ser Thr
                725                 730                 735

Ile Thr Gly Val Gly Lys Asn Leu Asn Ser Val Ser Val Pro Arg Met
            740                 745                 750

Val Ile Asn Val His Glu Ala Gly Arg Asn Phe Thr Val Ala Cys Gln
        755                 760                 765

His Arg Ser Asn Ser Glu Ile Ile Cys Cys Thr Thr Pro Ser Leu Gln
    770                 775                 780

Gln Leu Asn Leu Gln Leu Pro Leu Lys Thr Lys Ala Phe Phe Met Leu
785                 790                 795                 800

Asp Gly Ile Leu Ser Lys Tyr Phe Asp Leu Ile Tyr Val His Asn Pro
                805                 810                 815

Val Phe Lys Pro Phe Glu Lys Pro Val Met Ile Ser Met Gly Asn Glu
            820                 825                 830

Asn Val Leu Glu Ile Lys Gly Asn Asp Ile Asp Pro Glu Ala Val Lys
        835                 840                 845

Gly Glu Val Leu Lys Val Gly Asn Lys Ser Cys Glu Asn Ile His Leu
    850                 855                 860

His Ser Glu Ala Val Leu Cys Thr Val Pro Asn Asp Leu Leu Lys Leu
865                 870                 875                 880

Asn Ser Glu Leu Asn Ile Glu Trp Lys Gln Ala Ile Ser Ser Thr Val
                885                 890                 895

Leu Gly Lys Val Ile Val Gln Pro Asp Gln Asn Phe Thr
            900                 905

<210> SEQ ID NO 6
<211> LENGTH: 909
<212> TYPE: PRT
<213> ORGANISM: Artificial
<220> FEATURE:
<223> OTHER INFORMATION: Llama-Human chimeric cMET

<400> SEQUENCE: 6

Glu Cys Lys Glu Ala Leu Val Lys Ser Arg Met Asn Val Asn Met Gln
1               5                   10                  15

Tyr Gln Leu Pro Asn Phe Thr Ala Glu Thr Arg Ile Gln Asn Val Val
            20                  25                  30

Leu His Lys His His Ile Tyr Leu Gly Ala Val Asn Tyr Ile Tyr Val
        35                  40                  45

Leu Asn Asp Lys Asp Leu Gln Lys Val Ala Glu Tyr Lys Thr Gly Pro
    50                  55                  60

Val Leu Glu His Pro His Cys Phe Pro Cys Glu Asp Cys Ser His Lys
65                  70                  75                  80

Ala Asn Leu Ser Asp Gly Val Trp Lys Asp Asn Ile Asn Met Ala Leu
                85                  90                  95

Leu Val Asp Thr Tyr Tyr Asp Asp Gln Leu Ile Ser Cys Gly Ser Val
            100                 105                 110

His Arg Gly Thr Cys Gln Arg His Val Leu Pro Pro Asp Asn Thr Ala
        115                 120                 125

Asp Ile Gln Ser Glu Val Tyr Cys Met Tyr Ser Pro Gln Thr Asp Glu
    130                 135                 140

Glu Pro Gly Gln Cys Pro Asp Cys Val Val Ser Ala Leu Gly Thr Lys
145                 150                 155                 160

Val Leu Leu Ser Glu Lys Asp Arg Phe Ile Asn Phe Phe Val Gly Asn
                165                 170                 175

Thr Ile Asn Ser Ser Tyr Leu Pro Asp His Ser Leu His Ser Ile Ser
            180                 185                 190

Val Arg Arg Leu Lys Glu Thr Gln Asp Gly Phe Lys Phe Leu Thr Asp
        195                 200                 205

Gln Ser Tyr Ile Asp Val Leu Pro Glu Phe Gln Asp Thr Tyr Pro Ile
    210                 215                 220

Lys Tyr Val His Ala Phe Glu Ser Asn His Phe Ile Tyr Phe Leu Thr
225                 230                 235                 240

Val Gln Arg Glu Thr Leu Asp Ala Gln Thr Phe His Thr Arg Ile Ile
                245                 250                 255

Arg Phe Cys Ser Val Asp Ser Gly Leu His Ser Tyr Met Glu Met Pro
            260                 265                 270

Leu Glu Cys Ile Leu Thr Glu Lys Arg Arg Arg Ser Thr Lys Glu
        275                 280                 285

Glu Val Phe Asn Ile Leu Gln Ala Ala Tyr Val Ser Lys Pro Gly Ser
    290                 295                 300

Gln Leu Ala Lys Gln Ile Gly Ala Asn Leu Asn Asp Asp Ile Leu Tyr
305                 310                 315                 320

Gly Val Phe Ala Gln Ser Lys Pro Asp Ser Ala Glu Pro Met Asn Arg
                325                 330                 335

Ser Ala Val Cys Ala Phe Pro Lys Tyr Val Asn Glu Phe Phe Asn
            340                 345                 350

Lys Ile Val Asn Lys Asn Asn Val Arg Cys Leu Gln His Phe Tyr Gly
        355                 360                 365

Pro Asn His Glu His Cys Phe Asn Arg Thr Leu Leu Arg Asn Ser Ser
    370                 375                 380

Gly Cys Glu Ala Arg Arg Asp Glu Tyr Arg Thr Glu Phe Thr Thr Ala
385                 390                 395                 400

Leu Gln Arg Val Asp Leu Phe Met Gly Gln Phe Ser Glu Val Leu Leu

```
            405                 410                 415
Thr Ser Ile Ser Thr Phe Ile Lys Gly Asp Leu Thr Ile Ala Asn Leu
            420                 425                 430

Gly Thr Ser Glu Gly Arg Phe Met Gln Val Val Ser Arg Ser Gly
            435                 440                 445

Pro Ser Thr Pro His Val Asn Phe Leu Leu Asp Ser His Pro Val Ser
            450                 455                 460

Pro Glu Val Ile Val Glu His Thr Leu Asn Gln Asn Gly Tyr Thr Leu
465                 470                 475                 480

Val Ile Thr Gly Lys Lys Ile Thr Lys Ile Pro Leu Asn Gly Leu Gly
                    485                 490                 495

Cys Arg His Phe Gln Ser Cys Ser Gln Cys Leu Ser Ala Pro Pro Phe
                    500                 505                 510

Val Gln Cys Gly Trp Cys His Asp Lys Cys Val Arg Ser Glu Glu Cys
                    515                 520                 525

Leu Ser Gly Thr Trp Thr Gln Gln Ile Cys Leu Pro Ala Ile Tyr Lys
                    530                 535                 540

Val Phe Pro Asn Ser Ala Pro Leu Glu Gly Gly Thr Arg Leu Thr Ile
545                 550                 555                 560

Cys Gly Trp Asp Phe Gly Phe Arg Arg Asn Asn Lys Phe Asp Leu Lys
                    565                 570                 575

Lys Thr Arg Val Leu Leu Gly Asn Glu Ser Cys Thr Leu Thr Leu Ser
            580                 585                 590

Glu Ser Thr Met Asn Thr Leu Lys Cys Thr Val Gly Pro Ala Met Asn
            595                 600                 605

Lys His Phe Asn Met Ser Ile Ile Ile Ser Asn Gly His Gly Thr Thr
610                 615                 620

Gln Tyr Ser Thr Phe Ser Tyr Val Asp Pro Val Ile Thr Ser Ile Ser
625                 630                 635                 640

Pro Lys Tyr Gly Pro Met Ala Gly Gly Thr Leu Leu Thr Leu Thr Gly
                    645                 650                 655

Asn Tyr Leu Asn Ser Gly Asn Ser Arg His Ile Ser Ile Gly Gly Lys
            660                 665                 670

Thr Cys Thr Leu Lys Ser Val Ser Asn Ser Ile Leu Glu Cys Tyr Thr
            675                 680                 685

Pro Ala Gln Thr Ile Ser Thr Glu Phe Ala Val Lys Leu Lys Ile Asp
            690                 695                 700

Leu Ala Asn Arg Glu Thr Ser Ile Phe Ser Tyr Arg Glu Asp Pro Ile
705                 710                 715                 720

Val Tyr Glu Ile His Pro Thr Lys Ser Phe Ile Ser Gly Gly Ser Thr
                    725                 730                 735

Ile Thr Gly Val Gly Lys Asn Leu Asn Ser Val Ser Val Pro Arg Met
                    740                 745                 750

Val Ile Asn Val His Glu Ala Gly Arg Asn Phe Thr Val Ala Cys Gln
                    755                 760                 765

His Arg Ser Asn Ser Glu Ile Ile Cys Cys Thr Thr Pro Ser Leu Gln
            770                 775                 780

Gln Leu Asn Leu Gln Leu Pro Leu Lys Thr Lys Ala Phe Phe Met Leu
785                 790                 795                 800

Asp Gly Ile Leu Ser Lys Tyr Phe Asp Leu Ile Tyr Val His Asn Pro
                    805                 810                 815

Val Phe Lys Pro Phe Glu Lys Pro Val Met Ile Ser Met Gly Asn Glu
                    820                 825                 830
```

```
Asn Val Leu Glu Ile Lys Gly Asn Asp Ile Asp Pro Glu Ala Val Lys
            835                 840                 845

Gly Glu Val Leu Lys Val Gly Asn Lys Ser Cys Glu Asn Ile His Leu
        850                 855                 860

His Ser Glu Ala Val Leu Cys Thr Val Pro Asn Asp Leu Leu Lys Leu
865                 870                 875                 880

Asn Ser Glu Leu Asn Ile Glu Trp Lys Gln Ala Ile Ser Ser Thr Val
            885                 890                 895

Leu Gly Lys Val Ile Val Gln Pro Asp Gln Asn Phe Thr
                900                 905

<210> SEQ ID NO 7
<211> LENGTH: 909
<212> TYPE: PRT
<213> ORGANISM: Artificial
<220> FEATURE:
<223> OTHER INFORMATION: Llama-Human chimeric cMET

<400> SEQUENCE: 7

Glu Cys Lys Glu Ala Leu Val Lys Ser Arg Met Asn Val Asn Met Gln
1               5                   10                  15

Tyr Gln Leu Pro Asn Phe Thr Ala Glu Thr Arg Ile Gln Asn Val Val
            20                  25                  30

Leu His Lys His His Ile Tyr Leu Gly Ala Val Asn Tyr Ile Tyr Val
        35                  40                  45

Leu Asn Asp Lys Asp Leu Gln Lys Val Ala Glu Tyr Lys Thr Gly Pro
    50                  55                  60

Val Leu Glu His Pro His Cys Phe Pro Cys Glu Asp Cys Ser His Lys
65                  70                  75                  80

Ala Asn Leu Ser Asp Gly Val Trp Lys Asp Asn Ile Asn Met Ala Leu
                85                  90                  95

Leu Val Asp Thr Tyr Tyr Asp Asp Gln Leu Ile Ser Cys Gly Ser Val
            100                 105                 110

His Arg Gly Thr Cys Gln Arg His Val Leu Pro Pro Asp Asn Thr Ala
        115                 120                 125

Asp Ile Gln Ser Glu Val Tyr Cys Met Tyr Ser Pro Gln Thr Asp Glu
    130                 135                 140

Glu Pro Gly Gln Cys Pro Asp Cys Val Val Ser Ala Leu Gly Thr Lys
145                 150                 155                 160

Val Leu Leu Ser Glu Lys Asp Arg Phe Ile Asn Phe Val Gly Asn
                165                 170                 175

Thr Ile Asn Ser Ser Tyr Leu Pro Asp His Ser Leu His Ser Ile Ser
            180                 185                 190

Val Arg Arg Leu Lys Glu Thr Gln Asp Gly Phe Lys Phe Leu Thr Asp
        195                 200                 205

Gln Ser Tyr Ile Asp Val Leu Pro Glu Phe Gln Asp Thr Tyr Pro Ile
    210                 215                 220

Lys Tyr Val His Ala Phe Glu Ser Asn His Phe Ile Tyr Phe Leu Thr
225                 230                 235                 240

Val Gln Arg Glu Thr Leu Asp Ala Gln Thr Phe His Thr Arg Ile Ile
                245                 250                 255

Arg Phe Cys Ser Val Asp Ser Gly Leu His Ser Tyr Met Glu Met Pro
            260                 265                 270

Leu Glu Cys Ile Leu Thr Glu Lys Arg Arg Arg Ser Thr Lys Glu
        275                 280                 285
```

```
Glu Val Phe Asn Ile Leu Gln Ala Ala Tyr Val Ser Lys Pro Gly Ser
    290                 295                 300

Gln Leu Ala Lys Gln Ile Gly Ala Asn Leu Asn Asp Asp Ile Leu Tyr
305                 310                 315                 320

Gly Val Phe Ala Gln Ser Lys Pro Asp Ser Ala Glu Pro Met Asn Arg
                325                 330                 335

Ser Ala Val Cys Ala Phe Pro Val Lys Tyr Val Asn Glu Phe Phe Asn
                340                 345                 350

Lys Ile Val Asn Lys Asn Val Arg Cys Leu Gln His Phe Tyr Gly
                355                 360                 365

Pro Asn His Glu His Cys Phe Asn Arg Thr Leu Leu Arg Asn Ser Ser
    370                 375                 380

Gly Cys Glu Val Arg Asn Asp Glu Tyr Arg Thr Glu Phe Thr Thr Ala
385                 390                 395                 400

Leu Gln Arg Val Asp Leu Phe Thr Gly Gln Phe Asn Gln Val Leu Leu
                405                 410                 415

Thr Ser Ile Ser Thr Phe Ile Lys Gly Asp Leu Thr Ile Ala Asn Leu
                420                 425                 430

Gly Thr Ser Glu Gly Arg Phe Met Gln Val Val Ser Arg Ser Gly
                435                 440                 445

Leu Ser Thr Pro His Val Asn Phe Leu Leu Asp Ser His Pro Val Ser
    450                 455                 460

Pro Glu Val Ile Val Glu His Thr Leu Asn Gln Asn Gly Tyr Thr Leu
465                 470                 475                 480

Val Ile Thr Gly Lys Lys Ile Thr Lys Ile Pro Leu Asn Gly Leu Gly
                485                 490                 495

Cys Arg His Phe Gln Ser Cys Ser Gln Cys Leu Ser Ala Pro Pro Phe
                500                 505                 510

Val Gln Cys Gly Trp Cys His Asp Lys Cys Val Arg Ser Glu Glu Cys
                515                 520                 525

Leu Ser Gly Thr Trp Thr Gln Gln Ile Cys Leu Pro Ala Ile Tyr Lys
    530                 535                 540

Val Phe Pro Asn Ser Ala Pro Leu Glu Gly Gly Thr Arg Leu Thr Ile
545                 550                 555                 560

Cys Gly Trp Asp Phe Gly Phe Arg Arg Asn Asn Lys Phe Asp Leu Lys
                565                 570                 575

Lys Thr Arg Val Leu Leu Gly Asn Glu Ser Cys Thr Leu Thr Leu Ser
                580                 585                 590

Glu Ser Thr Met Asn Thr Leu Lys Cys Thr Val Gly Pro Ala Met Asn
    595                 600                 605

Lys His Phe Asn Met Ser Ile Ile Ile Ser Asn Gly His Gly Thr Thr
    610                 615                 620

Gln Tyr Ser Thr Phe Ser Tyr Val Asp Pro Val Ile Thr Ser Ile Ser
625                 630                 635                 640

Pro Lys Tyr Gly Pro Met Ala Gly Gly Thr Leu Leu Thr Leu Thr Gly
                645                 650                 655

Asn Tyr Leu Asn Ser Gly Asn Ser Arg His Ile Ser Ile Gly Gly Lys
                660                 665                 670

Thr Cys Thr Leu Lys Ser Val Ser Asn Ser Ile Leu Glu Cys Tyr Thr
    675                 680                 685

Pro Ala Gln Thr Ile Ser Thr Glu Phe Ala Val Lys Leu Lys Ile Asp
    690                 695                 700
```

```
Leu Ala Asn Arg Glu Thr Ser Ile Phe Ser Tyr Arg Glu Asp Pro Ile
705                 710                 715                 720

Val Tyr Glu Ile His Pro Thr Lys Ser Phe Ile Ser Gly Gly Ser Thr
            725                 730                 735

Ile Thr Gly Val Gly Lys Asn Leu Asn Ser Val Ser Val Pro Arg Met
        740                 745                 750

Val Ile Asn Val His Glu Ala Gly Arg Asn Phe Thr Val Ala Cys Gln
    755                 760                 765

His Arg Ser Asn Ser Glu Ile Ile Cys Cys Thr Thr Pro Ser Leu Gln
770                 775                 780

Gln Leu Asn Leu Gln Leu Pro Leu Lys Thr Lys Ala Phe Phe Met Leu
785                 790                 795                 800

Asp Gly Ile Leu Ser Lys Tyr Phe Asp Leu Ile Tyr Val His Asn Pro
                805                 810                 815

Val Phe Lys Pro Phe Glu Lys Pro Val Met Ile Ser Met Gly Asn Glu
            820                 825                 830

Asn Val Leu Glu Ile Lys Gly Asn Asp Ile Asp Pro Glu Ala Val Lys
        835                 840                 845

Gly Glu Val Leu Lys Val Gly Asn Lys Ser Cys Glu Asn Ile His Leu
    850                 855                 860

His Ser Glu Ala Val Leu Cys Thr Val Pro Asn Asp Leu Leu Lys Leu
865                 870                 875                 880

Asn Ser Glu Leu Asn Ile Glu Trp Lys Gln Ala Ile Ser Ser Thr Val
                885                 890                 895

Leu Gly Lys Val Ile Val Gln Pro Asp Gln Asn Phe Thr
                900                 905

<210> SEQ ID NO 8
<211> LENGTH: 908
<212> TYPE: PRT
<213> ORGANISM: Artificial
<220> FEATURE:
<223> OTHER INFORMATION: Llama-Human chimeric cMET

<400> SEQUENCE: 8

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160
```

-continued

Leu Ser Ser Val Lys Asp Arg Phe Ile Asn Phe Phe Val Gly Asn Thr
            165                 170                 175

Ile Asn Ser Ser Tyr Phe Pro Asp His Pro Leu His Ser Ile Ser Val
        180                 185                 190

Arg Arg Leu Lys Glu Thr Lys Asp Gly Phe Met Phe Leu Thr Asp Gln
            195                 200                 205

Ser Tyr Ile Asp Val Leu Pro Glu Phe Arg Asp Ser Tyr Pro Ile Lys
        210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
            245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
        275                 280                 285

Val Phe Asn Ile Leu Gln Ala Ala Tyr Val Ser Lys Pro Gly Ala Gln
    290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
            325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
        355                 360                 365

Asn His Glu His Cys Phe Asn Arg Thr Leu Leu Arg Asn Ser Ser Gly
    370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
            405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Val Ser Arg Ser Gly Pro
        435                 440                 445

Ser Thr Pro His Val Asn Phe Leu Leu Asp Ser His Pro Val Ser Pro
    450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
            485                 490                 495

Glu His Phe Gln Ser Cys Ser Gln Cys Leu Ser Ala Pro Ser Phe Val
            500                 505                 510

Gln Cys Gly Trp Cys His Asp Lys Cys Val Gln Leu Glu Glu Cys Ser
        515                 520                 525

Gly Gly Ile Trp Thr Gln Glu Ile Cys Leu Pro Thr Ile Tyr Lys Val
    530                 535                 540

Leu Pro Thr Ser Ala Pro Leu Glu Gly Gly Thr Thr Leu Thr Ile Cys
545                 550                 555                 560

Gly Trp Asp Phe Gly Phe Arg Arg Asn Asn Lys Ser Asp Leu Lys Lys
            565                 570                 575

Thr Lys Val Phe Leu Gly Asn Glu Ser Cys Thr Leu Thr Leu Ser Glu

```
                580                 585                 590
Ser Thr Thr Asn Thr Leu Lys Cys Thr Val Gly Pro Ala Met Asn Glu
                    595                 600                 605

His Phe Asn Val Ser Ile Ile Ile Ser Asn Asn Arg Gly Thr Ala Gln
    610                 615                 620

Tyr Ser Thr Phe Ser Tyr Val Asp Pro Ile Ile Thr Ser Ile Ser Pro
625                 630                 635                 640

Ser Tyr Gly Pro Lys Thr Gly Gly Thr Leu Leu Thr Leu Thr Gly Lys
                    645                 650                 655

His Leu Asn Ser Gly Asn Ser Arg His Ile Ser Ile Gly Gly Lys Thr
        660                 665                 670

Cys Thr Leu Lys Ser Val Ser Asp Ser Ile Leu Glu Cys Tyr Thr Pro
        675                 680                 685

Ala Gln Thr Thr Pro Thr Glu Phe Pro Val Lys Leu Lys Ile Asp Leu
        690                 695                 700

Ala Asn Arg Glu Ile Asn Ser Phe Ser Tyr Arg Glu Asp Pro Val Val
705                 710                 715                 720

Tyr Glu Ile His Pro Thr Lys Ser Phe Ile Ser Gly Gly Ser Thr Ile
                    725                 730                 735

Thr Gly Val Gly Lys Tyr Leu Asn Ser Val Ser Val Leu Arg Met Val
                740                 745                 750

Ile Asn Val His Glu Ala Gly Arg Asn Phe Thr Val Ala Cys Gln His
            755                 760                 765

Arg Ser Asn Ser Glu Ile Ile Cys Cys Thr Thr Pro Ser Leu Gln Gln
770                 775                 780

Leu Asn Leu Gln Leu Pro Val Lys Thr Lys Ala Phe Phe Met Leu Asp
785                 790                 795                 800

Gly Ile His Ser Lys His Phe Asp Leu Ile Tyr Val His Asn Pro Val
                    805                 810                 815

Phe Lys Pro Phe Glu Lys Pro Val Met Ile Ser Ile Gly Asn Glu Asn
                820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Ser His
850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Val Ser Ser Thr Val Leu
                    885                 890                 895

Gly Lys Val Ile Val Gln Pro Asp Gln Asn Phe Thr
                900                 905

<210> SEQ ID NO 9
<211> LENGTH: 908
<212> TYPE: PRT
<213> ORGANISM: Artificial
<220> FEATURE:
<223> OTHER INFORMATION: Llama-Human chimeric cMET

<400> SEQUENCE: 9

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
```

```
                35                  40                  45
Leu Asn Glu Glu Asp Leu Gln Lys Val Ala Glu Tyr Lys Thr Gly Pro
 50                  55                  60

Val Leu Glu His Pro Asp Cys Phe Pro Cys Gln Asp Cys Ser Ser Lys
65                   70                  75                  80

Ala Asn Leu Ser Gly Val Trp Lys Asp Asn Ile Asn Met Ala Leu
                85                  90                  95

Val Val Asp Thr Tyr Tyr Asp Asp Gln Leu Ile Ser Cys Gly Ser Val
                100                 105                 110

Asn Arg Gly Thr Cys Gln Arg His Val Phe Pro His Asn His Thr Ala
            115                 120                 125

Asp Ile Gln Ser Glu Val His Cys Ile Phe Ser Pro Gln Ile Glu Glu
        130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
        275                 280                 285

Val Phe Asn Ile Leu Gln Ala Ala Tyr Val Ser Lys Pro Gly Ala Gln
290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
        355                 360                 365

Asn His Glu His Cys Phe Asn Arg Thr Leu Leu Arg Asn Ser Ser Gly
370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Val Ser Arg Ser Gly Pro
        435                 440                 445

Ser Thr Pro His Val Asn Phe Leu Leu Asp Ser His Pro Val Ser Pro
450                 455                 460
```

```
Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
            500                 505                 510

Gln Cys Gly Trp Cys His Asp Lys Cys Val Gln Leu Glu Glu Cys Ser
        515                 520                 525

Gly Gly Ile Trp Thr Gln Glu Ile Cys Leu Pro Thr Ile Tyr Lys Val
    530                 535                 540

Leu Pro Thr Ser Ala Pro Leu Glu Gly Gly Thr Thr Leu Thr Ile Cys
545                 550                 555                 560

Gly Trp Asp Phe Gly Phe Arg Arg Asn Asn Lys Ser Asp Leu Lys Lys
                565                 570                 575

Thr Lys Val Phe Leu Gly Asn Glu Ser Cys Thr Leu Thr Leu Ser Glu
            580                 585                 590

Ser Thr Thr Asn Thr Leu Lys Cys Thr Val Gly Pro Ala Met Asn Glu
        595                 600                 605

His Phe Asn Val Ser Ile Ile Ser Asn Asn Arg Gly Thr Ala Gln
    610                 615                 620

Tyr Ser Thr Phe Ser Tyr Val Asp Pro Ile Ile Thr Ser Ile Ser Pro
625                 630                 635                 640

Ser Tyr Gly Pro Lys Thr Gly Gly Thr Leu Leu Thr Leu Thr Gly Lys
                645                 650                 655

His Leu Asn Ser Gly Asn Ser Arg His Ile Ser Ile Gly Gly Lys Thr
            660                 665                 670

Cys Thr Leu Lys Ser Val Ser Asp Ser Ile Leu Glu Cys Tyr Thr Pro
        675                 680                 685

Ala Gln Thr Thr Pro Thr Glu Phe Pro Val Lys Leu Lys Ile Asp Leu
    690                 695                 700

Ala Asn Arg Glu Ile Asn Ser Phe Ser Tyr Arg Glu Asp Pro Val Val
705                 710                 715                 720

Tyr Glu Ile His Pro Thr Lys Ser Phe Ile Ser Gly Gly Ser Thr Ile
                725                 730                 735

Ile Gly Val Gly Lys Tyr Leu Asn Ser Val Ser Val Leu Arg Met Val
            740                 745                 750

Ile Asn Val His Glu Ala Gly Arg Asn Phe Thr Val Ala Cys Gln His
        755                 760                 765

Arg Ser Asn Ser Glu Ile Ile Cys Cys Thr Thr Pro Ser Leu Gln Gln
    770                 775                 780

Leu Asn Leu Gln Leu Pro Val Lys Thr Lys Ala Phe Phe Met Leu Asp
785                 790                 795                 800

Gly Ile His Ser Lys His Phe Asp Leu Ile Tyr Val His Asn Pro Val
                805                 810                 815

Phe Lys Pro Phe Glu Lys Pro Val Met Ile Ser Ile Gly Asn Glu Asn
            820                 825                 830

Val Leu Glu Ile Lys Gly Asn Asp Ile Asp Pro Glu Ala Val Lys Gly
        835                 840                 845

Glu Val Leu Lys Val Gly Asn Lys Ser Cys Glu Asn Ile His Ser His
    850                 855                 860

Ser Glu Ala Val Leu Cys Thr Val Pro Asn Asp Leu Leu Lys Leu Asn
865                 870                 875                 880
```

-continued

```
Ser Glu Leu Asn Ile Glu Trp Lys Gln Ala Val Ser Ser Thr Val Leu
                885                 890                 895
Gly Lys Val Ile Val Gln Pro Asp Gln Asn Phe Thr
        900                 905

<210> SEQ ID NO 10
<211> LENGTH: 907
<212> TYPE: PRT
<213> ORGANISM: Artificial
<220> FEATURE:
<223> OTHER INFORMATION: Llama-Human chimeric cMET

<400> SEQUENCE: 10

Cys Lys Glu Ala Leu Ala Lys Ser Glu Met Asn Val Asn Met Lys Tyr
1               5                  10                  15

Gln Leu Pro Asn Phe Thr Ala Glu Thr Pro Ile Gln Asn Val Ile Leu
            20                  25                  30

His Glu His His Ile Phe Leu Gly Ala Thr Asn Tyr Ile Tyr Val Leu
        35                  40                  45

Asn Glu Glu Asp Leu Gln Lys Val Ala Glu Tyr Lys Thr Gly Pro Val
    50                  55                  60

Leu Glu His Pro Asp Cys Phe Pro Cys Gln Asp Cys Ser Ser Lys Ala
65                  70                  75                  80

Asn Leu Ser Gly Gly Val Trp Lys Asp Asn Ile Asn Met Ala Leu Val
                85                  90                  95

Val Asp Thr Tyr Tyr Asp Asp Gln Leu Ile Ser Cys Gly Ser Val Asn
            100                 105                 110

Arg Gly Thr Cys Gln Arg His Val Phe Pro His Asn His Thr Ala Asp
        115                 120                 125

Ile Gln Ser Glu Val His Cys Ile Phe Ser Pro Gln Ile Glu Glu Pro
    130                 135                 140

Ser Gln Cys Pro Asp Cys Val Val Ser Ala Leu Gly Ala Lys Val Leu
145                 150                 155                 160

Ser Ser Val Lys Asp Arg Phe Ile Asn Phe Val Gly Asn Thr Ile
                165                 170                 175

Asn Ser Ser Tyr Phe Pro Asp His Pro Leu His Ser Ile Ser Val Arg
            180                 185                 190

Arg Leu Lys Glu Thr Lys Asp Gly Phe Met Phe Leu Thr Asp Gln Ser
        195                 200                 205

Tyr Ile Asp Val Leu Pro Glu Phe Arg Asp Ser Tyr Pro Ile Lys Tyr
    210                 215                 220

Val His Ala Phe Glu Ser Asn Asn Phe Ile Tyr Phe Leu Thr Val Gln
225                 230                 235                 240

Arg Glu Thr Leu Asp Ala Gln Thr Phe His Thr Arg Ile Ile Arg Phe
                245                 250                 255

Cys Ser Ile Asn Ser Gly Leu His Ser Tyr Met Glu Met Pro Leu Glu
            260                 265                 270

Cys Ile Leu Thr Glu Lys Arg Lys Lys Arg Ser Thr Lys Lys Glu Val
        275                 280                 285

Phe Asn Ile Leu Gln Ala Ala Tyr Val Ser Lys Pro Gly Ala Gln Leu
    290                 295                 300

Ala Arg Gln Ile Gly Ala Ser Leu Asn Asp Asp Ile Leu Phe Gly Val
305                 310                 315                 320

Phe Ala Gln Ser Lys Pro Asp Ser Ala Glu Pro Met Asp Arg Ser Ala
                325                 330                 335
```

-continued

```
Met Cys Ala Phe Pro Ile Lys Tyr Val Asn Asp Phe Phe Asn Lys Ile
                340                 345                 350

Val Asn Lys Asn Asn Val Arg Cys Leu Gln His Phe Tyr Gly Pro Asn
            355                 360                 365

His Glu His Cys Phe Asn Arg Thr Leu Leu Arg Asn Ser Ser Gly Cys
        370                 375                 380

Glu Ala Arg Arg Asp Glu Tyr Arg Thr Glu Phe Thr Thr Ala Leu Gln
385                 390                 395                 400

Arg Val Asp Leu Phe Met Gly Gln Phe Ser Glu Val Leu Leu Thr Ser
                405                 410                 415

Ile Ser Thr Phe Ile Lys Gly Asp Leu Thr Ile Ala Asn Leu Gly Thr
            420                 425                 430

Ser Glu Gly Arg Phe Met Gln Val Val Ser Arg Ser Gly Pro Ser
        435                 440                 445

Thr Pro His Val Asn Phe Leu Leu Asp Ser His Pro Val Ser Pro Glu
        450                 455                 460

Val Ile Val Glu His Thr Leu Asn Gln Asn Gly Tyr Thr Leu Val Ile
465                 470                 475                 480

Thr Gly Lys Lys Ile Thr Lys Ile Pro Leu Asn Gly Leu Gly Cys Arg
                485                 490                 495

His Phe Gln Ser Cys Ser Gln Cys Leu Ser Ala Pro Pro Phe Val Gln
            500                 505                 510

Cys Gly Trp Cys His Asp Lys Cys Val Arg Ser Glu Glu Cys Leu Ser
        515                 520                 525

Gly Thr Trp Thr Gln Gln Ile Cys Leu Pro Thr Ile Tyr Lys Val Leu
        530                 535                 540

Pro Thr Ser Ala Pro Leu Glu Gly Gly Thr Thr Leu Thr Ile Cys Gly
545                 550                 555                 560

Trp Asp Phe Gly Phe Arg Arg Asn Asn Lys Ser Asp Leu Lys Lys Thr
                565                 570                 575

Lys Val Phe Leu Gly Asn Glu Ser Cys Thr Leu Thr Leu Ser Glu Ser
            580                 585                 590

Thr Thr Asn Thr Leu Lys Cys Thr Val Gly Pro Ala Met Asn Glu His
        595                 600                 605

Phe Asn Val Ser Ile Ile Ile Ser Asn Asn Arg Gly Thr Ala Gln Tyr
        610                 615                 620

Ser Thr Phe Ser Tyr Val Asp Pro Ile Ile Thr Ser Ile Ser Pro Ser
625                 630                 635                 640

Tyr Gly Pro Lys Thr Gly Gly Thr Leu Leu Thr Leu Thr Gly Lys His
                645                 650                 655

Leu Asn Ser Gly Asn Ser Arg His Ile Ser Ile Gly Gly Lys Thr Cys
            660                 665                 670

Thr Leu Lys Ser Val Ser Asp Ser Ile Leu Glu Cys Tyr Thr Pro Ala
        675                 680                 685

Gln Thr Thr Pro Thr Glu Phe Pro Val Lys Leu Lys Ile Asp Leu Ala
        690                 695                 700

Asn Arg Glu Ile Asn Ser Phe Ser Tyr Arg Glu Asp Pro Val Val Tyr
705                 710                 715                 720

Glu Ile His Pro Thr Lys Ser Phe Ile Ser Gly Gly Ser Thr Ile Thr
                725                 730                 735

Gly Val Gly Lys Tyr Leu Asn Ser Val Ser Val Leu Arg Met Val Ile
            740                 745                 750

Asn Val His Glu Ala Gly Arg Asn Phe Thr Val Ala Cys Gln His Arg
```

```
                755                 760                 765
Ser Asn Ser Glu Ile Ile Cys Cys Thr Thr Pro Ser Leu Gln Gln Leu
        770                 775                 780

Asn Leu Gln Leu Pro Val Lys Thr Lys Ala Phe Phe Met Leu Asp Gly
785                 790                 795                 800

Ile His Ser Lys His Phe Asp Leu Ile Tyr Val His Asn Pro Val Phe
                805                 810                 815

Lys Pro Phe Glu Lys Pro Val Met Ile Ser Ile Gly Asn Glu Asn Val
        820                 825                 830

Leu Glu Ile Lys Gly Asn Asp Ile Asp Pro Glu Ala Val Lys Gly Glu
                835                 840                 845

Val Leu Lys Val Gly Asn Lys Ser Cys Glu Asn Ile His Ser His Ser
850                 855                 860

Glu Ala Val Leu Cys Thr Val Pro Asn Asp Leu Leu Lys Leu Asn Ser
865                 870                 875                 880

Glu Leu Asn Ile Glu Trp Lys Gln Ala Val Ser Ser Thr Val Leu Gly
                885                 890                 895

Lys Val Ile Val Gln Pro Asp Gln Asn Phe Thr
                900                 905

<210> SEQ ID NO 11
<211> LENGTH: 908
<212> TYPE: PRT
<213> ORGANISM: Artificial
<220> FEATURE:
<223> OTHER INFORMATION: Llama-Human chimeric cMET

<400> SEQUENCE: 11

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
                20                  25                  30

Leu His Glu His His Ile Phe Leu Gly Ala Thr Asn Tyr Ile Tyr Val
            35                  40                  45

Leu Asn Glu Glu Asp Leu Gln Lys Val Ala Glu Tyr Lys Thr Gly Pro
50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
                100                 105                 110

Asn Arg Gly Thr Cys Gln Arg His Val Phe Pro His Asn His Thr Ala
            115                 120                 125

Asp Ile Gln Ser Glu Val His Cys Ile Phe Ser Pro Gln Ile Glu Glu
        130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
                180                 185                 190

Arg Arg Leu Lys Glu Thr Lys Asp Gly Phe Met Phe Leu Thr Asp Gln
            195                 200                 205

Ser Tyr Ile Asp Val Leu Pro Glu Phe Arg Asp Ser Tyr Pro Ile Lys
```

```
            210                 215                 220
Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
            245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Arg Ser Thr Lys Lys Glu
            275                 280                 285

Val Phe Asn Ile Leu Gln Ala Ala Tyr Val Ser Lys Pro Gly Ala Gln
            290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
            325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
            355                 360                 365

Asn His Glu His Cys Phe Asn Arg Thr Leu Leu Arg Asn Ser Ser Gly
            370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
            405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Ser Arg Ser Gly Pro
            435                 440                 445

Ser Thr Pro His Val Asn Phe Leu Leu Asp Ser His Pro Val Ser Pro
450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
            485                 490                 495

Arg His Phe Gln Ser Cys Ser Gln Cys Leu Ser Ala Pro Pro Phe Val
            500                 505                 510

Gln Cys Gly Trp Cys His Asp Lys Cys Val Arg Ser Glu Glu Cys Leu
            515                 520                 525

Ser Gly Thr Trp Thr Gln Gln Ile Cys Leu Pro Ala Ile Tyr Lys Val
            530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Ser Asp Leu Lys Lys
            565                 570                 575

Thr Lys Val Phe Leu Gly Asn Glu Ser Cys Thr Leu Thr Leu Ser Glu
            580                 585                 590

Ser Thr Thr Asn Thr Leu Lys Cys Thr Val Gly Pro Ala Met Asn Glu
            595                 600                 605

His Phe Asn Val Ser Ile Ile Ile Ser Asn Asn Arg Gly Thr Ala Gln
            610                 615                 620

Tyr Ser Thr Phe Ser Tyr Val Asp Pro Ile Ile Thr Ser Ile Ser Pro
625                 630                 635                 640
```

```
Ser Tyr Gly Pro Lys Thr Gly Thr Leu Leu Thr Leu Thr Gly Lys
            645             650                 655

His Leu Asn Ser Gly Asn Ser Arg His Ile Ser Ile Gly Gly Lys Thr
                660                 665                 670

Cys Thr Leu Lys Ser Val Ser Asp Ser Ile Leu Glu Cys Tyr Thr Pro
            675                 680                 685

Ala Gln Thr Thr Pro Thr Glu Phe Pro Val Lys Leu Lys Ile Asp Leu
        690                 695                 700

Ala Asn Arg Glu Ile Asn Ser Phe Ser Tyr Arg Glu Asp Pro Val Val
705                 710                 715                 720

Tyr Glu Ile His Pro Thr Lys Ser Phe Ile Ser Gly Gly Ser Thr Ile
                725                 730                 735

Thr Gly Val Gly Lys Tyr Leu Asn Ser Val Ser Val Leu Arg Met Val
            740                 745                 750

Ile Asn Val His Glu Ala Gly Arg Asn Phe Thr Val Ala Cys Gln His
            755                 760                 765

Arg Ser Asn Ser Glu Ile Ile Cys Cys Thr Thr Pro Ser Leu Gln Gln
        770                 775                 780

Leu Asn Leu Gln Leu Pro Val Lys Thr Lys Ala Phe Phe Met Leu Asp
785                 790                 795                 800

Gly Ile His Ser Lys His Phe Asp Leu Ile Tyr Val His Asn Pro Val
                805                 810                 815

Phe Lys Pro Phe Glu Lys Pro Val Met Ile Ser Ile Gly Asn Glu Asn
            820                 825                 830

Val Leu Glu Ile Lys Gly Asn Asp Ile Asp Pro Glu Ala Val Lys Gly
        835                 840                 845

Glu Val Leu Lys Val Gly Asn Lys Ser Cys Glu Asn Ile His Ser His
    850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Val Ser Ser Thr Val Leu
                885                 890                 895

Gly Lys Val Ile Val Gln Pro Asp Gln Asn Phe Thr
            900                 905
```

<210> SEQ ID NO 12
<211> LENGTH: 908
<212> TYPE: PRT
<213> ORGANISM: Artificial
<220> FEATURE:
<223> OTHER INFORMATION: Llama-Human chimeric cMET

<400> SEQUENCE: 12

```
Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95
```

```
Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
            115                 120                 125

Asp Ile Gln Ser Glu Val His Cys Ile Phe Ser Pro Gln Ile Glu Glu
            130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
            195                 200                 205

Ser Tyr Ile Asp Val Leu Pro Glu Phe Arg Asp Ser Tyr Pro Ile Lys
            210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
            245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
            275                 280                 285

Val Phe Asn Ile Leu Gln Ala Ala Tyr Val Ser Lys Pro Gly Ala Gln
            290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
            355                 360                 365

Asn His Glu His Cys Phe Asn Arg Thr Leu Leu Arg Asn Ser Ser Gly
            370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Val Ser Arg Ser Gly Pro
            435                 440                 445

Ser Thr Pro His Val Asn Phe Leu Leu Asp Ser His Pro Val Ser Pro
            450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
            500                 505                 510
```

```
Gln Cys Gly Trp Cys His Asp Lys Cys Val Arg Ser Glu Cys Leu
        515                 520                 525

Ser Gly Thr Trp Thr Gln Gln Ile Cys Leu Pro Ala Ile Tyr Lys Val
530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
                565                 570                 575

Thr Arg Val Leu Leu Gly Asn Glu Ser Cys Thr Leu Thr Leu Ser Glu
                580                 585                 590

Ser Thr Met Asn Thr Leu Lys Cys Thr Val Gly Pro Ala Met Asn Glu
            595                 600                 605

His Phe Asn Val Ser Ile Ile Ile Ser Asn Asn Arg Gly Thr Ala Gln
610                 615                 620

Tyr Ser Thr Phe Ser Tyr Val Asp Pro Ile Ile Thr Ser Ile Ser Pro
625                 630                 635                 640

Ser Tyr Gly Pro Lys Thr Gly Gly Thr Leu Leu Thr Leu Thr Gly Lys
                645                 650                 655

His Leu Asn Ser Gly Asn Ser Arg His Ile Ser Ile Gly Gly Lys Thr
            660                 665                 670

Cys Thr Leu Lys Ser Val Ser Asp Ser Ile Leu Glu Cys Tyr Thr Pro
        675                 680                 685

Ala Gln Thr Thr Pro Thr Glu Phe Pro Val Lys Leu Lys Ile Asp Leu
    690                 695                 700

Ala Asn Arg Glu Ile Asn Ser Phe Ser Tyr Arg Glu Asp Pro Val Val
705                 710                 715                 720

Tyr Glu Ile His Pro Thr Lys Ser Phe Ile Ser Gly Gly Ser Thr Ile
                725                 730                 735

Thr Gly Val Gly Lys Tyr Leu Asn Ser Val Ser Val Leu Arg Met Val
            740                 745                 750

Ile Asn Val His Glu Ala Gly Arg Asn Phe Thr Val Ala Cys Gln His
        755                 760                 765

Arg Ser Asn Ser Glu Ile Ile Cys Cys Thr Thr Pro Ser Leu Gln Gln
    770                 775                 780

Leu Asn Leu Gln Leu Pro Val Lys Thr Lys Ala Phe Phe Met Leu Asp
785                 790                 795                 800

Gly Ile His Ser Lys His Phe Asp Leu Ile Tyr Val His Asn Pro Val
                805                 810                 815

Phe Lys Pro Phe Glu Lys Pro Val Met Ile Ser Ile Gly Asn Glu Asn
            820                 825                 830

Val Leu Glu Ile Lys Gly Asn Asp Ile Asp Pro Glu Ala Val Lys Gly
        835                 840                 845

Glu Val Leu Lys Val Gly Asn Lys Ser Cys Glu Asn Ile His Ser His
    850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Val Ser Ser Thr Val Leu
                885                 890                 895

Gly Lys Val Ile Val Gln Pro Asp Gln Asn Phe Thr
            900                 905

<210> SEQ ID NO 13
<211> LENGTH: 908
<212> TYPE: PRT
```

<213> ORGANISM: Artificial
<220> FEATURE:
<223> OTHER INFORMATION: Llama-Human chimeric cMET

<400> SEQUENCE: 13

```
Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
        275                 280                 285

Val Phe Asn Ile Leu Gln Ala Ala Tyr Val Ser Lys Pro Gly Ala Gln
290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
        355                 360                 365

Asn His Glu His Cys Phe Asn Arg Thr Leu Leu Arg Asn Ser Ser Gly
370                 375                 380

Cys Glu Ala Arg Arg Asp Glu Tyr Arg Thr Glu Phe Thr Thr Ala Leu
```

```
             385                 390                 395                 400
        Gln Arg Val Asp Leu Phe Met Gly Gln Phe Ser Glu Val Leu Leu Thr
                        405                 410                 415

Ser Ile Ser Thr Phe Ile Lys Gly Asp Leu Thr Ile Ala Asn Leu Gly
                        420                 425                 430

Thr Ser Glu Gly Arg Phe Met Gln Val Val Ser Arg Ser Gly Pro
                        435                 440                 445

Ser Thr Pro His Val Asn Phe Leu Leu Asp Ser His Pro Val Ser Pro
                        450                 455                 460

Glu Val Ile Val Glu His Thr Leu Asn Gln Asn Gly Tyr Thr Leu Val
        465                 470                 475                 480

Ile Thr Gly Lys Lys Ile Thr Lys Ile Pro Leu Asn Gly Leu Gly Cys
                        485                 490                 495

Arg His Phe Gln Ser Cys Ser Gln Cys Leu Ser Ala Pro Pro Phe Val
                        500                 505                 510

Gln Cys Gly Trp Cys His Asp Lys Cys Val Arg Ser Glu Glu Cys Leu
                        515                 520                 525

Ser Gly Thr Trp Thr Gln Gln Ile Cys Leu Pro Ala Ile Tyr Lys Val
                        530                 535                 540

Phe Pro Asn Ser Ala Pro Leu Glu Gly Gly Thr Arg Leu Thr Ile Cys
        545                 550                 555                 560

Gly Trp Asp Phe Gly Phe Arg Arg Asn Asn Lys Phe Asp Leu Lys Lys
                        565                 570                 575

Thr Arg Val Leu Leu Gly Asn Glu Ser Cys Thr Leu Thr Leu Ser Glu
                        580                 585                 590

Ser Thr Met Asn Thr Leu Lys Cys Thr Val Gly Pro Ala Met Asn Lys
                        595                 600                 605

His Phe Asn Met Ser Ile Ile Ile Ser Asn Gly His Gly Thr Thr Gln
                        610                 615                 620

Tyr Ser Thr Phe Ser Tyr Val Asp Pro Ile Ile Thr Ser Ile Ser Pro
        625                 630                 635                 640

Ser Tyr Gly Pro Lys Thr Gly Gly Thr Leu Leu Thr Leu Thr Gly Lys
                        645                 650                 655

His Leu Asn Ser Gly Asn Ser Arg His Ile Ser Ile Gly Gly Lys Thr
                        660                 665                 670

Cys Thr Leu Lys Ser Val Ser Asp Ser Ile Leu Glu Cys Tyr Thr Pro
                        675                 680                 685

Ala Gln Thr Thr Pro Thr Glu Phe Pro Val Lys Leu Lys Ile Asp Leu
        690                 695                 700

Ala Asn Arg Glu Ile Asn Ser Phe Ser Tyr Arg Glu Asp Pro Val Val
        705                 710                 715                 720

Tyr Glu Ile His Pro Thr Lys Ser Phe Ile Ser Gly Gly Ser Thr Ile
                        725                 730                 735

Thr Gly Val Gly Lys Tyr Leu Asn Ser Val Ser Val Leu Arg Met Val
                        740                 745                 750

Ile Asn Val His Glu Ala Gly Arg Asn Phe Thr Val Ala Cys Gln His
                        755                 760                 765

Arg Ser Asn Ser Glu Ile Ile Cys Cys Thr Thr Pro Ser Leu Gln Gln
                        770                 775                 780

Leu Asn Leu Gln Leu Pro Val Lys Thr Lys Ala Phe Phe Met Leu Asp
        785                 790                 795                 800

Gly Ile His Ser Lys His Phe Asp Leu Ile Tyr Val His Asn Pro Val
                        805                 810                 815
```

Phe Lys Pro Phe Glu Lys Pro Val Met Ile Ser Ile Gly Asn Glu Asn
                820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Ser His
        850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Val Ser Ser Thr Val Leu
                885                 890                 895

Gly Lys Val Ile Val Gln Pro Asp Gln Asn Phe Thr
            900                 905

<210> SEQ ID NO 14
<211> LENGTH: 102
<212> TYPE: PRT
<213> ORGANISM: Homo sapiens

<400> SEQUENCE: 14

Val Asp Thr Tyr Tyr Asp Asp Gln Leu Ile Ser Cys Gly Ser Val Asn
1               5                   10                  15

Arg Gly Thr Cys Gln Arg His Val Phe Pro His Asn His Thr Ala Asp
            20                  25                  30

Ile Gln Ser Glu Val His Cys Ile Phe Ser Pro Gln Ile Glu Glu Pro
        35                  40                  45

Ser Gln Cys Pro Asp Cys Val Val Ser Ala Leu Gly Ala Lys Val Leu
    50                  55                  60

Ser Ser Val Lys Asp Arg Phe Ile Asn Phe Phe Val Gly Asn Thr Ile
65                  70                  75                  80

Asn Ser Ser Tyr Phe Pro Asp His Pro Leu His Ser Ile Ser Val Arg
                85                  90                  95

Arg Leu Lys Glu Thr Lys
            100

<210> SEQ ID NO 15
<211> LENGTH: 111
<212> TYPE: PRT
<213> ORGANISM: Homo sapiens

<400> SEQUENCE: 15

Arg Ser Glu Glu Cys Leu Ser Gly Thr Trp Thr Gln Gln Ile Cys Leu
1               5                   10                  15

Pro Ala Ile Tyr Lys Val Phe Pro Asn Ser Ala Pro Leu Glu Gly Gly
            20                  25                  30

Thr Arg Leu Thr Ile Cys Gly Trp Asp Phe Gly Phe Arg Arg Asn Asn
        35                  40                  45

Lys Phe Asp Leu Lys Lys Thr Arg Val Leu Leu Gly Asn Glu Ser Cys
    50                  55                  60

Thr Leu Thr Leu Ser Glu Ser Thr Met Asn Thr Leu Lys Cys Thr Val
65                  70                  75                  80

Gly Pro Ala Met Asn Lys His Phe Asn Met Ser Ile Ile Ile Ser Asn
                85                  90                  95

Gly His Gly Thr Thr Gln Tyr Ser Thr Phe Ser Tyr Val Asp Pro
            100                 105                 110

<210> SEQ ID NO 16

```
<211> LENGTH: 142
<212> TYPE: PRT
<213> ORGANISM: Homo sapiens

<400> SEQUENCE: 16

Ser Leu Gly Trp Asp Val Ala Glu Leu Gln Leu Asn His Thr Gly Pro
1               5                   10                  15

Gln Gln Asp Pro Arg Leu Tyr Trp Gln Gly Gly Pro Ala Leu Gly Arg
            20                  25                  30

Ser Phe Leu His Gly Pro Glu Leu Asp Lys Gly Gln Leu Arg Ile His
        35                  40                  45

Arg Asp Gly Ile Tyr Met Val His Ile Gln Val Thr Leu Ala Ile Cys
    50                  55                  60

Ser Ser Thr Thr Ala Ser Arg His His Pro Thr Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
        115                 120                 125

Asn Thr Asp Glu Thr Phe Phe Gly Val Gln Trp Val Arg Pro
    130                 135                 140

<210> SEQ ID NO 17
<211> LENGTH: 105
<212> TYPE: PRT
<213> ORGANISM: Lama glama

<400> SEQUENCE: 17

Trp Asp Leu Ala Glu Leu Gln Leu Asn His Thr Gly Ser Arg Gln Asp
1               5                   10                  15

Pro Arg Leu Arg Trp Gln Gly Gly Pro Ala Leu Gly Arg Ser Phe Val
            20                  25                  30

His Gly Pro Glu Leu Asp Asn Gly Gln Leu Arg Val Gln Arg Ser Gly
        35                  40                  45

Ile Tyr Arg Leu His Ile Gln Leu Thr Leu Thr Asn Cys Ser Ser Thr
    50                  55                  60

Ala Gly Pro His Gly Ala Thr Leu Thr Val Gly Ile Cys Ser Pro Ala
65                  70                  75                  80

Ala His Ser Ile Ser Leu Leu Arg Leu Arg Phe Asp Arg Ser Cys Ser
                85                  90                  95

Val Ala Ser Gln Arg Leu Thr Pro Leu
            100                 105

<210> SEQ ID NO 18
<211> LENGTH: 142
<212> TYPE: PRT
<213> ORGANISM: Artificial
<220> FEATURE:
<223> OTHER INFORMATION: CD70 ECD Chimera

<400> SEQUENCE: 18

Ser Leu Gly Trp Asp Leu Ala Glu Leu Gln Leu Asn His Thr Gly Ser
1               5                   10                  15

Arg Gln Asp Pro Arg Leu Arg Trp Gln Gly Gly Pro Ala Leu Gly Arg
            20                  25                  30

Ser Phe Leu His Gly Pro Glu Leu Asp Lys Gly Gln Leu Arg Ile His
```

```
            35                  40                  45
Arg Asp Gly Ile Tyr Met Val His Ile Gln Val Thr Leu Ala Ile Cys
 50                  55                  60

Ser Ser Thr Thr Ala Ser Arg His His Pro Thr Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro
            130                 135                 140

<210> SEQ ID NO 19
<211> LENGTH: 142
<212> TYPE: PRT
<213> ORGANISM: Artificial
<220> FEATURE:
<223> OTHER INFORMATION: CD70 ECD Chimera

<400> SEQUENCE: 19

Ser Leu Gly Trp Asp Leu Ala Glu Leu Gln Leu Asn His Thr Gly Ser
1               5                   10                  15

Arg Gln Asp Pro Arg Leu Arg Trp Gln Gly Gly Pro Ala Leu Gly Arg
                20                  25                  30

Ser Phe Val His Gly Pro Glu Leu Asp Asn Gly Gln Leu Arg Val Gln
            35                  40                  45

Arg Ser Gly Ile Tyr Arg Leu His Ile Gln Leu Thr Leu Thr Asn Cys
 50                  55                  60

Ser Ser Thr Thr Ala Ser Arg His His Pro Thr Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro
            130                 135                 140

<210> SEQ ID NO 20
<211> LENGTH: 140
<212> TYPE: PRT
<213> ORGANISM: Artificial
<220> FEATURE:
<223> OTHER INFORMATION: CD70 ECD Chimera

<400> SEQUENCE: 20

Ser Leu Gly Trp Asp Leu Ala Glu Leu Gln Leu Asn His Thr Gly Ser
1               5                   10                  15

Arg Gln Asp Pro Arg Leu Arg Trp Gln Gly Gly Pro Ala Leu Gly Arg
                20                  25                  30

Ser Phe Val His Gly Pro Glu Leu Asp Asn Gly Gln Leu Arg Val Gln
            35                  40                  45

Arg Ser Gly Ile Tyr Arg Leu His Ile Gln Leu Thr Leu Thr Asn Cys
 50                  55                  60
```

```
Ser Ser Thr Ala Gly Pro His Gly Ala Thr Leu Thr Val Gly Ile Cys
 65                  70                  75                  80

Ser Pro Ala Ser Arg Ser Ile Ser Leu Leu Arg Leu Ser Phe His Gln
                 85                  90                  95

Gly Cys Thr Ile Ala Ser Gln Arg Leu Thr Pro Leu Ala Arg Gly Asp
                100                 105                 110

Thr Leu Cys Thr Asn Leu Thr Gly Thr Leu Leu Pro Ser Arg Asn Thr
            115                 120                 125

Asp Glu Thr Phe Phe Gly Val Gln Trp Val Arg Pro
130                 135                 140

<210> SEQ ID NO 21
<211> LENGTH: 356
<212> TYPE: PRT
<213> ORGANISM: Lama pacos

<400> SEQUENCE: 21

Ser Ile Pro Leu Pro Leu Phe Gln Ile Phe Ser Ser Asp Asn Tyr Thr
  1               5                  10                  15

Glu Asp Asp Leu Gly Ser Gly Asp Tyr Asp Ser Ile Lys Glu Pro Cys
                 20                  25                  30

Phe Gln Glu Glu Asn Ala His Phe Asn Arg Val Phe Leu Pro Thr Val
             35                  40                  45

Tyr Ser Ile Ile Phe Leu Thr Gly Ile Val Gly Asn Gly Leu Val Ile
 50                  55                  60

Leu Val Met Gly Tyr Gln Lys Lys Leu Arg Ser Met Thr Asp Lys Tyr
 65                  70                  75                  80

Arg Leu His Leu Ser Val Ala Asp Leu Leu Phe Val Leu Thr Leu Pro
                 85                  90                  95

Phe Trp Ala Val Asp Ala Val Ala Asn Trp Tyr Phe Gly Lys Phe Leu
                100                 105                 110

Cys Lys Ala Val His Val Ile Tyr Thr Val Asn Leu Tyr Ser Ser Val
            115                 120                 125

Leu Ile Leu Ala Phe Ile Ser Leu Asp Arg Tyr Leu Ala Ile Val His
130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Thr Glu Ala Glu Gly Arg Tyr Ile Cys Asp Arg
                180                 185                 190

Leu Tyr Pro Ser Asn Leu Trp Met Val Val Phe His Phe Gln His Ile
            195                 200                 205

Met Val Gly Leu Ile Leu Pro Gly Ile Val Ile Leu Ser Cys Tyr Cys
210                 215                 220

Ile Ile Ile Ser Lys Leu Ser His Ser Lys Gly Tyr Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Cys Phe Ile Leu Leu Glu
                260                 265                 270

Ile Ile Gln Gln Gly Cys Glu Phe Glu Ser Ile Val His Lys Trp Ile
            275                 280                 285

Ser Ile Thr Glu Ala Leu Ala Phe Phe His Cys Cys Leu Asn Pro Ile
290                 295                 300
```

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
            325                 330                 335

Lys Arg Gly Gly His Ser Ser Val Ser Thr Glu Ser Glu Ser Ser Ser
            340                 345                 350

Phe His Ser Ser
        355

<210> SEQ ID NO 22
<211> LENGTH: 352
<212> TYPE: PRT
<213> ORGANISM: Homo sapiens

<400> SEQUENCE: 22

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val

```
                305                 310                 315                 320
Ser Arg Gly Ser Ser Leu Lys Ile Leu Ser Lys Gly Lys Arg Gly Gly
                    325                 330                 335

His Ser Ser Val Ser Thr Glu Ser Glu Ser Ser Phe His Ser Ser
                    340                 345                 350

<210> SEQ ID NO 23
<211> LENGTH: 356
<212> TYPE: PRT
<213> ORGANISM: Homo sapiens

<400> SEQUENCE: 23

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
                20                  25                  30

Phe Arg Glu Glu Asn Ala Asn Phe Asn Lys Ile Phe Leu Pro Thr Ile
            35                  40                  45

Tyr Ser Ile Ile Phe Leu Thr Gly Ile Val Gly Asn Gly Leu Val Ile
        50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Val Phe Gln Phe Gln His Ile
        195                 200                 205

Met Val Gly Leu Ile Leu Pro Gly Ile Val Ile Leu Ser Cys Tyr Cys
210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
            260                 265                 270

Ile Ile Lys Gln Gly Cys Glu Phe Glu Asn Thr Val His Lys Trp Ile
        275                 280                 285

Ser Ile Thr Glu Ala Leu Ala Phe Phe His Cys Cys Leu Asn Pro Ile
290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335
```

```
Lys Arg Gly Gly His Ser Ser Val Ser Thr Glu Ser Glu Ser Ser Ser
                340                 345                 350

Phe His Ser Ser
        355

<210> SEQ ID NO 24
<211> LENGTH: 352
<212> TYPE: PRT
<213> ORGANISM: Artificial
<220> FEATURE:
<223> OTHER INFORMATION: Human-Alpaca CXCR4 chimera

<400> SEQUENCE: 24

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Val Tyr Ser Ile Ile
                35                  40                  45

Phe Leu Thr Gly Ile Val Gly Asn Gly Leu Val Ile Leu Val Met Gly
            50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Leu Thr Leu Pro Phe Trp Ala Val
                85                  90                  95

Asp Ala Val Ala Asn Trp Tyr Phe Gly Lys Phe Leu Cys Lys Ala Val
                100                 105                 110

His Val Ile Tyr Thr Val Asn Leu Tyr Ser Ser Val Leu Ile Leu Ala
                115                 120                 125

Phe Ile Ser Leu Asp Arg Tyr Leu Ala Ile Val His Ala Thr Asn Ser
            130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Thr Glu Ala Glu Gly Arg Tyr Ile Cys Asp Arg Leu Tyr Pro Ser
                180                 185                 190

Asn Leu Trp Met Val Val Phe His Phe Gln His Ile Met Val Gly Leu
                195                 200                 205

Ile Leu Pro Gly Ile Val Ile Leu Ser Cys Tyr Cys Ile Ile Ile Ser
            210                 215                 220

Lys Leu Ser His Ser Lys Gly Tyr Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Cys Phe Ile Leu Leu Glu Ile Ile Gln Gln
                260                 265                 270

Gly Cys Glu Phe Glu Ser Ile Val His Lys Trp Ile Ser Ile Thr Glu
                275                 280                 285

Ala Leu Ala Phe Phe His Cys Cys Leu Asn Pro Ile Leu Tyr Ala Phe
                290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335
```

His Ser Ser Val Ser Thr Glu Ser Glu Ser Ser Phe His Ser Ser
            340                 345                 350

<210> SEQ ID NO 25
<211> LENGTH: 356
<212> TYPE: PRT
<213> ORGANISM: Artificial
<220> FEATURE:
<223> OTHER INFORMATION: Human-Alpaca CXCR4 chimera

<400> SEQUENCE: 25

Met Ser Ile Pro Leu Pro Leu Gln Ile Tyr Thr Ser Asp Asn Tyr
1               5                   10                  15

Thr Glu Glu Met Gly Ser Gly Asp Tyr Asp Ser Met Lys Glu Pro Cys
                20                  25                  30

Phe Arg Glu Glu Asn Ala Asn Phe Asn Lys Ile Phe Leu Pro Thr Val
            35                  40                  45

Tyr Ser Ile Ile Phe Leu Thr Gly Ile Val Gly Asn Gly Leu Val Ile
    50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Leu Thr Leu Pro
                85                  90                  95

Phe Trp Ala Val Asp Ala Val Ala Asn Trp Tyr Phe Gly Lys Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
    130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Thr Ile Pro Asp Phe
                165                 170                 175

Ile Phe Ala Asn Val Thr Glu Ala Glu Gly Arg Tyr Ile Cys Asp Arg
            180                 185                 190

Leu Tyr Pro Ser Asn Leu Trp Met Val Val Phe His Phe Gln His Ile
        195                 200                 205

Met Val Gly Leu Ile Leu Pro Gly Ile Val Ile Leu Ser Cys Tyr Cys
    210                 215                 220

Ile Ile Ile Ser Lys Leu Ser His Ser Lys Gly Tyr Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Cys Phe Ile Leu Leu Glu
            260                 265                 270

Ile Ile Gln Gln Gly Cys Glu Phe Glu Ser Ile Val His Lys Trp Ile
        275                 280                 285

Ser Ile Thr Glu Ala Leu Ala Phe Phe His Cys Cys Leu Asn Pro Ile
    290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
            340                 345                 350

Phe His Ser Ser
         355

<210> SEQ ID NO 26
<211> LENGTH: 357
<212> TYPE: PRT
<213> ORGANISM: Artificial
<220> FEATURE:
<223> OTHER INFORMATION: Human-Alpaca CXCR4 chimera

<400> SEQUENCE: 26

Met Ser Ile Pro Leu Pro Phe Gln Ile Phe Ser Ser Asp Asn Tyr
1               5                   10                  15

Thr Glu Asp Asp Leu Gly Ser Gly Asp Tyr Asp Ser Ile Lys Glu Pro
                20                  25                  30

Cys Phe Gln Glu Glu Asn Ala His Phe Asn Arg Val Phe Leu Pro Thr
            35                  40                  45

Ile Tyr Ser Ile Ile Phe Leu Thr Gly Ile Val Gly Asn Gly Leu Val
        50                  55                  60

Ile Leu Val Met Gly Tyr Gln Lys Lys Leu Arg Ser Met Thr Asp Lys
65                  70                  75                  80

Tyr Arg Leu His Leu Ser Val Ala Asp Leu Leu Phe Val Ile Thr Leu
                85                  90                  95

Pro Phe Trp Ala Val Asp Ala Val Ala Asn Trp Tyr Phe Gly Asn Phe
            100                 105                 110

Leu Cys Lys Ala Val His Val Ile Tyr Thr Val Asn Leu Tyr Ser Ser
        115                 120                 125

Val Leu Ile Leu Ala Phe Ile Ser Leu Asp Arg Tyr Leu Ala Ile Val
130                 135                 140

His Ala Thr Asn Ser Gln Arg Pro Arg Lys Leu Leu Ala Glu Lys Val
145                 150                 155                 160

Val Tyr Val Gly Val Trp Ile Pro Ala Leu Leu Leu Thr Ile Pro Asp
                165                 170                 175

Phe Ile Phe Ala Asn Val Ser Glu Ala Asp Asp Arg Tyr Ile Cys Asp
            180                 185                 190

Arg Phe Tyr Pro Asn Asp Leu Trp Val Val Phe Gln Phe Gln His
        195                 200                 205

Ile Met Val Gly Leu Ile Leu Pro Gly Ile Val Ile Leu Ser Cys Tyr
210                 215                 220

Cys Ile Ile Ile Ser Lys Leu Ser His Ser Lys Gly His Gln Lys Arg
225                 230                 235                 240

Lys Ala Leu Lys Thr Thr Val Ile Leu Ile Leu Ala Phe Phe Ala Cys
                245                 250                 255

Trp Leu Pro Tyr Tyr Ile Gly Ile Ser Ile Asp Ser Phe Ile Leu Leu
            260                 265                 270

Glu Ile Ile Lys Gln Gly Cys Glu Phe Glu Asn Thr Val His Lys Trp
        275                 280                 285

Ile Ser Ile Thr Glu Ala Leu Ala Phe Phe His Cys Cys Leu Asn Pro
290                 295                 300

Ile Leu Tyr Ala Phe Leu Gly Ala Lys Phe Lys Thr Ser Ala Gln His
305                 310                 315                 320

Ala Leu Thr Ser Val Ser Arg Gly Ser Ser Leu Lys Ile Leu Ser Lys
                325                 330                 335

Gly Lys Arg Gly Gly His Ser Ser Val Ser Thr Glu Ser Glu Ser Ser
            340                 345                 350

```
Ser Phe His Ser Ser
        355

<210> SEQ ID NO 27
<211> LENGTH: 267
<212> TYPE: PRT
<213> ORGANISM: Artificial
<220> FEATURE:
<223> OTHER INFORMATION: IL-1 beta chimera

<400> SEQUENCE: 27

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Arg
            20                  25                  30

Lys Cys Cys Val Gln Pro Pro Asp Leu Gly Ser Leu Gly Asp Glu Gly
        35                  40                  45

Ile Gln Leu Gln Ile Ser His Gln Leu Tyr Asn Lys Ser Phe Arg Gln
    50                  55                  60

Val Val Ser Leu Ile Val Ala Met Glu Lys Leu Ser Lys Cys Thr Tyr
65                  70                  75                  80

Ser Gln Tyr Phe Gln Asp Asp Leu Arg Asn Ile Phe Ser Leu Ile
                85                  90                  95

Phe Glu Glu Glu Pro Val Thr Phe Glu Thr Cys Ala Asp Asp Phe Val
            100                 105                 110

Cys Asp Ala Val Val Gln Ser Leu Tyr Cys Lys Leu Gln Asp Lys Glu
        115                 120                 125

Gln Lys Ser Met Val Leu Ala Ser Pro Tyr Val Leu Gln Ala Leu His
    130                 135                 140

Leu Leu Ala Gln Asp Met Ser Arg Glu Val Val Phe Cys Met Ser Phe
145                 150                 155                 160

Val Gln Gly Asp Glu Asn Asn Ser Lys Thr Pro Val Val Leu Gly Leu
                165                 170                 175

Lys Glu Lys Asn Leu Tyr Leu Ser Cys Val Met Lys Gly Asp Lys Pro
            180                 185                 190

Thr Leu Gln Leu Glu Ala Leu Asp Pro Lys Ser Tyr Pro Arg Lys Asn
        195                 200                 205

Met Glu Lys Arg Phe Val Phe Tyr Lys Thr Glu Ile Lys Asp Arg Val
    210                 215                 220

Glu Phe Glu Ser Ala Leu Tyr Pro Asn Trp Tyr Ile Ser Thr Ser Thr
225                 230                 235                 240

Ala Glu Gln Arg Pro Val Phe Leu Gly Gln Ser Arg Gly Gly Gln Asp
                245                 250                 255

Ile Thr Asp Phe Thr Met Glu Thr Leu Ser Pro
            260                 265

<210> SEQ ID NO 28
<211> LENGTH: 266
<212> TYPE: PRT
<213> ORGANISM: Artificial
<220> FEATURE:
<223> OTHER INFORMATION: IL-1 beta chimera

<400> SEQUENCE: 28

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30
```

-continued

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Ser Phe Arg Gln Val
        50                  55                  60

Val Ser Leu Ile Val Ala Met Glu Lys Leu Ser Lys Cys Thr Tyr Ser
65                  70                  75                  80

Gln Tyr Phe Gln Asp Asp Leu Arg Asn Ile Phe Ser Leu Ile Phe
                85                  90                  95

Glu Glu Glu Pro Val Thr Phe Glu Thr Cys Ala Asp Asp Phe Val Cys
                100                 105                 110

Asp Ala Val Val Gln Ser Leu Tyr Cys Lys Leu Gln Asp Lys Glu Gln
                115                 120                 125

Lys Ser Met Val Leu Ala Ser Pro Tyr Val Leu Gln Ala Leu His Leu
            130                 135                 140

Leu Ala Gln Asp Met Ser Arg Glu Val Val Phe Cys Met Ser Phe Val
145                 150                 155                 160

Gln Gly Asp Glu Asn Asn Ser Lys Thr Pro Val Val Leu Gly Leu Lys
                165                 170                 175

Glu Lys Asn Leu Tyr Leu Ser Cys Val Met Lys Gly Asp Lys Pro Thr
            180                 185                 190

Leu Gln Leu Glu Ala Leu Asp Pro Lys Ser Tyr Pro Arg Lys Asn Met
            195                 200                 205

Glu Lys Arg Phe Val Phe Tyr Lys Thr Glu Ile Lys Asp Arg Val Glu
        210                 215                 220

Phe Glu Ser Ala Leu Tyr Pro Asn Trp Tyr Ile Ser Thr Ser Thr Ala
225                 230                 235                 240

Glu Gln Arg Pro Val Phe Leu Gly Gln Ser Arg Gly Gly Gln Asp Ile
                245                 250                 255

Thr Asp Phe Thr Met Glu Thr Leu Ser Pro
                260                 265

<210> SEQ ID NO 29
<211> LENGTH: 268
<212> TYPE: PRT
<213> ORGANISM: Artificial
<220> FEATURE:
<223> OTHER INFORMATION: IL-1 beta chimera

<400> SEQUENCE: 29

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Arg Asn Ile Phe Ser Leu
                85                  90                  95

Ile Phe Glu Glu Glu Pro Val Thr Phe Glu Thr Cys Ala Asp Asp Phe
                100                 105                 110

Val Cys Asp Ala Val Val Gln Ser Leu Tyr Cys Lys Leu Gln Asp Lys
            115                 120                 125

```
Glu Gln Lys Ser Met Val Leu Ala Ser Pro Tyr Val Leu Gln Ala Leu
        130                 135                 140

His Leu Leu Ala Gln Asp Met Ser Arg Glu Val Val Phe Cys Met Ser
145                 150                 155                 160

Phe Val Gln Gly Asp Glu Asn Asn Ser Lys Thr Pro Val Val Leu Gly
                165                 170                 175

Leu Lys Glu Lys Asn Leu Tyr Leu Ser Cys Val Met Lys Gly Asp Lys
                180                 185                 190

Pro Thr Leu Gln Leu Glu Ala Leu Asp Pro Lys Ser Tyr Pro Arg Lys
                195                 200                 205

Asn Met Glu Lys Arg Phe Val Phe Tyr Lys Thr Glu Ile Lys Asp Arg
            210                 215                 220

Val Glu Phe Glu Ser Ala Leu Tyr Pro Asn Trp Tyr Ile Ser Thr Ser
225                 230                 235                 240

Thr Ala Glu Gln Arg Pro Val Phe Leu Gly Gln Ser Arg Gly Gly Gln
                245                 250                 255

Asp Ile Thr Asp Phe Thr Met Glu Thr Leu Ser Pro
                260                 265

<210> SEQ ID NO 30
<211> LENGTH: 269
<212> TYPE: PRT
<213> ORGANISM: Artificial
<220> FEATURE:
<223> OTHER INFORMATION: IL-1 beta chimera

<400> SEQUENCE: 30

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Gln Ser Leu Tyr Cys Lys Leu Gln Asp
            115                 120                 125

Lys Glu Gln Lys Ser Met Val Leu Ala Ser Pro Tyr Val Leu Gln Ala
    130                 135                 140

Leu His Leu Leu Ala Gln Asp Met Ser Arg Glu Val Val Phe Cys Met
145                 150                 155                 160

Ser Phe Val Gln Gly Asp Glu Asn Asn Ser Lys Thr Pro Val Val Leu
                165                 170                 175

Gly Leu Lys Glu Lys Asn Leu Tyr Leu Ser Cys Val Met Lys Gly Asp
            180                 185                 190

Lys Pro Thr Leu Gln Leu Glu Ala Leu Asp Pro Lys Ser Tyr Pro Arg
    195                 200                 205

Lys Asn Met Glu Lys Arg Phe Val Phe Tyr Lys Thr Glu Ile Lys Asp
210                 215                 220
```

-continued

Arg Val Glu Phe Glu Ser Ala Leu Tyr Pro Asn Trp Tyr Ile Ser Thr
225                 230                 235                 240

Ser Thr Ala Glu Gln Arg Pro Val Phe Leu Gly Gln Ser Arg Gly Gly
            245                 250                 255

Gln Asp Ile Thr Asp Phe Thr Met Glu Thr Leu Ser Pro
        260                 265

<210> SEQ ID NO 31
<211> LENGTH: 269
<212> TYPE: PRT
<213> ORGANISM: Artificial
<220> FEATURE:
<223> OTHER INFORMATION: IL-1 beta chimera

<400> SEQUENCE: 31

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Ser Arg Glu Val Val Phe Cys Met
145                 150                 155                 160

Ser Phe Val Gln Gly Asp Glu Asn Asn Ser Lys Thr Pro Val Val Leu
                165                 170                 175

Gly Leu Lys Glu Lys Asn Leu Tyr Leu Ser Cys Val Met Lys Gly Asp
            180                 185                 190

Lys Pro Thr Leu Gln Leu Glu Ala Leu Asp Pro Lys Ser Tyr Pro Arg
        195                 200                 205

Lys Asn Met Glu Lys Arg Phe Val Phe Tyr Lys Thr Glu Ile Lys Asp
    210                 215                 220

Arg Val Glu Phe Glu Ser Ala Leu Tyr Pro Asn Trp Tyr Ile Ser Thr
225                 230                 235                 240

Ser Thr Ala Glu Gln Arg Pro Val Phe Leu Gly Gln Ser Arg Gly Gly
            245                 250                 255

Gln Asp Ile Thr Asp Phe Thr Met Glu Thr Leu Ser Pro
        260                 265

<210> SEQ ID NO 32
<211> LENGTH: 269
<212> TYPE: PRT
<213> ORGANISM: Artificial
<220> FEATURE:
<223> OTHER INFORMATION: IL-1 beta chimera

<400> SEQUENCE: 32

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Met Lys Gly Asp
            180                 185                 190

Lys Pro Thr Leu Gln Leu Glu Ala Leu Asp Pro Lys Ser Tyr Pro Arg
        195                 200                 205

Lys Asn Met Glu Lys Arg Phe Val Phe Tyr Lys Thr Glu Ile Lys Asp
    210                 215                 220

Arg Val Glu Phe Glu Ser Ala Leu Tyr Pro Asn Trp Tyr Ile Ser Thr
225                 230                 235                 240

Ser Thr Ala Glu Gln Arg Pro Val Phe Leu Gly Gln Ser Arg Gly Gly
                245                 250                 255

Gln Asp Ile Thr Asp Phe Thr Met Glu Thr Leu Ser Pro
            260                 265
```

<210> SEQ ID NO 33
<211> LENGTH: 269
<212> TYPE: PRT
<213> ORGANISM: Artificial
<220> FEATURE:
<223> OTHER INFORMATION: IL-1 beta chimera

<400> SEQUENCE: 33

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
```

```
            85                  90                  95
Ile Phe Glu Glu Glu Pro Ile Phe Phe Asp Thr Trp Asp Asn Glu Ala
            100                 105                 110
Tyr Val His Asp Ala Pro Val Arg Ser Leu Asn Cys Thr Leu Arg Asp
            115                 120                 125
Ser Gln Gln Lys Ser Leu Val Met Ser Gly Pro Tyr Glu Leu Lys Ala
            130                 135                 140
Leu His Leu Gln Gly Gln Asp Met Glu Gln Gln Val Val Phe Ser Met
145                 150                 155                 160
Ser Phe Val Gln Gly Glu Glu Ser Asn Asp Lys Ile Pro Val Ala Leu
                    165                 170                 175
Gly Leu Lys Glu Lys Asn Leu Tyr Leu Ser Cys Val Leu Lys Asp Asp
                    180                 185                 190
Lys Pro Thr Leu Gln Leu Glu Ser Val Asp Pro Lys Asn Tyr Pro Lys
                    195                 200                 205
Lys Asn Met Glu Lys Arg Phe Val Phe Tyr Lys Thr Glu Ile Lys Asp
                    210                 215                 220
Arg Val Glu Phe Glu Ser Ala Leu Tyr Pro Asn Trp Tyr Ile Ser Thr
225                 230                 235                 240
Ser Thr Ala Glu Gln Arg Pro Val Phe Leu Gly Gln Ser Arg Gly Gly
                    245                 250                 255
Gln Asp Ile Thr Asp Phe Thr Met Glu Thr Leu Ser Pro
                    260                 265
```

<210> SEQ ID NO 34
<211> LENGTH: 269
<212> TYPE: PRT
<213> ORGANISM: Artificial
<220> FEATURE:
<223> OTHER INFORMATION: IL-1 beta chimera

<400> SEQUENCE: 34

```
Met Ala Glu Val Pro Glu Leu Ala Ser Glu Met Met Ala Tyr Tyr Ser
1               5                   10                  15
Gly Asn Glu Asp Asp Leu Phe Phe Glu Ala Asp Gly Pro Lys Gln Met
            20                  25                  30
Lys Cys Ser Phe Gln Asp Leu Asp Leu Cys Pro Leu Asp Gly Gly Ile
            35                  40                  45
Gln Leu Arg Ile Ser Asp His His Tyr Ser Lys Gly Phe Arg Gln Ala
            50                  55                  60
Ala Ser Val Val Val Ala Met Asp Lys Leu Arg Lys Met Leu Val Pro
65                  70                  75                  80
Cys Pro Gln Thr Phe Gln Glu Asn Asp Leu Ser Thr Phe Phe Pro Phe
                    85                  90                  95
Ile Phe Glu Glu Glu Pro Ile Phe Phe Asp Thr Trp Asp Asn Glu Ala
            100                 105                 110
Tyr Val His Asp Ala Pro Val Arg Ser Leu Asn Cys Thr Leu Arg Asp
            115                 120                 125
Ser Gln Gln Lys Ser Leu Val Met Ser Gly Pro Tyr Glu Leu Lys Ala
            130                 135                 140
Leu His Leu Gln Gly Gln Asp Met Glu Gln Gln Val Val Phe Ser Met
145                 150                 155                 160
Ser Phe Val Gln Gly Glu Glu Ser Asn Asp Lys Ile Pro Val Ala Leu
                    165                 170                 175
Gly Leu Lys Glu Lys Asn Leu Tyr Leu Ser Cys Val Leu Lys Asp Asp
```

```
            180             185             190
Lys Pro Thr Leu Gln Leu Glu Ser Val Asp Pro Lys Asn Tyr Pro Lys
            195                 200                 205
Lys Asn Met Glu Lys Arg Phe Val Phe Tyr Lys Thr Glu Ile Lys Asp
210                 215                 220
Arg Val Glu Phe Glu Ser Ala Leu Tyr Pro Asn Trp Tyr Ile Ser Thr
225                 230                 235                 240
Ser Thr Ala Glu Gln Arg Pro Val Phe Leu Gly Gln Ser Arg Gly Gly
            245                 250                 255
Gln Asp Ile Thr Asp Phe Thr Met Glu Thr Leu Ser Pro
            260                 265
```

<210> SEQ ID NO 35
<211> LENGTH: 269
<212> TYPE: PRT
<213> ORGANISM: Artificial
<220> FEATURE:
<223> OTHER INFORMATION: IL-1 beta chimera

<400> SEQUENCE: 35

```
Met Ala Thr Val Pro Glu Pro Thr Ser Glu Met Met Ala Tyr Tyr Ser
1               5                   10                  15
Asp Asn Asp Asn Asp Leu Leu Phe Glu Ala Asp Gly Pro Lys Gln Met
                20                  25                  30
Lys Cys Ser Phe Gln Asp Leu Asp Leu Cys Pro Leu Asp Gly Gly Ile
            35                  40                  45
Gln Leu Arg Ile Ser Asp His His Tyr Ser Lys Gly Phe Arg Gln Ala
50                  55                  60
Ala Ser Val Val Val Ala Met Asp Lys Leu Arg Lys Met Leu Val Pro
65                  70                  75                  80
Cys Pro Gln Thr Phe Gln Glu Asn Asp Leu Ser Thr Phe Phe Pro Phe
                85                  90                  95
Ile Phe Glu Glu Glu Pro Ile Phe Phe Asp Thr Trp Asp Asn Glu Ala
            100                 105                 110
Tyr Val His Asp Ala Pro Val Arg Ser Leu Asn Cys Thr Leu Arg Asp
            115                 120                 125
Ser Gln Gln Lys Ser Leu Val Met Ser Gly Pro Tyr Glu Leu Lys Ala
130                 135                 140
Leu His Leu Gln Gly Gln Asp Met Glu Gln Gln Val Val Phe Ser Met
145                 150                 155                 160
Ser Phe Val Gln Gly Glu Glu Ser Asn Asp Lys Ile Pro Val Ala Leu
                165                 170                 175
Gly Leu Lys Glu Lys Asn Leu Tyr Leu Ser Cys Val Leu Lys Asp Asp
            180                 185                 190
Lys Pro Thr Leu Gln Leu Glu Ser Val Asp Pro Lys Asn Tyr Pro Lys
            195                 200                 205
Lys Lys Met Glu Lys Arg Phe Val Phe Asn Lys Ile Glu Ile Asn Asn
            210                 215                 220
Lys Leu Glu Phe Glu Ser Ala Gln Phe Pro Asn Trp Tyr Ile Ser Thr
225                 230                 235                 240
Ser Gln Ala Glu Asn Met Pro Val Phe Leu Gly Gly Thr Lys Gly Gly
                245                 250                 255
Gln Asp Ile Thr Asp Phe Thr Met Gln Phe Val Ser Ser
            260                 265
```

<210> SEQ ID NO 36
<211> LENGTH: 270
<212> TYPE: PRT
<213> ORGANISM: Artificial
<220> FEATURE:
<223> OTHER INFORMATION: IL-1 beta chimera

<400> SEQUENCE: 36

```
Met Ala Thr Val Pro Glu Pro Thr Ser Glu Met Met Ala Tyr Tyr Ser
1               5                   10                  15

Asp Asn Asp Asn Asp Leu Leu Phe Glu Ala Asp Gly Pro Lys Gln Arg
            20                  25                  30

Lys Cys Cys Val Gln Pro Pro Asp Leu Gly Ser Leu Gly Asp Glu Gly
        35                  40                  45

Ile Gln Leu Gln Ile Ser His Gln Leu Tyr Asn Lys Gly Phe Arg Gln
    50                  55                  60

Ala Ala Ser Val Val Ala Met Asp Lys Leu Arg Lys Met Leu Val
65                  70                  75                  80

Pro Cys Pro Gln Thr Phe Gln Glu Asn Asp Leu Ser Thr Phe Phe Pro
                85                  90                  95

Phe Ile Phe Glu Glu Pro Ile Phe Phe Asp Thr Trp Asp Asn Glu
                100                 105                 110

Ala Tyr Val His Asp Ala Pro Val Arg Ser Leu Asn Cys Thr Leu Arg
            115                 120                 125

Asp Ser Gln Gln Lys Ser Leu Val Met Ser Gly Pro Tyr Glu Leu Lys
        130                 135                 140

Ala Leu His Leu Gln Gly Gln Asp Met Glu Gln Gln Val Val Phe Ser
145                 150                 155                 160

Met Ser Phe Val Gln Gly Glu Glu Ser Asn Asp Lys Ile Pro Val Ala
                165                 170                 175

Leu Gly Leu Lys Glu Lys Asn Leu Tyr Leu Ser Cys Val Leu Lys Asp
            180                 185                 190

Asp Lys Pro Thr Leu Gln Leu Glu Ser Val Asp Pro Lys Asn Tyr Pro
        195                 200                 205

Lys Lys Lys Met Glu Lys Arg Phe Val Phe Asn Lys Ile Glu Ile Asn
    210                 215                 220

Asn Lys Leu Glu Phe Glu Ser Ala Gln Phe Pro Asn Trp Tyr Ile Ser
225                 230                 235                 240

Thr Ser Gln Ala Glu Asn Met Pro Val Phe Leu Gly Gly Thr Lys Gly
                245                 250                 255

Gly Gln Asp Ile Thr Asp Phe Thr Met Gln Phe Val Ser Ser
            260                 265                 270
```

<210> SEQ ID NO 37
<211> LENGTH: 268
<212> TYPE: PRT
<213> ORGANISM: Artificial
<220> FEATURE:
<223> OTHER INFORMATION: IL-1 beta chimera

<400> SEQUENCE: 37

```
Met Ala Thr Val Pro Glu Pro Thr Ser Glu Met Met Ala Tyr Tyr Ser
1               5                   10                  15

Asp Asn Asp Asn Asp Leu Leu Phe Glu Ala Asp Gly Pro Lys Gln Arg
            20                  25                  30

Lys Cys Cys Val Gln Pro Pro Asp Leu Gly Ser Leu Gly Asp Glu Gly
        35                  40                  45
```

```
Ile Gln Leu Gln Ile Ser His Gln Leu Tyr Asn Lys Ser Phe Arg Gln
    50                  55                  60

Val Val Ser Leu Ile Val Ala Met Glu Lys Leu Ser Lys Cys Thr Tyr
65                  70                  75                  80

Ser Gln Tyr Phe Gln Asp Asp Leu Ser Thr Phe Pro Phe Ile
                85                  90                  95

Phe Glu Glu Glu Pro Ile Phe Phe Asp Thr Trp Asp Asn Glu Ala Tyr
                100                 105                 110

Val His Asp Ala Pro Val Arg Ser Leu Asn Cys Thr Leu Arg Asp Ser
            115                 120                 125

Gln Gln Lys Ser Leu Val Met Ser Gly Pro Tyr Glu Leu Lys Ala Leu
    130                 135                 140

His Leu Gln Gly Gln Asp Met Glu Gln Gln Val Val Phe Ser Met Ser
145                 150                 155                 160

Phe Val Gln Gly Glu Glu Ser Asn Asp Lys Ile Pro Val Ala Leu Gly
                165                 170                 175

Leu Lys Glu Lys Asn Leu Tyr Leu Ser Cys Val Leu Lys Asp Asp Lys
            180                 185                 190

Pro Thr Leu Gln Leu Glu Ser Val Asp Pro Lys Asn Tyr Pro Lys Lys
        195                 200                 205

Lys Met Glu Lys Arg Phe Val Phe Asn Lys Ile Glu Ile Asn Asn Lys
    210                 215                 220

Leu Glu Phe Glu Ser Ala Gln Phe Pro Asn Trp Tyr Ile Ser Thr Ser
225                 230                 235                 240

Gln Ala Glu Asn Met Pro Val Phe Leu Gly Gly Thr Lys Gly Gly Gln
                245                 250                 255

Asp Ile Thr Asp Phe Thr Met Gln Phe Val Ser Ser
                260                 265

<210> SEQ ID NO 38
<211> LENGTH: 267
<212> TYPE: PRT
<213> ORGANISM: Artificial
<220> FEATURE:
<223> OTHER INFORMATION: IL-1 beta chimera

<400> SEQUENCE: 38

Met Ala Thr Val Pro Glu Pro Thr Ser Glu Met Met Ala Tyr Tyr Ser
1               5                   10                  15

Asp Asn Asp Asp Leu Leu Phe Glu Ala Asp Gly Pro Lys Gln Arg
                20                  25                  30

Lys Cys Cys Val Gln Pro Pro Asp Leu Gly Ser Leu Gly Asp Glu Gly
            35                  40                  45

Ile Gln Leu Gln Ile Ser His Gln Leu Tyr Asn Lys Ser Phe Arg Gln
    50                  55                  60

Val Val Ser Leu Ile Val Ala Met Glu Lys Leu Ser Lys Cys Thr Tyr
65                  70                  75                  80

Ser Gln Tyr Phe Gln Asp Asp Leu Arg Asn Ile Phe Ser Leu Ile
                85                  90                  95

Phe Glu Glu Glu Pro Val Thr Phe Glu Thr Cys Ala Asp Phe Val
                100                 105                 110

Cys Asp Ala Val Val Arg Ser Leu Asn Cys Thr Leu Arg Asp Ser Gln
            115                 120                 125

Gln Lys Ser Leu Val Met Ser Gly Pro Tyr Glu Leu Lys Ala Leu His
    130                 135                 140
```

```
Leu Gln Gly Gln Asp Met Glu Gln Gln Val Val Phe Ser Met Ser Phe
145                 150                 155                 160

Val Gln Gly Glu Glu Ser Asn Asp Lys Ile Pro Val Ala Leu Gly Leu
                165                 170                 175

Lys Glu Lys Asn Leu Tyr Leu Ser Cys Val Leu Lys Asp Asp Lys Pro
            180                 185                 190

Thr Leu Gln Leu Glu Ser Val Asp Pro Lys Asn Tyr Pro Lys Lys Lys
        195                 200                 205

Met Glu Lys Arg Phe Val Phe Asn Lys Ile Glu Ile Asn Asn Lys Leu
    210                 215                 220

Glu Phe Glu Ser Ala Gln Phe Pro Asn Trp Tyr Ile Ser Thr Ser Gln
225                 230                 235                 240

Ala Glu Asn Met Pro Val Phe Leu Gly Gly Thr Lys Gly Gly Gln Asp
                245                 250                 255

Ile Thr Asp Phe Thr Met Gln Phe Val Ser Ser
                260                 265

<210> SEQ ID NO 39
<211> LENGTH: 267
<212> TYPE: PRT
<213> ORGANISM: Artificial
<220> FEATURE:
<223> OTHER INFORMATION: IL-1 beta chimera

<400> SEQUENCE: 39

Met Ala Thr Val Pro Glu Pro Thr Ser Glu Met Met Ala Tyr Tyr Ser
1               5                   10                  15

Asp Asn Asp Asn Asp Leu Leu Phe Glu Ala Asp Gly Pro Lys Gln Arg
                20                  25                  30

Lys Cys Cys Val Gln Pro Pro Asp Leu Gly Ser Leu Gly Asp Glu Gly
            35                  40                  45

Ile Gln Leu Gln Ile Ser His Gln Leu Tyr Asn Lys Ser Phe Arg Gln
        50                  55                  60

Val Val Ser Leu Ile Val Ala Met Glu Lys Leu Ser Lys Cys Thr Tyr
65                  70                  75                  80

Ser Gln Tyr Phe Gln Asp Asp Leu Arg Asn Ile Phe Ser Leu Ile
                85                  90                  95

Phe Glu Glu Glu Pro Val Thr Phe Glu Thr Cys Ala Asp Asp Phe Val
            100                 105                 110

Cys Asp Ala Val Val Gln Ser Leu Tyr Cys Lys Leu Gln Asp Lys Glu
        115                 120                 125

Gln Lys Ser Met Val Leu Ala Ser Pro Tyr Val Leu Gln Ala Leu His
    130                 135                 140

Leu Leu Ala Gln Asp Met Glu Gln Gln Val Val Phe Ser Met Ser Phe
145                 150                 155                 160

Val Gln Gly Glu Glu Ser Asn Asp Lys Ile Pro Val Ala Leu Gly Leu
                165                 170                 175

Lys Glu Lys Asn Leu Tyr Leu Ser Cys Val Leu Lys Asp Asp Lys Pro
            180                 185                 190

Thr Leu Gln Leu Glu Ser Val Asp Pro Lys Asn Tyr Pro Lys Lys Lys
        195                 200                 205

Met Glu Lys Arg Phe Val Phe Asn Lys Ile Glu Ile Asn Asn Lys Leu
    210                 215                 220

Glu Phe Glu Ser Ala Gln Phe Pro Asn Trp Tyr Ile Ser Thr Ser Gln
225                 230                 235                 240
```

```
Ala Glu Asn Met Pro Val Phe Leu Gly Gly Thr Lys Gly Gly Gln Asp
            245                 250                 255

Ile Thr Asp Phe Thr Met Gln Phe Val Ser Ser
            260                 265

<210> SEQ ID NO 40
<211> LENGTH: 267
<212> TYPE: PRT
<213> ORGANISM: Artificial
<220> FEATURE:
<223> OTHER INFORMATION: IL-1 beta chimera

<400> SEQUENCE: 40

Met Ala Thr Val Pro Glu Pro Thr Ser Glu Met Met Ala Tyr Tyr Ser
1               5                   10                  15

Asp Asn Asp Asn Asp Leu Leu Phe Glu Ala Asp Gly Pro Lys Gln Arg
            20                  25                  30

Lys Cys Cys Val Gln Pro Pro Asp Leu Gly Ser Leu Gly Asp Glu Gly
            35                  40                  45

Ile Gln Leu Gln Ile Ser His Gln Leu Tyr Asn Lys Ser Phe Arg Gln
    50                  55                  60

Val Val Ser Leu Ile Val Ala Met Glu Lys Leu Ser Lys Cys Thr Tyr
65                  70                  75                  80

Ser Gln Tyr Phe Gln Asp Asp Leu Arg Asn Ile Phe Ser Leu Ile
                85                  90                  95

Phe Glu Glu Glu Pro Val Thr Phe Glu Thr Cys Ala Asp Asp Phe Val
                100                 105                 110

Cys Asp Ala Val Val Gln Ser Leu Tyr Cys Lys Leu Gln Asp Lys Glu
            115                 120                 125

Gln Lys Ser Met Val Leu Ala Ser Pro Tyr Val Leu Gln Ala Leu His
        130                 135                 140

Leu Leu Ala Gln Asp Met Ser Arg Glu Val Val Phe Cys Met Ser Phe
145                 150                 155                 160

Val Gln Gly Asp Glu Asn Asn Ser Lys Thr Pro Val Val Leu Gly Leu
                165                 170                 175

Lys Glu Lys Asn Leu Tyr Leu Ser Cys Val Leu Lys Asp Asp Lys Pro
            180                 185                 190

Thr Leu Gln Leu Glu Ser Val Asp Pro Lys Asn Tyr Pro Lys Lys Lys
        195                 200                 205

Met Glu Lys Arg Phe Val Phe Asn Lys Ile Glu Ile Asn Asn Lys Leu
    210                 215                 220

Glu Phe Glu Ser Ala Gln Phe Pro Asn Trp Tyr Ile Ser Thr Ser Gln
225                 230                 235                 240

Ala Glu Asn Met Pro Val Phe Leu Gly Gly Thr Lys Gly Gly Gln Asp
            245                 250                 255

Ile Thr Asp Phe Thr Met Gln Phe Val Ser Ser
            260                 265

<210> SEQ ID NO 41
<211> LENGTH: 267
<212> TYPE: PRT
<213> ORGANISM: Artificial
<220> FEATURE:
<223> OTHER INFORMATION: IL-1 beta chimera

<400> SEQUENCE: 41

Met Ala Thr Val Pro Glu Pro Thr Ser Glu Met Met Ala Tyr Tyr Ser
1               5                   10                  15
```

```
Asp Asn Asp Asn Asp Leu Leu Phe Glu Ala Asp Gly Pro Lys Gln Arg
            20                  25                  30

Lys Cys Cys Val Gln Pro Pro Asp Leu Gly Ser Leu Gly Asp Glu Gly
        35                  40                  45

Ile Gln Leu Gln Ile Ser His Gln Leu Tyr Asn Lys Ser Phe Arg Gln
    50                  55                  60

Val Val Ser Leu Ile Val Ala Met Glu Lys Leu Ser Lys Cys Thr Tyr
65                  70                  75                  80

Ser Gln Tyr Phe Gln Asp Asp Leu Arg Asn Ile Phe Ser Leu Ile
                85                  90                  95

Phe Glu Glu Glu Pro Val Thr Phe Glu Thr Cys Ala Asp Asp Phe Val
            100                 105                 110

Cys Asp Ala Val Val Gln Ser Leu Tyr Cys Lys Leu Gln Asp Lys Glu
            115                 120                 125

Gln Lys Ser Met Val Leu Ala Ser Pro Tyr Val Leu Gln Ala Leu His
    130                 135                 140

Leu Leu Ala Gln Asp Met Ser Arg Glu Val Val Phe Cys Met Ser Phe
145                 150                 155                 160

Val Gln Gly Asp Glu Asn Asn Ser Lys Thr Pro Val Val Leu Gly Leu
                165                 170                 175

Lys Glu Lys Asn Leu Tyr Leu Ser Cys Val Met Lys Gly Asp Lys Pro
            180                 185                 190

Thr Leu Gln Leu Glu Ala Leu Asp Pro Lys Ser Tyr Pro Arg Lys Lys
        195                 200                 205

Met Glu Lys Arg Phe Val Phe Asn Lys Ile Glu Ile Asn Asn Lys Leu
    210                 215                 220

Glu Phe Glu Ser Ala Gln Phe Pro Asn Trp Tyr Ile Ser Thr Ser Gln
225                 230                 235                 240

Ala Glu Asn Met Pro Val Phe Leu Gly Gly Thr Lys Gly Gly Gln Asp
                245                 250                 255

Ile Thr Asp Phe Thr Met Gln Phe Val Ser Ser
            260                 265

<210> SEQ ID NO 42
<211> LENGTH: 267
<212> TYPE: PRT
<213> ORGANISM: Artificial
<220> FEATURE:
<223> OTHER INFORMATION: IL-1 beta chimera

<400> SEQUENCE: 42

Met Ala Thr Val Pro Glu Pro Thr Ser Glu Met Met Ala Tyr Tyr Ser
1               5                   10                  15

Asp Asn Asp Asn Asp Leu Leu Phe Glu Ala Asp Gly Pro Lys Gln Arg
            20                  25                  30

Lys Cys Cys Val Gln Pro Pro Asp Leu Gly Ser Leu Gly Asp Glu Gly
        35                  40                  45

Ile Gln Leu Gln Ile Ser His Gln Leu Tyr Asn Lys Ser Phe Arg Gln
    50                  55                  60

Val Val Ser Leu Ile Val Ala Met Glu Lys Leu Ser Lys Cys Thr Tyr
65                  70                  75                  80

Ser Gln Tyr Phe Gln Asp Asp Leu Arg Asn Ile Phe Ser Leu Ile
                85                  90                  95

Phe Glu Glu Glu Pro Val Thr Phe Glu Thr Cys Ala Asp Asp Phe Val
            100                 105                 110
```

-continued

```
Cys Asp Ala Val Val Gln Ser Leu Tyr Cys Lys Leu Gln Asp Lys Glu
        115                 120                 125

Gln Lys Ser Met Val Leu Ala Ser Pro Tyr Val Leu Gln Ala Leu His
        130                 135                 140

Leu Leu Ala Gln Asp Met Ser Arg Glu Val Val Phe Cys Met Ser Phe
145                 150                 155                 160

Val Gln Gly Asp Glu Asn Asn Ser Lys Thr Pro Val Val Leu Gly Leu
                165                 170                 175

Lys Glu Lys Asn Leu Tyr Leu Ser Cys Val Met Lys Gly Asp Lys Pro
                180                 185                 190

Thr Leu Gln Leu Glu Ala Leu Asp Pro Lys Ser Tyr Pro Arg Lys Asn
        195                 200                 205

Met Glu Lys Arg Phe Val Phe Tyr Lys Thr Glu Ile Lys Asp Arg Val
        210                 215                 220

Glu Phe Glu Ser Ala Leu Tyr Pro Asn Trp Tyr Ile Ser Thr Ser Thr
225                 230                 235                 240

Ala Glu Gln Arg Pro Val Phe Leu Gly Gln Ser Arg Gly Gly Gln Asp
                245                 250                 255

Ile Thr Asp Phe Thr Met Glu Thr Leu Ser Pro
                260                 265
```